(12) United States Patent
Holers et al.

(10) Patent No.: US 8,911,733 B2
(45) Date of Patent: Dec. 16, 2014

(54) INHIBITION OF THE ALTERNATIVE COMPLEMENT PATHWAY FOR TREATMENT OF TRAUMATIC BRAIN INJURY, SPINAL CORD INJURY AND RELATED CONDITIONS

(75) Inventors: Vernon Michael Holers, Denver, CO (US); Joshua M. Thurman, Greenwood Village, CO (US); Stephen Tomlinson, Mount Pleasant, SC (US); Philip F. Stahel, Denver, CO (US)

(73) Assignees: MUSC Foundation for Research Development, Charleston, SC (US); The Regents of the University of Colorado, a body corporate, Denver, CO (US)

( * ) Notice: Subject to any disclaimer, the term of this patent is extended or adjusted under 35 U.S.C. 154(b) by 1690 days.

(21) Appl. No.: 11/441,828

(22) Filed: May 26, 2006

(65) Prior Publication Data

US 2006/0292141 A1 Dec. 28, 2006

Related U.S. Application Data

(60) Provisional application No. 60/685,289, filed on May 26, 2005.

(51) Int. Cl.
- *A61K 39/395* (2006.01)
- *C07K 16/42* (2006.01)
- *C07K 16/18* (2006.01)
- *A61K 39/00* (2006.01)

(52) U.S. Cl.
CPC ............. *C07K 16/42* (2013.01); *C07K 16/18* (2013.01); *A61K 2039/505* (2013.01); *C07K 2316/96* (2013.01); *C07K 2319/30* (2013.01)
USPC ................. 424/145.1; 424/141.1; 424/130.1

(58) Field of Classification Search
None
See application file for complete search history.

(56) References Cited

U.S. PATENT DOCUMENTS

| | | | |
|---|---|---|---|
| 4,845,083 A | 7/1989 | Fortin et al. | |
| 4,883,784 A | 11/1989 | Kaneko | |
| 5,679,546 A | 10/1997 | Ko et al. | |
| 5,869,615 A | 2/1999 | Hourcade et al. | |
| 5,976,540 A | 11/1999 | Rittershaus et al. | |
| 6,165,463 A | 12/2000 | Platz et al. | |
| 6,248,365 B1 | 6/2001 | Romisch et al. | |
| 6,458,360 B1 | 10/2002 | Fearon et al. | |
| 6,521,450 B1 | 2/2003 | Atkinson et al. | |
| 6,820,011 B2 | 11/2004 | Chen et al. | |
| 6,897,290 B1 | 5/2005 | Atkinson et al. | |
| 7,759,304 B2 | 7/2010 | Gilkeson et al. | |
| 7,964,105 B2 | 6/2011 | Moss | |
| 7,964,705 B2 | 6/2011 | Emlen et al. | |
| 7,999,082 B2 | 8/2011 | Holers et al. | |
| 8,007,804 B2 | 8/2011 | Tomlinson et al. | |
| 2002/0015701 A1 | 2/2002 | Gupta-Bansal et al. | |
| 2002/0081293 A1 | 6/2002 | Fung et al. | |
| 2003/0198636 A1 | 10/2003 | Gupta-Bansal et al. | |
| 2003/0235582 A1 | 12/2003 | Singh et al. | |
| 2004/0014782 A1 | 1/2004 | Krause | |
| 2005/0107319 A1 | 5/2005 | Bansal | |
| 2005/0169915 A1 | 8/2005 | Do Couto et al. | |
| 2005/0255552 A1 | 11/2005 | Flynn et al. | |
| 2005/0260198 A1 | 11/2005 | Holers et al. | |
| 2006/0002944 A1 | 1/2006 | Ashkenazi et al. | |
| 2006/0134098 A1 | 6/2006 | Bebbington et al. | |
| 2006/0178308 A1 | 8/2006 | Schwaeble et al. | |
| 2006/0263819 A1 | 11/2006 | Hageman et al. | |
| 2006/0292141 A1 | 12/2006 | Holers et al. | |
| 2007/0020647 A1 | 1/2007 | Hageman et al. | |
| 2007/0065433 A1 | 3/2007 | Mollnes et al. | |
| 2007/0183970 A1 | 8/2007 | Goldenberg et al. | |
| 2008/0075720 A1 | 3/2008 | Holers et al. | |
| 2008/0102040 A1 | 5/2008 | Holers et al. | |
| 2008/0267980 A1 | 10/2008 | Tomlinson et al. | |
| 2008/0299114 A1 | 12/2008 | Emlen et al. | |
| 2009/0175847 A1 | 7/2009 | Barghorn et al. | |
| 2011/0163412 A1 | 7/2011 | Park | |
| 2011/0318337 A1 | 12/2011 | Emlen et al. | |
| 2012/0171206 A1 | 7/2012 | Tomlinson et al. | |
| 2013/0029912 A1 | 1/2013 | Holers et al. | |

FOREIGN PATENT DOCUMENTS

| | | |
|---|---|---|
| CA | 1340879 A | 1/2000 |
| WO | 9942133 | 8/1999 |
| WO | WO-99/42133 A1 | 8/1999 |
| WO | 0021559 | 4/2000 |
| WO | WO-00/21559 A2 | 4/2000 |
| WO | 0147963 | 7/2001 |
| WO | WO-01/47963 A2 | 7/2001 |
| WO | 2004103288 | 2/2004 |
| WO | 2004022096 | 3/2004 |
| WO | WO-2004/022096 A1 | 3/2004 |
| WO | WO-2004/031240 A1 | 4/2004 |
| WO | WO-2004/103288 A2 | 12/2004 |
| WO | WO-2004/106369 A2 | 12/2004 |
| WO | WO-2004/106369 A3 | 12/2004 |

(Continued)

OTHER PUBLICATIONS

Pelosi et al. (Chest, 2008, 134:101-108).*

(Continued)

*Primary Examiner* — Sharon Wen

(74) *Attorney, Agent, or Firm* — Clark & Elbing LLP; Kristina Bieker-Brady; Todd Armstrong

(57) ABSTRACT

Disclosed is the use of agents and compositions that selectively inhibit the alternative complement pathway for the inhibiting or treating physiological damage resulting from traumatic brain injury (TBI), spinal cord injury (SCI), or related conditions. Preferred reagents for use in inhibition of damage resulting from TBI or SCI include those that inhibit factor B, with anti-factor B antibodies representing a particularly preferred agent.

25 Claims, 15 Drawing Sheets

(56) References Cited

FOREIGN PATENT DOCUMENTS

| WO | WO-2005/003159 A1 | 1/2005 |
|---|---|---|
| WO | WO-2005/023195 A2 | 3/2005 |
| WO | WO-2005/023195 A3 | 3/2005 |
| WO | 2005077417 | 8/2005 |
| WO | WO-2005/069970 A2 | 8/2005 |
| WO | WO-2005/077417 A1 | 8/2005 |
| WO | WO-2006/012621 A1 | 2/2006 |
| WO | WO-2006/012621 A2 | 2/2006 |
| WO | WO-2006/012621 A3 | 2/2006 |
| WO | WO-2006-055178 A2 | 5/2006 |
| WO | WO-2006/062716 A2 | 6/2006 |
| WO | WO-2006/062716 A3 | 6/2006 |
| WO | WO-2006/083533 A2 | 8/2006 |
| WO | WO-2006/083533 A3 | 8/2006 |
| WO | WO-2006-122257 A2 | 11/2006 |
| WO | WO-2006/122257 A2 | 11/2006 |
| WO | WO-2006-122257 A3 | 11/2006 |
| WO | WO-2007/011363 A2 | 1/2007 |
| WO | WO-2007/011363 A3 | 1/2007 |
| WO | WO-2007/029008 A2 | 3/2007 |
| WO | WO-2007/029008 A3 | 3/2007 |
| WO | WO-2007/032876 A2 | 3/2007 |
| WO | WO-2007/032876 A3 | 3/2007 |
| WO | WO-2007/056227 A2 | 5/2007 |
| WO | WO-2007/056227 A3 | 5/2007 |
| WO | WO-2008/140653 A2 | 11/2008 |
| WO | WO-2008/140653 C1 | 11/2008 |
| WO | WO-2011-057158 A1 | 5/2011 |
| WO | WO-2011-143637 A1 | 11/2011 |
| WO | WO-2011-163412 A1 | 12/2011 |
| WO | WO-2013/177035 A2 | 11/2013 |

OTHER PUBLICATIONS

International Preliminary Report on Patentability for International (PCT) Patent Application No. PCT/US2006/020460 mailed Dec. 13, 2007.
Thurman et al. Molecular Immunology (2005) 42:87-97.
Glovsky et al. Annals of Allergy, Asthma and Immunology (2004) 93:6 pp. 513-523 & 605.
Girardi et al. J. Clinical Investigation (2003) 112:11, pp. 1644-1654.
Thurman et al., A Novel Inhibitor of the Alternative Pathway of Complement Protects Mice from Ischemic Acute Renal Failure. Abst. Oct. 2004, American Nephrology Society Meeting, 1 page.
Thurman et al. Abst. #254, Molecular Immunology 41 (2004), 1 page.
Thurman et al. Abst. #256, Molecular Immunology 41 (2004), p. 319.
Effect of Intravenous Corticosteroids on Death Within 14 Days in 10 008 Adults With Clinically Significant Head Injury (MRC Crash Trial): Randomised Placebo-Controlled Trial. www.thelancet.com. vol. 364, Oct. 9, 2004, pp. 1321-1328.
Vos, P.E. et al., "EFNS Guideline on Mild Traumatic Brain Injury: Report of an EFNS Task Force." European Journal of Neurology 2002, 9: 207-219.
Elf, K., et al. "Prevention of Secondary Insults in Neurointensive Care of Traumatic Brain Injury." European Journal of Trauma 2003. No. 2 pp. 74-80.
Royo, NC., et al. "Pharmacology of Traumatic Brian Injury." Current Opinion in Pharmacology 2003, 3:37-32.
Ghajar, J., "Traumatic Brain Injury." The Lancet. vol. 356. Sep. 9, 2000, pp. 923-929.
Dutton, R.P., et al. "Traumatic Brain Injury." Current Opinion in Critical Care 2003, 9:503-509.
Gaetz. M., "The Neurophysiology of Brain Injury." Clinical Neurophysiology 115 (2004) 4-18.
"A CRASH Landing in Severe Head Injury." www.thelancet.com. vol. 364, Oct. 9, 2004. pp. 1291-1292.
Kossman, T. et al., "Elevated Levels of the Complement Complement C3 and Factor B in Ventricular Cerebrospinal Fluid of Patients with Traumatic Brain Injury." Journal of Neuroimmunology 73 (1997) 63-69.
Keeling, K.L., et al. Local Neutrophil Influx Following Lateral Fluid-Percussion Brain Injury in Rats is Associated with Accumulation of Complement Activation Fragments of the Third Component (C3) of the Complement System. Journal of Neuroimmunology 105 (2000) 20-30.
International Search Report and Written Opinion dated Aug. 29, 2006 for International Application PCT/US06/20460.
Abass, A.K. et al. eds. (1991). *Cellular and Molecular Immunology*, W.B. Saunders Company: Philadelphia, PA, pp. 54.
Alexander, J.J. et al. (2005). "Complement-Dependent Apoptosis and Inflammatory Gene Changes in Murine Lupus Cerebritis," *J. Immunol.* 175:8312-8319.
Anderson, A.J. et al. (2004). "Activation of Complement Pathways after Contusion-Induced Spinal Cord Injury," *J. Neurotrauma* 21(12):1831-1846.
Anonymous. (Date Unknown). "Monoclonal Antibody to Human Factor B (Ba), Catalog No. A225" in *Quidel Corporation Product Catalog*, located at <http://www.quidel.com/products/product_detail.php?prod=82&group=2>, last visited on Aug. 4, 2008, two pages.
Anonymous. (Date Unknown). "Monoclonal Antibody to Human Factor B (Bb), Catalog No. A227," in *Quidel Corporation Product Catalog*, located at <http://www.quidel.com/products/product_detail.php?group=2&prod=83>, last visited on Aug. 4, 2008, two pages.
Attwood, T.K. (Oct. 20, 2000). "The Babel of Bioinformatics," *Science* 290:471-473.
Barnum, S.R. (1999). "Inhibition of Complement as a Therapeutic Approach in Inflammatory Central Nervous System (CNS) Disease," *Mol. Med.* 5:569-582.
Bellander, B-M. et al. (Sep. 1996). "Activation of the Complement Cascade and Increase of Clusterin in the Brain Following a Cortical Contusion in the Adult Rat," *J. Neurosurg.* 85:468-475.
Bellander, B-M. et al. (2001). "Complement Activation in the Human Brain after Traumatic Head Injury," *J. Neurotrauma* 18(12):1295-1311.
Bendayan, M. (1995). "Possibilities of False Immunocytochemical Results Generated by the Use of Monoclonal Antibodies: The Example of the Anti-proinsulin Antibody," *J. Histochem. Cytochem.* 43(9):881-886.
Bendig, M.M. (1995). "Humanization of Rodent Monoclonal Antibodies by CDR Grafting," *Methods: A Companion to Methods in Enzymology* 8:83-93.
Boos, L.A. et al. (2004, e-pub. Jul. 6, 2004). "Murine Complement C4 is Not Required for Experimental Autoimmune Encephalomyelitis," *Glia* 49:158-160.
Bost, K.L. et al. (1988). "Antibodies Against a Peptide Sequence Within the HIV Envelope Protein Crossreacts with Human Interleukin-2," *Immunological Investigation* 17(6&7):577-586.
Caldas, C. et al. (2003). "Humanization of the Anti-CD18 Antibody 6.7: An Unexpected Effect of a Framework Residue in Binding to Antigen," *Molecular Immunology* 39:941-952.
Casarsa, C. et al. (2003). "Intracerbroventricular Injection of the Terminal Complement Complex Causes Inflammatory Reaction in the Rat Brain," *Eur. J. Immunol.* 33:1260-1270.
Chardès, T. et al. (1999). "Efficient Amplification and Direct Sequencing of Mouse Variable Regions from any Immunoglobulin Gene Family," *FEBS Lett.* 452(3):386-394.
Chen, Y. et al. (1996). "An Experimental Model of Closed Head Injury in Mice: Pathophysiology, Histopathology, and Cognitive Deficits," *J. Neurotrauma* 13(10):557-568.
Chien, N.C. et al. (Jul. 1989). "Significant Structural and Functional Change of an Antigen-Binding Site by a Distant Amino Acid Substitution: Proposal of a Structural Mechanism," *Proc. Natl. Acad. Sci. USA* 86:5532-5536.
Choi, W.S. et al. (Sep. 25, 2001). "Inhalation Delivery of Proteins from Ethanol Suspensions," *Proc. Natl. Acad. Sci.* 98(20):11103-11107.
Clardy, C.W. et al. (Apr. 1992). "In vitro Inhibition of Complement Activation Using a Monoclonal Antibody (McAb) Directed Against Human Factor B (FB)," *Pediatric Res.* 31(4):331A, Abstract No. 1969.

(56) References Cited

OTHER PUBLICATIONS

Clardy, C.W. et al. (Oct. 1994). "Complement Activation by Whole Endotoxin Is Blocked by a Monoclonal Antibody to Factor B," *Infect. Immunity* 62(10):4549-4555.

Cole, D.S. et al. (2003). "Beyond lysis: How Complement Influences Cell Fate," *Clin. Sci.* 104:455-466.

Cole, D.S. et al. (2006, e-pub. Jan. 10, 2006). "Complement Regulator Loss on Apoptotic Neuronal Cells Causes Increased Complement Activation and Promotes Both Phagocytosis and Cell Lysis," *Mol. Immunol.* 43:1953-1964.

Daha, M.R. et al. (May 1984). "Stabilization of the Amplification Convertase of Complement by Monoclonal Antibodies Directed Against Human Factor B," *Infect. Immun.* 132(5):2538-2542.

Declaration of Joshua M. Thurman mailed on Apr. 16, 2008, for U.S. Appl. No. 11/057,047, filed Feb. 10, 2005, 3 pages.

Elward, K. et al. (Oct. 28, 2005). "CD46 Plays a Key Role in Tailoring Innate Immune Recognition of Apoptitic and Necrotic Cells," *J. Biol. Chem.* 280(43):36342-36354.

Eldadah, B.S. et al. (2000). "Caspase Pathways, Neuronal Apoptosis, and CNS Injury," *J. Neurotrauma* 17(10):811-829.

European Office Action mailed on Oct. 27, 2010, for European Patent Application No. 08794326.2, filed on Sep. 11, 2009, 7 pages.

Extended European Search Report mailed on Oct. 28, 2010, for European Patent Application No. 10164673.5, filed on Sep. 11, 2009, 10 pages.

Farkas, I. et al. (1998). "A Neuronal C5a Receptor and an Associated Apoptotic Signal Transduction Pathway," *J. Physiol.* 507(3):679-687.

Felderhoff-Mueser, U. et al. (2002). "Pathways Leading to Apoptotic Neurodegeneration Following Trauma to the Developing Rat Brain," *Neurobiol. Dis.* 11:231-245.

Figueroa, J.E. et al. (Apr. 1991). "Infectious Diseases Associated with Complement Deficiencies," *Clin. Microbiol. Rev.* 4(3):359-395.

Friedlander, R.M. (Apr. 3, 2003). "Apoptosis and Caspases in Neurodegenerative Diseases," *N. Engl. J. Med.* 348(14):1365-1375.

Gilkeson, G.S. (Date Unknown). "NIH Research Portfolio Online Reporting Tools. Project Number: 5R01A1047469-05," located at <http://projectreporter.nih.gov/pr_Prj_info_desc_dtls.cfm?icde=0&aid=6712799&print=yes>, last visited on Apr. 25, 2011, 2 pages.

Girardi, G. et al. (Feb. 2004). "Complement C5a Receptors and Neutrophils Mediate Fetal Injury in the Antiphospholipid Syndrome," *J. Clin. Invest.*, Corrigendum, 113(4):646.

Giusti, A.M. et al. (May 1987). "Somatic Diversification of S107 from an Antiphosphocholine to an Anti-DNA Autoantibody is Due to a Single Base Change in its Heavy Chain Variable Region," *Proc. Natl. Acad. Sci. USA* 84:2926-2930.

Hall, R.E. (Sep. 1982). "Cooperative Interaction of Factor B and Other Complement Components with Mononuclear Cells in the Antibody-Independent Lysis of Xenogeneic Erythrocytes," *J. Exp. Med.* 156:834-843.

Hicks, R.R. et al. (2002). "Vaccinia Virus Complement Control Protein Enhances Functional Recovery after Traumatic Brian Injury," *J. Neurotrauma* 19(6):705-714.

Holers, V.M. (2000). "Phenotypes of Complement Knockouts," *Immunopharmacology* 49:125-131.

Holers, V.M. (2003). "The Complement System as a Therapeutic Target in Autoimmunity," *Clin. Immunol.* 107:140-151.

Holers, V.M. et al. (2004). "The Alternative Pathway of Complement in Disease: Opportunities for Therapeutic Targeting," *Molecular Immunology* 41:147-152.

Holm, P. et al. (2007). "Functional Mapping and Single Chain Construction of the Anti-Cytokeratin 8 Monoclonal Antibody TS1," *Molecular Immunology* 44:1075-1084.

Hourcade, D.E. et al. (Aug. 25, 1995). "Analysis of the Short Consensus Repeats of Human Complement Factor B by Site-directed Mutagenesis," *J. Bio. Chem.* 270(34):19716-19722.

International Preliminary Report on Patentability mailed on Jul. 7, 2005, for PCT Application No. PCT/US2005/004346, filed on Feb. 10, 2005, 4 pages.

International Preliminary Report on Patentability mailed on Sep. 24, 2009, for PCT Application No. PCT/US2008/003381, filed on Mar. 14, 2008, 9 pages.

International Search Report mailed on Jul. 7, 2005, for PCT Application No. PCT/US05/04346, filed on Feb. 10, 2005, 2 pages.

International Search Report mailed on Feb. 11, 2009, for PCT Application No. PCT/US2008/003381, filed on Mar. 14, 2008, 6 pages.

Interview Summary mailed on Apr. 16, 2008, for U.S. Appl. No. 11/057,047, filed Feb. 10, 2005, 4 pages.

Kaczorowski, S.L. et al. (1995). "Effect of Soluble Complement Receptor-1 on Neutrophil Accumulation After Traumatic Brain Injury in Rats," *J. Cereb. Blood Flow Metab.* 15(5):860-864.

Kang, B.H.J. et al. (2000). "A Novel Anti-Human Factor B Monoclonal Antibody Inhibits Factor D-Mediated Associated and Cleavage of Factor B," Abstract No. 191, *Immunopharmacology* 49(1-2):68.

Kolb, W.P. et al. (1989). "Ba and Bb Fragments of Factor B Activation: Fragment Production, Biological Activities, Neoepitope Expression and Quantitation in Clinical Samples," *Complement & Inflammation* 6:175-204.

Kurucz, I. et al. (2006). "Current Animal Models of Bronchial Asthma," *Current Pharmaceutical Design* 12:3175-3194.

Kuttner-Kondo, L.A. et al. (2001). "Characterization of the Active Sites in Decay-Accelerating Factor," *Journal of Immunology* 167:2164-2171.

Kyrkanides, S. et al. (2001). "Enhanced Glial Activation and Expression of Specific CNS Inflammation-Related Molecules in Aged Versus Young Rats Following Cortical Stab Injury," *J. Neuorimmunol.* 119:269-277.

Lederman, S. et al. (1991). "A Single Amino Acid Substitution in a Common African Allele of the CD4 Molecule Ablates Binding of the Monoclonal Antibody, OKT4," *Molecular Immunology* 28(11):1171-1181.

Leinhase, I. et al. (2006, e-pub. Mar. 20, 2006). "Pharmacological Complement Inhibition at the C3 Convertase Level Promotes Neuronal Survival, Neuroprotective Intracerebral Gene Expression, and Neurological Outcome After Traumatic Brain Injury," *Exp. Neurol.* 199:454-464.

Lemanske, R.F. Jr. (2009). "Asthma Therapies Revisited. What Have We Learned?" *Proc. Am. Thorac. Soc.* 6:312-315.

Li, C.H. et al. (Jun. 1980). "β-Endorphin Omission Analogs: Dissociation of Immunoreactivity from Other Biological Activites," *Proc. Natl. Acad. Sci. USA* 77(6):3211-3214.

MacCallum, R. M. (1996). "Antibody-Antigen Interactions: Contact Analysis and Binding Site Topography," *J. Mol. Biol.* 262:732-745.

Marciano, P.G. et al. (Mar. 24, 2004). "Neuron-Specific mRNA Complexity Responses During Hippocampal Apoptosis after Traumatic Brain Injury," *J. Neurosci.* 24(12):2866-2876.

Mariuzza, R.A. et al. (1987). "The Structural Basis of Antigen-Antibody Recognition," *Annu. Rev. Biophys. Biphys. Chem.* 16:139-159.

Marshall, L.F. et al. (Nov. 1991). "A New Classification of Head Injury Based on Computerized Tomography," *J. Neurosurg.* 75:S14-S20.

Matsumoto, M. et al. (Aug. 1997). "Abrogation of the Alternative Complement Pathway by Targeted Deletion of Murine Factor B," *Proc. Natl. Acad. Sci. USA* 94:8720-8725.

Maulik, S. et al. (1997). *Molecular Biotechnology: Therapeutic Applications and Strategies*, Wiley-Liss, Inc., pp. v-viii (Table of Contents Only.).

McArthur, D.L. et al. (2004). "Moderate and Severe Traumatic Brain Injury: Epidemiologic, Imaging and Neuropathologic Perspectives," *Brain Pathol.* 14:185-194.

Mohamad, N. et al. (2005). "Mitochondrial Apoptotic Pathways," *Biocell* 29(2):149-161.

Morgan, P. et al. (Oct. 1996). "Expression of Complement in the Brain: Role in Health and Disease," *Immunol. Today* 17(10):461-466.

Morgan, B.P (1999). "Regulation of the Complement Membrane Attack Pathway," *Crit. Rev. Immunol.* 19(3):173-198.

Nataf, S. et al. (1999). "Complement Anaphylatoxin Receptors on Neurons: New Tricks for Old Receptors?" *Trends Neurosci.* 22(9):397-402.

(56) References Cited

OTHER PUBLICATIONS

Nataf, S. et al. (2000). "Attenuation of Experimental Autoimmune Demyelination in Complement-Deficient Mice," *J. Immunol.* 165:5867-5873.
Non-Final Office Action mailed on Oct. 19, 2007, for U.S. Appl. No. 11/057,047, filed Feb. 10, 2005, 4 pages.
Non-Final Office Action mailed on Apr. 30, 2009, for U.S. Appl. No. 11/057,047, filed Feb. 10, 2005, 12 pages.
Non-Final Office Action mailed on Aug. 16, 2010, for U.S. Appl. No. 12/049,233, filed Mar. 14, 2008, 28 pages.
Non-Final Office Action mailed on Oct. 7, 2010, for U.S. Appl. No. 11/843,617, filed Aug. 22, 2007, 11 pages.
Non-Final Office Action mailed on Oct. 13, 2010, for U.S. Appl. No. 11/057,047, filed Feb. 10, 2005, 8 pages.
Non-Final Office Action mailed on Nov. 29, 2010, for U.S. Appl. No. 11/888,997, filed Aug. 3, 2007, 15 pages.
Notice of Allowance mailed on Feb. 15, 2011, for U.S. Appl. No. 12/049,233, filed on Mar. 14, 2008, 10 pages.
O'Barr, S.A. et al. (2001). "Neuronal Expression of a Functional Receptor for the C5a Complement Activation Fragment," *J. Immunol.* 166:4154-4162.
Ohlsson, M. et al. (2003). "Complement Activation Following Optic Nerve Crush in the Adult Rat," *J. Neurotrauma* 20(9):895-904.
Ohlsson, M. et al. (2006, e-pub. Nov. 11, 2005). "Complement Activation After Lumbosacral Ventral Root Avulsion Injury," *Neurosci. Lett.* 392:179-183.
Padlan, E.A. et al. (Aug. 1989). "Structure of an Antibody-Antigen Complex: Crystal Structure of the HyHEL-10 Fab-Lysozyme Complex," *Proc. Natl. Acad. Sci.* 86:5938-5942.
Peters, M.G. (Oct. 1988). "The Bb Fragment of Complement Factor B Acts as a B Cell Growth Factor," *J. Exp. Med.* 168:1225-1235.
Pillay, N.S. et al. (2005). "Administration of Vaccinia Virus Complement Control Protein Shows Significant Cognitive Improvement in a Mild Injury Model," *Ann. NY Acad. Sci.* 1056:450-461.
Qiu, J. et al. (May 1, 2002). "Upregulation of the Fas Receptor Death-Inducing Signaling Complex After Traumatic Brain Injury in Mice and Humans," *J. Neurosci.* 22(9):3504-3511.
Raghupathi, R. et al. (Nov. 1998). "BCL-2 Overexpression Attenuates Cortical Cell Loss After Traumatic Brain Injury in Transgenic Mice," *J. Cereb. Blood Flow Metab.* 18(11):1259-1269.
Raghupathi, R. et al. (2002). "Mild Traumatic Brain Injury Induces Apoptotic Cell Death in the Cortex that Is Preceded by Decreases in Cellular Bcl-2 Immunoreactivity," *Neuroscience* 110(4):605-616.
Raghupathi, R. et al. (May 2003). "Temporal Alterations in Cellular Bax:Bcl-2 Ratio Following Traumatic Brain Injury in the Rat," *J. Neurotrauma* 20(5):421-435.
Raghupathi, R. (2004). "Cell Death Mechanisms Following Traumatic Brain Injury," *Brain Pathol.* 14:215-222.
Ramer, L.M. et al. (2005, e-pub. Jan. 25, 2005). "Setting the Stage for Functional Repair of Spinal Cord Injuries: A Cast of Thousands," *Spinal Cord* 43(3):134-161.
Rancan, M. et al. (2003). "Central Nervous System—Targeted Complement Inhibition Mediates Neuroprotection After Closed Head Injury in Transgenic Mice," *J. Cereb. Blood Flow & Metab.* 23(9):1070-1074.
Rebhun, J. et al. (Apr. 1991). "Proteins of the Complement System and Acute Phase Reactants in Sera of Patients with Spinal Cord Injury," *Ann. Allergy* 66(4):335-338.
Reynolds, D.N. et al. (2004). "Vaccinia Virus Complement Control Protein Reduces Inflammation and Improves Spinal Cord Integrity Following Spinal Cord Injury," *Ann. NY Acad. Sci.* 1035:165-178.
Rink, A. et al. (Dec. 1995). "Evidence of Apoptotic Cell Death After Experimental Traumatic Brain Injury in the Rat," *Am. J. Pathol.* 147(6):1575-1583.
Roof, R.L. (May 2000). "Gender Differences in Acute CNS Trauma and Stroke: Neuroprotective Effects of Estrogen and Progesterone," *J. Neurotrauma* 17(5):367-388.
Rudikoff, S. et al. (Mar. 1982). "Single Amino Acid Substitution Altering Antigen-Binding Specificity," *Proc. Natl. Acad. Sci. USA* 79:1979-1983.

Sambrook, J. et al. (1989). "*Analysis of Genomic DNA by Southern Hybridization*," in *Molecular Cloning: A Laboratory Manual*, Second Edition, Cold Spring Harbor Labs Press: Cold Spring Harbor, NY, pp. 9.31-9.62.
Schacka, J.J. et al. (2005). "Regulation of Neuronal Cell Death and Neurodegeneration by Members of the Bcl-2 Family: Therapeutic Implications," *Curr. Drug Targets CNS Nuerol. Disord.* 4(1):25-39.
Schmidt, O.I. et al. (Jun. 2004). "The Role of Neuroinflammation in Traumatic Brain Injury," *Eur. J. Trauma* 30(3):135-149.
Schmidt, O.I. et al. (2005, e-pub. Jan. 28, 2005). "Closed Head Injury—An Inflammatory Disease?" *Brain Res. Rev.* 48:388-399.
Sewell, D.L. et al. (2004). "Complement C3 and C5 Play Critical Roles in Traumatic Brain Cryoinjury: Blocking Effects on Neutrophil Extravasation by C5a Receptor Antagonist," *J. Neuroimmunol.* 155:55-63.
Singhrao, S.K. et al. (Sep. 2000). "Spontaneous Classical Pathway Activation and Deficiency of Membrane Regulators Render Human Neurons Susceptible to Complement Lysis," *Am. J. Pathol.* 157(3):905-918.
Skolnick, J. et al. (Jan. 2000). "From Genes to Protein Structure and Function: Novel Applications of Computational Approaches in the Genomic Era," *Trends in Biotechnology* 18:34-39.
Stahel, P.F. et al. (1998). "The Role of the Complement System in Traumatic Brian Injury," *Brian Res. Rev.* 27:243-256.
Stahel, P.F. et al. (2000). "Experimental Closed Head Injury: Analysis of Neurological Outcome, Blood-Brain Barrier Dysfunction, Intracranial Neutrophil Infiltration, and Neuronal Cell Death in Mice Deficient in Genes for Pro-Inflammatory Cytokines," *J. Cereb. Blood Flow Metab.* 20:369-380, 19 pages total.
Stahel, P.F. et al. (2000). "Intracerebral Complement C5a Receptor (CD88) Expression is Regulated by TNF and Lyphotoxin-α Following Closed Head Injury in Mice," *J. Neuroimmunol.* 109:164-172.
Stahel, P.F. et al. (Aug. 2001). "Intrathecal Levels of Complement-Derived Soluble Membrane Attack Complex (sC5b-9) Correlate with Blood-Brain Barrier Dysfunction in Patients with Traumatic Brian Injury," *J. Neurotrauma* 18(8):773-781.
Strauss, K.I. et al. (2004). "Common Patterns of Bcl-2 Family Gene Expression in Two Traumatic Brain Injury Models," *Neurotox. Res.* 6(4):333-342.
Stribling, R. et al. (Dec. 1992). "Aerosol Gene Delivery In Vivo," *Proc. Natl. Acad. Sci. USA* 89:11277-11281.
Supplementary Partial European Search Report mailed on Jul. 7, 2008, for EP Application No. 05722948.6, filed on Feb. 10, 2005, 7 pages.
Takahashi, M. (1980). "Solubilization of Antigen-Antibody Complexes: A New Function of Complement as a Regulator of Immune Reactions," *Prog. Allergy* 27:134-166.
Tanaka, E. et al. (Jan. 1, 1991). "Murine Monoclonal Anti-Ba Antibody that Enhances Haemolytic Activity of Factor B," *Immunol.* 73(4):383-387.
Tatusova, T.A. et al. (May 15, 1999). "BLAST 2 Sequences, a New Tool for Comparing Protein and Nucleotide Sequences," *FEMS Microbiol. Lett.* 174(2):247-250.
Taube, C. et al. (May 23, 2006). "Factor B of the Alternative Complement Pathway Regulates Development of Airway Hyperresponsiveness and Inflammation," *Proc. Natl. Acad. Sci. USA* 103(21):8084-8089.
Teasdale, G. et al. (Jul. 13, 1974). "Assessment of Coma and Impaired Consciousness," *Lancet* 2(7872):81-84.
Thurman, J.M. et al. (Feb. 1, 2003). "Lack of Functional Alternative Complement Pathway Ameliorates Ischemic Acute Renal Failure in Mice," *J. Immunol.* 170(3):1517-1523.
Thurman, J.M. et al. (2005). "Acute Tubular Necrosis is Characterized by Activation of the Alternative Pathway of Complement," *Kidney Int.* 67:524-530.
Thurman, J.M. et al. (2006). "Treatment with an Inhibitory Monoclonal Antibody to Mouse Factor B Protects Mice from Induction of Apoptosis and Renal Ischemia/Reperfusion Injury," *J. Am. Soc. Nephrol.* 17:705-715.
Thurman, J.M. et al. (2006). "The Central Role of the Alternative Complement Pathway in Human Disease," *J. Immunol.* 176:1305-1310.

(56) References Cited

OTHER PUBLICATIONS

Ueda, A. et al. (Feb. 15, 1987). "Probing Functional Sites on Complement Protein B with Monoclonal Antibodies: Evidence for C3b-Binding Sites on Ba," *J. Immunology* 138(4):1143-1149.

Van Beek, J. et al. (2003). "Activation of the Complement in the Central Nervous System. Roles in Neurodegeneration and Neuroprotection," *Ann. NY Acad. Sci.* 992:56-71.

Watanabe, H. et al. (2000). "Modulation of Renal Disease in MRL/lpr Mice Genetically Deficient in Alternative Complement Pathway Factor B," *J. Immunol.* 164:786-794.

Williams, S. et al. (2001, e-pub. Oct. 9, 2001). "In situ DNA Fragmentation Occurs in White Matter up to 12 Months After Head Injury in Man," *Acta Neuropathol.* 102:581-590.

Wong, J. et al. (2005). "Apoptosis and Traumatic Brian Injury," *Neurocrit. Care* 3:177-182.

Written Opinion of the International Searching Authority mailed on Aug. 29, 2006, for PCT Patent Application No. PCT/US2006/020460, filed on May 26, 2006, 4 pages.

Written Opinion of the International Searching Authority mailed on Feb. 11, 2009, for PCT Application No. PCT/US2008/003381, filed on Mar. 14, 2008, 7 pages.

Xiong, Z-Q. et al. (Feb. 1, 2003). "Formation of Complement Membrane Attack Complex in Mammalian Cerebral Cortex Evokes Seizures and Neurodegeneration," *J. Neurosci.* 23(3):955-960.

Xu, Y. et al. (1997). "Contribution of the Complement Control Protein Modules of C2 in C4b Binding Assessed by Analysis of C2/Factor B Chimeras," *J. Immunol.* 158:5958-5965.

Yakovlev, A.G. et al. (Oct. 1, 1997). "Activation of CPP32-Like Caspases Contributes to Neuronal Apoptosis and Neurological Dysfunction After Traumatic Brain Injury," *J. Neurosci.* 17(19):7415-7424.

Yao, X-L. et al. (2005). "Progesterone Differentially Regulates Pro- and Anti-Apoptotic Gene Expression in Cerebral Cortex Following Traumatic Brain Injury in Rats," *J. Neurotrauma* 22(6):656-668.

Yatsiv, I. et al. (2002). "Elevated Intracranial IL-18 in Humans and Mice After Traumatic Brain Injury and Evidence of Neuroprotective Effects of IL-18-Binding Protein After Experimental Closed Head Injury," *J. Cereb. Blood Flow Metab.* 22(8):971-978.

Yatsiv, I. et al. (2005, e-pub. Aug. 12, 2005). "Erythropoietin is Neuroprotective, Improves Functional Recovery, and Reduces Neuronal Apoptosis and Inflammation in a Rodent Model of Experimental Closed Head Injury," *FASEB J.*, 20 pages.

Zhang, X. et al. (Feb. 2005, e-pub. Sep. 3, 2004). "Bench-to-Bedside Review: Apoptosis/Programmed Cell Death Triggered by Traumatic Brain Injury," *Crit. Care.* 9(1):66-75.

Kulkarni, A.P. et al. (2004). "Neuroprotection from Complement-Mediated Inflammatory Damage," *Annals of the New York Academy of Sciences* 1035:147-164.

Supplementary European Search Report mailed on Nov. 24, 2011, for EP Application No. 06771303.2, filed on May 26, 2006, 12 pages.

Becherer et al., "Segment spanning residues 727-768 of the complement C3 sequence contains a neoantigenic site and accommodates the binding of CR1, factor H, and factor B," *Biochemistry* 31:1787-1794, 1992.

CRASH trial collaborators, "Effect of intravenous corticosteroids on death within 14 days in 10008 adults with clinically significant head injury (MRC CRASH trial): randomised placebo-controlled trial," *Lancet* 364: 1321-1328, 2004.

Extended European Search Report for European Application No. EP10188613.3, dated May 31, 2011 (10 pages).

International Preliminary Report on Patentability and Written Opinion for International Application No. PCT/US2006/020460, dated Nov. 30, 2007 (5 pages).

Sauerland and Maegele, "A CRASH landing in severe head injury," *Lancet* 364: 1291-1292, 2004.

Shacka and Roth, "Regulation of neuronal cell death and neurodegeneration by members of the Bcl-2 family: therapeutic implications," *Curr. Drug Targets CNS Neurol. Disord.* 4: 25-39, 2005.

Versey et al., "Activation of complement in relation to disease," *J. Clin. Path. Suppl.* 28: 38-44, 1975.

Written Opinion of the International Searching Authority for International Application No. PCT/US2005/004346, dated Jul. 7, 2005 (3 pages).

Brandis, K. (Date Unknown). "Acid-Base Physiology," located at <http://www.anaesthesiamcq.com/AcidBaseBook/ab4_4.php>, last visited on Sep. 19, 2011, 2 pages.

De Broe, M.E. et al. (1989). "Pathophysiology of Hemodialysis-Associated Hypoxemia," *Adv. Nephrol. Necker Hosp.* 18:297-315, Abstract Only.

Final Office Action mailed on Jun. 21, 2011, for U.S. Appl. No. 11/843,617, filed Aug. 22, 2007, 11 pages.

Final Office Action mailed on Aug. 22, 2011, for U.S. Appl. No. 11/888,997, filed Aug. 3, 2007, 15 pages.

German, J.W. et al. (Jul. 1996). "Systemic Complement Depletion Inhibits Experimental Cerebral Vasospasm," *Neurosurgery* 39(1):141-145, discussion 145-146, Abstract Only.

Jaeschke, H. et al. (2006). "Role of Neutrophils in Acute Inflammatory Liver Injury," *Liver International* 26:912-919.

Leinhase, I. et al. (Jul. 14, 2006). "Reduced Neuronal Cell Death After Experimental Brian Injury in Mice Lacking a Functional Alternative Pathway of Complement Activation," *BMC Neuroscience* 7:55, 12 pages.

Notice of Allowance mailed on Apr. 5, 2011, for U.S. Appl. No. 11/057,047, filed Feb. 10, 2005, 7 pages.

Rood, P.P. et al. (Jan. 27, 2007). "Reduction of Early Graft Loss After Intraportal Porcine Islet Transplantation in Monkeys," *Transplantation* 83(2):202-210, Abstract Only.

Rounioja, S. et al. (Jun. 2005). "Mechanism of Acute Fetal Cardiovascular Depression After Maternal Inflammatory Challenge in Mouse," *Am. J. Pathol.* 166(6):1585-1592, Abstract Only.

Younger, J.G. et al. (2001). "Detrimental Effects of Complement Activation in Hemorrhagic Shock," *J. Appl. Physiol.* 90:441-446, Corrigenda (2004). *J. AppL Physiol.* 96:405.

Abe et al., "Contribution of anaphylatoxin C5a to late airway responses after repeated exposure of antigen to allergic rats," J Immunol. 167:4651-4660 (2001).

Abrahamsen et al., "Differential mediator release from basophils of allergic and non-allergic asthmatic patients after stimulation with anti-IgE and C5a," Clin Exp Allergy. 31:368-378 (2001).

Anderson et al., "Activation of complement pathways after contusion-induced spinal cord injury," J Neurotrauma. 21:1831-1846 (2004).

Bellander et al., "Activation of the complement cascade and increase of clusterin in the brain following a cortical contusion in the adult rat," J Neurosurg. 85:468-475 (1996).

Bellander et al., "Complement activation in the human brain after traumatic head injury," J Neurotrauma. 18:1295-1311 (2001).

Beste et al., "Small antibody-like proteins with prescribed ligand specificities derived from the lipocalin fold," Proc Natl Aced Sci USA. 96:1898-1903 (1999).

Bjornson et al., "Complement is activated in the upper respiratory tract during influenza virus infection," Am Rev Respir Dis. 143:1062-1066 (1991).

Blease et al., "Chemokines and their role in airway hyper-reactivity," Respir Res. 1:54-61 (2000).

Casale et al., "Direct evidence of a role for mast cells in the pathogenesis of antigen-induced bronchoconstriction," J Clin Invest. 80:1507-1511 (1987).

Casarsa et al., "Intracerebroventricular injection of the terminal complement complex causes inflammatory reaction in the rat brain," Eur J Immunol. 33:1260-1270 (2003).

Chaney, "Corticosteroids and cardiopulmonary bypass: A review of clinical investigations," Chest. 121:921-931 (2002).

Chen et al., "An experimental model of closed head injury in mice: pathophysiology, histopathology, and cognitive deficits," J. Neurotrauma 13: 557-568, 1996.

Cieslewicz et al., "The late, but not early, asthmatic response is dependent on IL-5 and correlates with eosinophil infiltration," J. Clin Invest. 104: 301-308, 1999.

(56) References Cited

OTHER PUBLICATIONS

Clardy, "Complement activation by whole endotoxin is blocked by a monoclonal antibody to factor B," Infect Immun. 62(10):4549-4555, 1994.
Clark, "Antibodies for therapeutic applications," <http://www.path.cam.ac.uk/~mrc7/humanisation/antibodies.html>, retrieved Jun. 1, 2002 (5 pages).
Collard et al., "Complement activation following oxidative stress," Mol Immunol. 36:941-948 (1999).
Czermak et al., "Complement, cytokines, and adhesion molecule expression in inflammatory reactions," Proc Assoc Am Physicians. 110(5):306-312 (1998).
Declaration of Vernon Michael Holers for U.S. Appl. No. 11/057,047, executed Aug. 31, 2009 (68 pages).
Desai et al., "Demonstration of C5 cleaving activity in bronchoalveolar fluids and cells: A mechanism of acute and chronic alveolitis," J Exp Pathol. 1(3):201-216 (1984).
Diaz et al., "Leukocytes and mediators in bronchoalveolar lavage during allergen-induced late-phase asthmatic reactions," Am Rev Respir Dis. 139:1383-1389 (1989).
Drouin et al., "A protective role for the fifth complement component (C5) in allergic airway disease," Am J Respir Crit Care Med. 173:852-857 (2006).
Drouin et al., "Expression of the complement anaphylatoxin C3a and C5a receptors on bronchial epithelial and smooth muscle cells in models of sepsis and asthma," J Immunol. 166:2025-2032 (2001).
Dutton et al., "Traumatic Brain Injury," Curr Opin Crit Care. 9:503-509 (2003).
Eldadah et al., "Caspase pathways, neuronal apoptosis, and CNS injury," J Neurotrauma 17:811-829 (2000).
Elf et al., "Prevention of secondary insults in neurointensive care of traumatic brain injury," Eur J of Trauma. 29:74-80 (2003).
Elward et al., "CD46 plays a key role in tailoring innate immune recognition of apoptotic and necrotic cells," J Biol Chem. 280:36342-36354 (2005).
Felderhoff-Mueser et al., "Pathways leading to apoptotic neurodegeneration following trauma to the developing rat brain," Neurobiol Dis. 11:231-245 (2002).
Figueroa et al., "Infectious diseases associated with complement deficiencies," Clin Microbiol Rev. 4:359-395 (1991).
Frank, "Complement: A brief review," J Allergy Clin Immunol. 84:411-420 (1989).
Friedlander, "Apoptosis and caspases in neurodegenerative diseases," N Engl J Med. 348:1365-1375 (2003).
Gaetz, "The neurophysiology of brain injury," Clin Neurophysiology. 115:4-18 (2004).
Gerard et al., "Complement in allergy and asthma," Curr Opin Immunol. 14:705-708 (2002).
Ghajar, "Traumatic brain injury," Lancet. 356:923-929 (2000).
Glovsky et al., "Is complement activation a factor in bronchial asthma?" Int Arch Allergy Immunol. 118:330-332 (1999).
Gönczi et al., "The severity of clinical symptoms in ragweed-allergic patients is related to the extent of ragweed-induced complement activation in their sera," Allergy. 52:1110-1114 (1997).
Hawlisch et al., "The anaphylatoxins bridge innate and adaptive immune responses in allergic asthma," Mol Immunol. 41:123-131 (2004).
Hicks et al., "Vaccinia virus complement control protein enhances functional recovery after traumatic brain injury," J. Neurotrauma. 19:705-714 (2002).
Hogaboam et al., "Mannose-binding lectin deficiency alters the development of fungal asthma: Effects on airway response, inflammation, and cytokine profile," J Leukoc Biol. 75:805-814 (2004).
Holgate et al., "The bronchial epithelium as a key regulator of airway inflammation and remodelling in asthma," Clin Exp Allergy. 29:90-95 (1999).
Hourcade et al., "Analysis of the short consensus repeats of human complement factor B by site-directed mutagenesis," J. Biol. Chem. 270(34): 19716-19722, 1995.

Hourcade et al., "Mutations of the type A domain of complement factor B that promote high-affinity C3b-binding," J. Immunol. 162: 2906-2911, 1999.
Humbles et al., "A role for the C3a anaphylatoxin receptor in the effector phase of asthma," Nature 406:998-1001 (2000).
Höpken et al., "The C5a chemoattractant receptor mediates mucosal defence to infection," Nature. 383:86-89 (1996).
International Search Report mailed on Aug. 29, 2006, for International Application No. PCT/US2006/020460, filed on May 26, 2006 (3 pages).
Irvin et al., "Airways hyperreactivity and inflammation produced by aerosolization of human C5A des arg$^{1-3}$," Am Rev Respir Dis. 134:777-783 (1986).
Jagels et al., "C3a and C5a enhance granulocyte adhesion to endothelial and epithelial cell monolayers: Epithelial and endothelial priming is required for C3a-induced eosinophil adhesion," Immunopharmacology. 46:209-222 (2000).
Karp et al., "Identification of complement factor 5 as a susceptibility locus for experimental allergic asthma," Nat Immunol. 1(3):221-226 (2000).
Kasamatsu et al., "Experimental acute lung injury in guinea pigs after aerosol challenge with sonicated Pseudomonas aeruginosa whole cells," Arerugi 42(10):1616-1622 (1993) English translation of abstract only.
Keeling et al., "Local neutrophil influx following lateral fluid-percussion brain injury in rats is associated with accumulation of complement activation fragments of the third component (C3) of the complement system," J Neuroimmunol. 105:20-30 (2000).
Kodani et al., "Intratracheal administration of anaphylatoxin C5a potentiates antigen-induced pulmonary reactions through the prolonged production of cysteinyl-leukotrienes," Immunopharmacology. 49:263-274 (2000).
Krug et al., "Complement factors C3a and C5a are increased in bronchoalveolar lavage fluid after segmental allergen provocation in subjects with asthma," Am J Respir Crit Care Med. 164:1841-1843 (2001).
Kulik et al., "Pathogenic natural antibodies recognizing Annexin IV are required to develop intestinal ischaemia-reperfusion injury and are selected during development in a CR2/CD21-dependent manner," Mol. Immunology. 45:4110, Abstract 045 (2008).
Kyrkanides et al., "Enhanced glial activation and expression of specific CNS inflammation-related molecules in aged versus young rats following cortical stab injury," J Neuroimmunol. 119:269-277 (2001).
Köhl et al., "A regulatory role for the C5a anaphylatoxin in type 2 immunity in asthma," J Clin Invest. 116(3):783-796 (2006).
Lambrecht, "An unexpected role for the anaphylatoxin C5a receptor in allergic sensitization," J Clin Invest. 116(3):628-632 (2006).
Langlois et al., "Complement activation occurs through both classical and alternative pathways prior to onset and resolution of adult respiratory distress syndrome," Clin. Immunol. Immunopathol. 47: 152-163, 1988.
Larsen et al., "A differential effect of C5a and C5a des Arg in the induction of pulmonary inflammation," Am J Pathol. 100:179-192 (1980).
Leinhase et al., "Pharmacological complement inhibition at the C3 convertase level promotes neuronal survival, neuroprotective intracerebral gene expression, and neurological outcome after traumatic brain injury," Exp. Neurol. 199:454-464 (2006).
Lukacs et al., "Complement-dependent immune complex-induced bronchial inflammation and hyperreactivity," Am J Physiol Lung Cell Mol Physiol. 280:L512-L518 (2001).
Marciano et al., "Neuron-specific mRNA complexity responses during hippocampal apoptosis after traumatic brain injury," J Neurosci. 24:2866-2876 (2004).
Marshall et al., "A new classification of head injury based on computerized tomography," J. Neurosurg. 75:S14-S20 (1991).
Maruo et al., "Generation of anaphylatoxins through proteolytic processing of C3 and C5 by house dust mite protease," J Allergy Clin Immunol. 100(2):253-260 (1997).
Matis et al., "Complement-specific antibodies: designing novel anti-inflammatories," Nat Med. 1(8):839-842 (1995).

(56) References Cited

OTHER PUBLICATIONS

McArthur et al., "Moderate and severe traumatic brain injury: epidemiologic, imaging and neuropathologic perspectives," Brain Pathol. 14:185-194 (2004).
Mohamad et al., "Mitochondrial apoptotic pathways," Biocell. 29(2):149-161 (2005).
Morgan et al., "Expression of complement in the brain: Role in health and disease," Immunol Today. 17(10):461-466 (1996).
Mukherjee et al., "Allergic asthma: Influence of genetic and environmental factors," J Biol Chem. 286(38):32883-32889 (2011).
Nagata et al., "Activation of human serum complement with allergens," J Allergy Clin Immunol. 80(1):24-32 (1987).
Nagy et al., "The development of asthma in children infected with *Chlamydia pneumoniae* is dependent on the modifying effect of mannose-binding lectin," J Allergy Clin Immunol. 112:729-734 (2003).
Ohlsson et al., "Complement activation following optic nerve crush in the adult rat," J. Neurotrauma. 20:895-904(2003).
Peng et al., "Role of C5 in the development of airway inflammation, airway hyperresponsiveness, and ongoing airway response," J. Clin. Invest. 115(6):1590-1600(2005).
Peng et al., Abstract 200: "Contribution of complement component C5 in the development of airway inflammation, maintaining airway hyperresponsiveness and sustaining an ongoing asthmatic attack,"Abstracts/Mol Immunol. 41:292 (2004).
Peng et al., Late-breaking abstracts presented at scientific sessions AAAAI 62nd annual meeting, Mar. 3-7, "Blocking intrapulmonary activation of complement cascade on the development of airway hyperresponsiveness: Utility in sight?" Abstract LB2:720 (2006).
Pillay et al., "Administration of vaccinia virus complement control protein shows significant cognitive improvement in a mild injury model," Ann. N.Y. Acad. Sci. 1056:450-461(2005).
Qiu et al., "Upregulation of the fas receptor death-inducing signaling complex after traumatic brain injury in mice and humans," J. Neurosci. 22(9):3504-3511(2002).
Raghupathi et al., "BCL-2 overexpression attenuates cortical cell loss after traumatic brain injury in transgenic mice," J. Cereb. Blood Flow Metab. 18:1259-1269(1998).
Raghupathi et al., "Mild traumatic brain injury induces apoptotic cell death in the cortex that is preceded by decreases in cellular Bcl-2 immunoreactivity," Neuroscience. 110(4):605-616(2002).
Raghupathi et al., "Temporal alterations in cellular bax: Bcl-2 ratio following traumatic brain injury in the rat," J. Neurotrauma. 20(5):421-435(2003).
Raghupathi, "Cell death mechanisms following traumatic brain injury," Brain Pathol. 14:215-222(2004).
Ramer et al., "Setting the stage for functional repair of spinal cord injuries: A cast of thousands," Spinal Cord. 43:134-161(2005).
Rebhun et al., "Proteins of the complement system and acute phase reactants in sera of patients with spinal cord injury," Ann. Allergy 66:335-338(1991).
Rink et al., "Evidence of apoptotic cell death after experimental traumatic brain injury in the rat," Am. J. Pathol. 147(6):1575-1583(1995).
Robbins et al., "Complement activation by cigarette smoke," Am J. Physiol. 260:L254-L259 (1991).
Roof et al., "Gender differences in acute CNS trauma and stroke: Neuroprotective effects of estrogen and progesterone," J Neurotrauma. 17(5):367-388(2000).
Royo et al., "Pharmacology of traumatic brain injury," Current Opinion in Pharmacology. 3:27-32(2003).
Sambrook et al., Analysis of genomic DNA by Southern hybridization. *Molecular Cloning: A Laboratory Manual.* Second Edition, Cold Spring Harbor Labs Press: Cold Spring Harbor, NY, pp. 9.31-9.62(1989).
Schmidt et al., "The role of neuroinflammation in traumatic brain injury," Eur. J. Trauma. 3:135-149(2004).
Schreiber et al., Abstract No. 042 "Complement anaphylatoxin C5a and C5a receptor are fundamental to neutrophil activation and glomerulonephritis induced by anti-neutrophil cytoplasmic antibodies," Abstracts/Mol Immunol. 45:4109(2008).
Sinha et al., Abstract No. 043 "The receptor for complement anaphylatoxin C5a protects against the development of airway hyperresponsiveness in allergic asthma by inhibiting cysteinyl leukotriene pathway," Abstracts/Mol Immunol. 45:4109-4110 (2008).
Stahel et al., "Experimental closed head injury: Analysis of neurological outcome, blood-brain barrier dysfunction, intracranial neutrophil infiltration, and neuronal cell death in mice deficient in genes for pro-inflammatory cytokines," J. Cereb. Blood Flow Metab. 20:369-380 (2000).
Stahel et al., "Intrathecal levels of complement-derived soluble membrane attack complex (sC5b-9) correlate with blood-brain barrier dysfunction in patients with traumatic brain injury," J. Neurotrauma. 18(8): 773-781(2001).
Strauss et al., "Common patterns of Bcl-2 family gene expression in two traumatic brain injury models," Neurotox. Res. 6(4):333-342(2004).
Stribling et al., "Aerosol gene delivery in vivo," Proc. Natl. Acad. Sci. USA. 89:11277-11281(1992).
Takafuji et al., "Degranulation from human eosinophils stimulated with C3a and C5a," Int Arch Allergy Immunol. 104(Suppl 1):27-29 (1994).
Taube et al., "Inhibition of complement activation decreases airway inflammation and hyperresponsiveness," Am J Respir Cri. Care Med. 168:1333-1341 (2003).
Teasdale et al., "Assessment of coma and impaired consciousness," Lancet. 2:81-4 (1974).
Thurman et al., "Lack of functional alternative complement pathway ameliorates ischemic acute renal failure in mice," J Immunol. 170: 1517-1523, 2003.
Ueda et al., "Probing functional sites on complement protein B with monoclonal antibodies,"J. Immunol. 138: 1143-1149, 1987.
Van Beek et al., "Activation of the complement in the central nervous system: Roles in neurodegeneration and neuroprotection," Ann. N.Y. Acad. Sci. 992:56-71(2003).
Varsano et al., "Generation of complement C3 and expression of cell membrane complement inhibitory proteins by human bronchial epithelium cell line," Thorax. 55:364-369 (2000).
Versey et al., "Activation of complement in relation to disease," J. Clin. Pathol., 28, Suppl. (Assoc. Clin. Pathol) 6: 38-44, 1975.
Vos et al., "EFNS guideline on mild traumatic brain injury: report of an EFNS task force," Eur. J. Neurol. 9:207-219(2002).
Wang et al., "Anti-C5 monoclonal antibody therapy prevents collagen-induced arthritis and ameoliorates established disease," Proc Natl Aced Sci USA. 92(19):8955-9 (1995).
Williams et al., "In situ DNA fragmentation occurs in white matter up to 12 months after head injury in man," Acta Neuropathol. 102:581-590 (2001).
Winkelstein et al., "The role of C3 as an opsonin in the early stages of infection," Proc Soc Exp Biol Med. 149:397-401 (1975).
Wong et al., "Apoptosis and traumatic brain injury," Neurocrit Care. 3:177-182 (2005).
Xiong et al., "Formation of complement membrane attack complex in mammalian cerebral cortex evokes seizures and neurodegeneration," J Neurosci. 23:955-960 (2003).
Yakovlev et al., "Activation of CPP32-like caspases contributes to neuronal apoptosis and neurological dysfunction after traumatic brain injury," J Neurosci. 17:7415-7424 (1997).
Yao et al., "Progesterone differentially regulates pro- and anti-apoptotic gene expression in cerebral cortex following traumatic brain injury in rats," J Neurotrauma. 22:656-668 (2005).
Yatsiv et al., "Elevated intracranial IL-18 in humans and mice after traumatic brain injury and evidence of neuroprotective effects of IL-18-binding protein after experimental closed head injury," J Cereb Blood Flow Metab. 22:971-978 (2002).
Yatsiv et al., "Erythropoietin is neuroprotective, improves functional recovery, and reduces neuronal apoptosis and inflammation in a rodent model of experimental closed head injury," FASEB J. 19:1701-1703 (2005).
Barnum, "Inhibition of complement as a therapeutic approach in inflammatory central nervous system (CNS) disease," Mol Med. 5:569-582 (1999).

(56) References Cited

OTHER PUBLICATIONS

Becherer et al., "Segment spanning residues 727-768 of the complement C3 sequence contains a neoantigenic site and accommodates the binding of CR1, Factor H, and factor B," Biochemistry. 31:1787-1794 (1992).
Clark, "Antibody humanisation for therapeutic applications," <http://www.path.cam.ac.uk/~mrc7/humanisation/index.html>, printed Jun. 1, 2002 (4 pages).
Declaration of Joshua M. Thurman for U.S. Appl. No. 11/057,047, executed Apr. 16, 2008 (3 pages).
Farkas et al., "A neuronal C5a receptor and an associated apoptotic signal transduction pathway," J Physiol. 507:679-687 (1998).
Holm et al., "Functional mapping and single chain construction of the anti-cytokeratin 8 monoclonal antibody TS1," Mol. Immunol. 44:1075-1084 (2007).
Sewell et al., "Complement C3 and C5 play critical roles in traumatic brain cryoinjury: blocking effects on neutrophil extravasation by C5a receptor antagonist," *J. Neuroimmunol.* 155: 55-63, 2004.
Singhrao et al., "Spontaneous classical pathway activation and deficiency of membrane regulators render human neurons susceptible to complement lysis," *Am. J. Pathol.* 157: 905-918, 2000.
Stahel et al., "Intracerebral complement C5a receptor (CD88) expression is regulated by TNF and lymphotoxin-β following closed head injury in mice," J. Neuroimmunol. 109:164-172(2000).
Stahel et al., "The role of the complement system in traumatic brain injury," *Brain Res. Rev.* 27: 243-256, 1998.
International Search Report mailed on Feb. 11, 2009, for International Application No. PCT/US2008/003381, filed on Mar. 14, 2008 (3 pages).
International Search Report mailed on Jul. 7, 2005, for International Application No. PCT/US2005/004346, filed on Feb. 10, 2005 (2 pages).
Abbas, et al., eds., *Cellular and Molecular Immunology*. W.B. Saunders Company, 54 (1991).
Alexander et al., "Complement-dependent apoptosis and inflammatory gene changes in murine lupus cerebritis," J Immunol. 175(12):8312-8319 (2005).
"Monoclonal antibody to human factor B (Bb), Catalog No. A227," Quidel Corporation Product Catalog, <http://www.quidel.com/products/product_detail.php?group=2&prod=83>, retrieved on Aug. 4, 2008 (2 pages).
Attwood, "The babel of bioinformatics," Science. 290:471-3 (2000).
Bendayan, "Possibilities of false Immunocytochemical results generated by the use of monoclonal antibodies: The example of the anti-proinsulin antibody," J Histochem Cytochem. 43:881-886 (1995).
Bendig, "Humanization of rodent monoclonal antibodies by CDR grafting," Methods: A Companion to Methods in Enzymology. 8:83-93 (1995).
Boos et al., "Murine complement C4 is not required for experimental autoimmune encephalomyelitis," Glia. 49:158-160 (2004).
Bost et al., "Antibodies against a peptide sequence within the HIV envelope protein crossreacts with human interleukin-2," Immunol Invest. 17:577-586 (1988).
Brandis, "Acid-Base Physiology," <http://www.anaesthesiamcq.com/AcidBaseBook/ab4_4.php>, retrieved on Sep. 19, 2011 (2 pages).
Caldas et al., "Humanization of the anti-CD18 antibody 6.7: An unexpected effect of a framework residue in binding to antigen," Mol Immunol. 39:941-952 (2003).
Chàrdes et al., "Efficient amplification and direct sequencing of mouse variable regions from any immunoglobulin gene Family," FEBS Lett. 452:386-394 (1999).
Chien et al., "Significant structural and functional change of an antigen-binding site by a distant amino acid substitution: proposal of a structural mechanism," Proc Natl Acad Sci USA. 86:5532-5536 (1989).
Choi et al., "Inhalation delivery of proteins from ethanol suspensions," Proc Natl Acad Sci. 98(20):11103-11107 (2001).

Clardy et al., "In vitro inhibition of complement activation using a monoclonal antibody (McAb) directed against human Factor B (FB), Abstract No. 1969," Pediatric Res. 31:331 A (1992).
Cole et al., "Beyond lysis: how complement influences cell fate," Clin Sci (Lond). 104:455-466 (2003).
Cole et al., "Complement regulator loss on apoptotic neuronal cells causes increased complement activation and promotes both phagocytosis and cell lysis," Mol Immunol. 43:1953-1964 (2006).
Daha et al., "Stabilization of the amplification convertase of complement by monoclonal antibodies directed against human factor B," J Immun. 132(5):2538-42 (1984).
De Broe et al., "Pathophysiology of hemodialysis-associated hypoxemia," Adv Nephrol Necker Hosp. 18:297-315, Abstract Only (1989).
Extended European Search Report for European Patent Application No. 10188613.3, dated May 31, 2011 (10 pages).
German et al., "Systemic complement depletion inhibits experimental cerebral vasospasm," Neurosurgery. 39:141-145, discussion 145-146, Abstract Only (1996).
Gilkeson, "Role of complement factor B in the pathogenesis of SLE, Project No. 5R01 AI047469-05," <<http://projectreporter.nih.gov/pr_Prj_info_desc_dtls.cfm?icde=0&aid=6712799&print=yes>>, retrieved on Apr. 25, 2011 (2 pages).
Girardi et al., "Complement C5a receptors and neutrophils mediate fetal injury in the Antiphospholipid Syndrome," J. Clin. Invest. Corrigendum. 113:646 (2004).
Giusti, et al. "Somatic diversification of S107 from an antiphosphocholine to an anti-DNA autoantibody is due to a single base change in its heavy chain variable region," Proc Natl Aced Sci USA. 84:2926-2930 (1987).
Glovsky, et al., "Complement determinations in human disease," Ann Allergy, Asthma Immunol. 93(6):513-523 (2004).
Hall, "Cooperative Interaction of Factor B and other complement components with mononuclear cells in the antibody-independent lysis of xenogeneic erythrocytes," J Exp Med. 156:834-843 (1982).
Holers et al., "The alternative pathway of complement in disease: Opportunities for therapeutic targeting," Mol. Immunol. 41:147-152 (2004).
Holers, "Phenotypes of Complement Knockouts," Immunopharmacology. 49:125-131 (2000).
Holers, "The complement system as a therapeutic target in autoimminity," Clin Immunol. 107:140-151 (2003).
International Search Report for PCT Application No. PCT/US2008/003381, mailed Feb. 11, 2009 (3 pages).
International Search Report for PCT Application No. PCT/US2005/04346, mailed Jul. 7, 2005 (2 pages).
International Search Report for PCT Application No. PCT/US2006/020460, mailed Aug. 29, 2006 (3 pages).
Jaeschke et al., "Role of neutrophils in acute inflammatory livery injury," Liver Int. 26:912-919 (2006).
Kaczorowski et al., "Effect of Soluble Complement Receptor-1 on Neutrophil Accumulation After Traumatic Brain Injury in Rats," J Cereb Blood Flow Metab. 15:860-864 (1995).
Kang et al., "A novel anti-human Factor B monoclonal antibody inhibits Factor D-mediated associate and cleavage of Factor B," Abstract No. 191, Immunopharmacology. 49:68 (2000).
Kolb et al., "Ba and Bb fragments of factor B activation: Fragment production, biological activities, neoepitope expression and quantitation in clinical samples," Complement Inflamm. 6:175-204 (1989).
Kossmann et al., "Elevated levels of the complement components C3 and factor B in ventricular cerebrospinal fluid of patients with traumatic brain injury," J Neuroimmunol. 73:63-69 (1997).
Kulkarni et al., "Neuroprotection from complement-mediated inflammatory damage," Ann N Y Acad Sci. 1035:147-164 (2004).
Kurucz et al., Current animal models of bronchial asthma, Curr Pharm Des. 12(25):3175-3194 (2006).
Kuttner-Kondo et al., "Characterization of the active sites in decay-accelerating factor," J Immunol. 167(4):2164-2171 (2001).
Lederman et al., "A single amino acid substitution in a common African allele of the CD4 molecule ablates binding of the monoclonal antibody, OKT4," Mol Immunol. 28(11):1171-1181 (1991).

(56) References Cited

OTHER PUBLICATIONS

Leinhase et al., "Reduced neuronal cell death after experimental brain injury in mice lacking a functional alternative pathway of complement activation," BMC Neurosci. 7:55 (2006).
Lemanske, "Asthma therapies revisited: what have we learned?" Proc Am Thorac Soc. 6:312-315 (2009).
Leslie et al., "Complement Receptors," Encylopedia of Life Sciences, Nature Publishing Group. (2001) (9 pages).
Li et al., "beta-Endorphin omission analogs: Dissociation of immunoreactivity from other biological activities." Proc Natl Acad Sci USA. 77(6):3211-3214 (1980).
MacCallum et al., "Antibody-antigen interactions: Contact analysis and binding site topography." J Mol Biol. 262(5):732-45 (1996).
Mariuzza et al., The structural basis of antigen-antibody recognition, Annu Rev Biophys Chem. 16:139-159 (1987).
Matsumoto et al., "Abrogation of the alternative complement pathway by targeted deletion of murine factor B," Proc Natl Acad Sci USA. 94(16):8720-8725 (1997).
Maulik et al., "Molecular biotechnology: therapeutic applications and strategies," Wiley-Liss, Inc., pp. v-viii (Table of Contents Only), 1997.
Morgan, "Regulation of the complement membrane attack pathway," Crit Rev Immunol. 19(3):173-198 (1999).
Nataf et al., "Attenuation of experimental autoimmune demyelination in complement-deficient mice," J Immunol. 165(10):5867-5873 (2000).
Nataf et al., "Complement anaphylatoxin receptors on neurons: New tricks for old receptors?" Trends Neurosci. 22(9):397-402 (1999).
O'Barr et al., "Neuronal expression of a functional receptor for the C5a complement activation fragment," J Immunol. 166(6):4154-4162 (2001).
Ohlsson et al., "Complement activation after lumbosacral ventral root avulsion injury," Neurosci Lett. 394(3):179-183 (2006).
Padlan et al., "Structure of an antibody-antigen complex: crystal structure of the HyHEL-10 Fab-lysozyme complex," Proc Natl Acad Sci USA. 86(15):5938-5942 (1989).
Peters et al., "The Bb fragment of complement factor B acts as a B cell growth factor." J Exp Med. 169(4):1225-1235 (1988).
Rader et al., "A phage display approach for rapid antibody humanization: Designed combinatorial V gene libraries," Proc Natl Sci USA. 95:8910-8915 (1998).
Rancan et al., "Central nervous system-targeted complement inhibition mediates neuroprotection after closed head injury in transgenic mice," J. Cereb. Blood Flow. Metab. 23(9):1070-1074(2003).
Reynolds et al., "Vaccinia Virus Complement Control Protein Reduces Inflammation and Improves Spinal Cord Integrity Following Spinal Cord Injury," Ann. NY. Acad Sci. 1035:165-178(2004).
Rood et al., "Reduction of early graft loss after intraportal porcine islet transplantation in monkeys," Transplantation. 83(2):202-210 (2007) Abstract Only.
Rounioja et al., "Mechanism of acute fetal cardiovascular depression after maternal inflammatory challenge in mouse," Am J Pathol. 166(6):1585-1592 (2005).
Rudikoff et al., "Single amino acid substitution altering antigen-binding specificity," Proc Natl Acad Sci USA. 79(6):1979-1983 (1982).
Sauerland et al., "A CRASH landing in severe head injury," Lancet. 364(9442):1291-1292 (2004).
Schmidt et al., "Closed head injury—an inflammatory disease?," Brain Res. Rev. 48(2):388-399(2005).
Shacka et al., "Regulation of neuronal cell death and neurodegeneration by members of the Bcl-2 family: Therapeutic implications," Curr Drug Targets CNS Neurol Disord. 4(1):25-39 (2005).
Skolnick et al., "From genes to protein structure and function: novel applications of computational approaches in the genomic era," Trends Niotechnol. 18(1):34-39 (2000).
Supplementary European Search Report for European Application No. 06771303.2, dated Oct. 28, 2011 (5 pages).
Supplementary Partial European Search Report for European Application No. 05722948.6, dated Jun. 24, 2008 (6 pages).
Takahashi et al., "Solubilization of antigen-antibody complexes: a new function of complement as a regulator of immune reactions," Prog Allergy. 27:134-166 (1980).
Tanaka et al., "Murine monoclonal anti-Ba antibody that enhances haemolytic activity of Factor B," Immunology. 73(4):383-387(1991).
Tatusova et al., "BLAST 2 Sequences, a new tool for comparing protein and nucleotide sequences," FEMS Microbiol Lett. 174(2):247-250 (1999).
Taube et al., "Factor B of the alternative complement pathway regulates development of airway hyperresponsiveness and inflammation," Proc Natl Aced Sci USA. 103(21):8084-8049 (2006).
Thurman et al., "A novel inhibitor of the alternative compliment pathway prevents antiphospholipid antibody-induced pregnancy loss in mice," Mol Immunol. 42(1):87-97 (2005).
Thurman et al., "A novel inhibitor of the alternative pathway of complement protects mice from ischemic acute renal failure," American Nephrology Society Meeting, Abstract (1 page), 2004.
Thurman et al., "Acute tubular necrosis is characterized by activation of the alternative pathway of complement," Kidney Int. 67:524-530 (2005).
Thurman et al., "Complement activation through the alternative pathway is necessary for the development of airway hyperresponsiveness (AHR) and inflammation in a model of human asthma," Mol Immunol., 41:319, Abstract No. 256.
Thurman et al., "The central role of the alternative complement pathway in human disease," J Immunol. 176(3):1305-1310 (2006).
Thurman et al., "Treatment with an inhibitory monoclonal antibody to mouse factor B protects mice from induction of apoptosis and renal ischemia/reperfusion injury," J Am Soc Nephrol. 17(3):707-715 (2006).
Watanabe et al., "Modulation of renal disease in MRL/lpr mice genetically deficient in the alternative complement pathway factor B," J Immunol. 164(2):786-794 (2000).
Younger et al., "Detrimental effects of complement activation in hemorrhagic shock," J Appl Physiol. 90:441-446 (2001).
Zhang et al., "Bench-to-bedside review: Apoptosis/programmed cell death triggered by traumatic brain injury," Crit Care. 9(1):66-75 (2005).
"Monoclonal antibody to human factor B (Ba), Catalog No. A225," Quidel Corporation Product Catalog, <http://www.quidel.com/products/product_detail.php?group=2&prod=82>, retrieved on Aug. 4, 2008 (2 pages).
Xu, Y.et al., (1997) "Contribution of the complement control protein modules of C2 in C4b binding assessed by analysis of C2/factor B chimeras," J. Immunol. 158: 5958-5965.
Girardi et al., (Dec. 2003) "Complement C5a receptors and neutrophils mediate fetal injury in the Antiphospholipid Syndrome," J. Clin. Invest. 112(11):1644-1654.
Pardridge, "The blood-brain barrier and neurotherapeutics," NueroRx. 2(1):1-2 (2005).
May, "The Quest for an Acute Traumatic Brain Injury Treatment: Why Progesterone Could Be on Track to Become the First FDA-Approved Therapy," <www.news-medical.net>, retrieved on Feb. 10, 2014 (7 pages).

\* cited by examiner

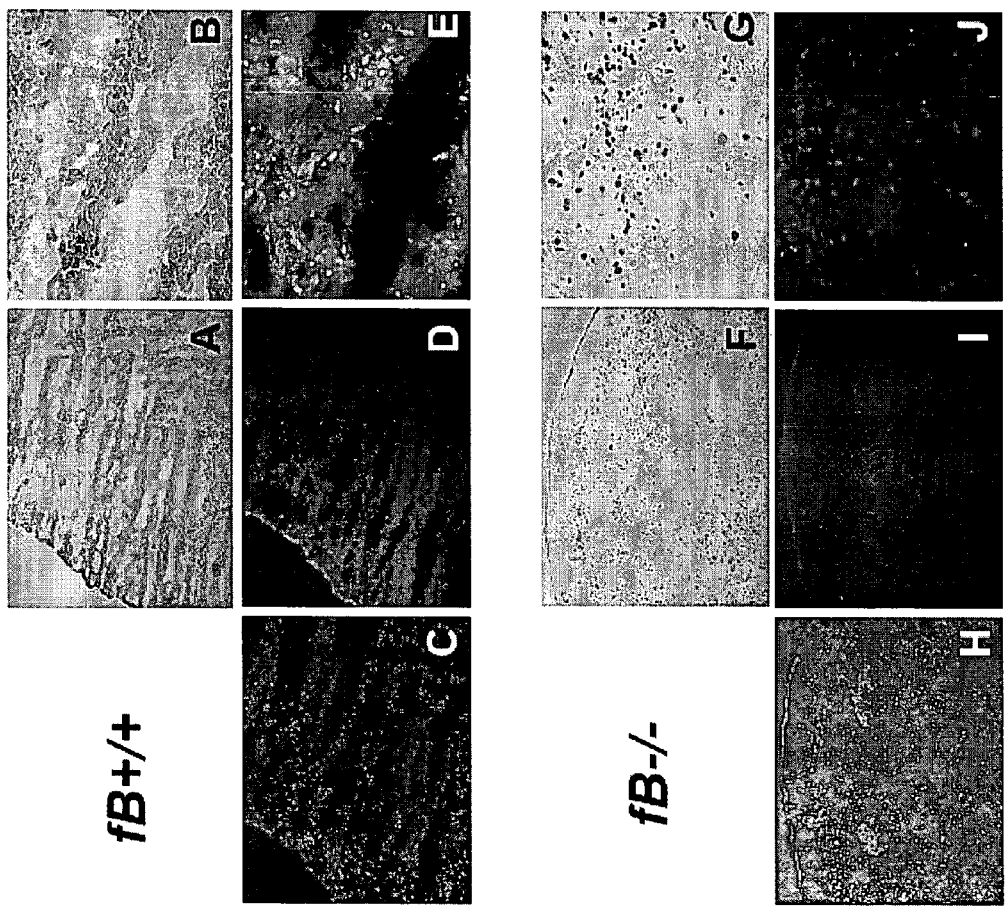

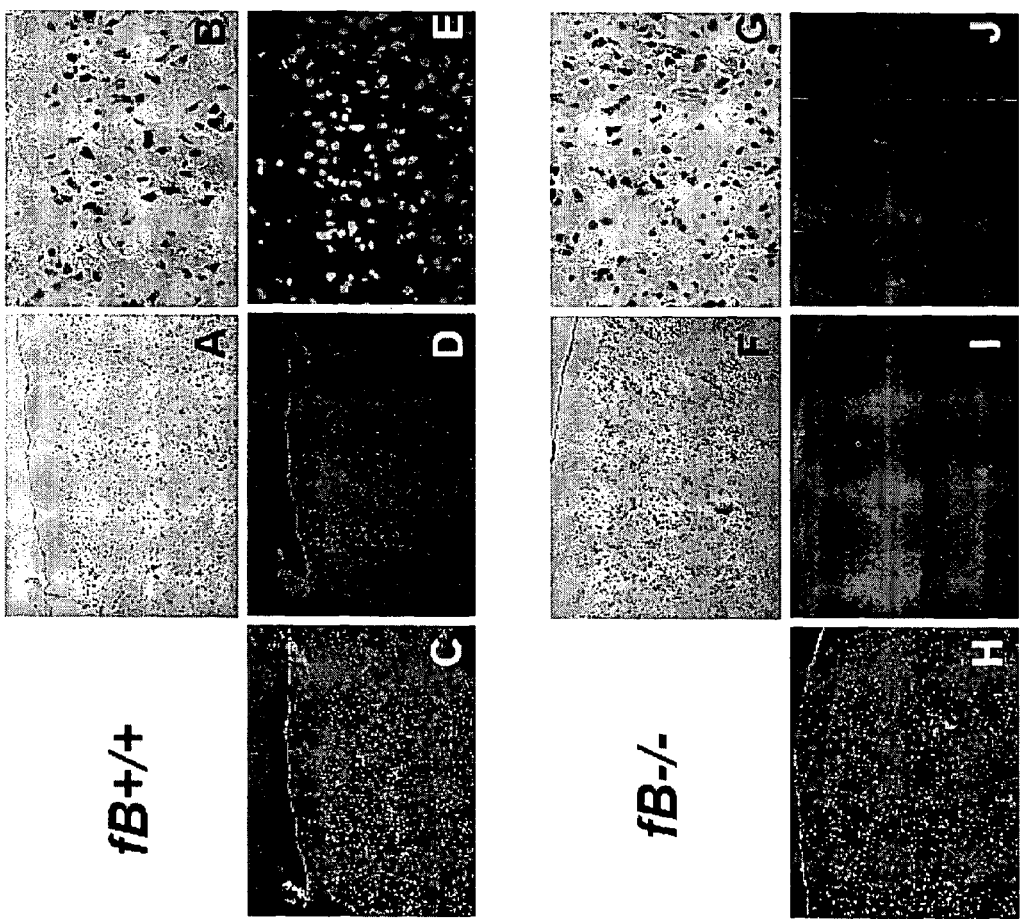

INHIBITION OF THE ALTERNATIVE COMPLEMENT PATHWAY FOR TREATMENT OF TRAUMATIC BRAIN INJURY, SPINAL CORD INJURY AND RELATED CONDITIONS

CROSS-REFERENCE TO RELATED APPLICATIONS

This application claims the benefit of priority under 35 U.S.C. §119(e) from U.S. Provisional Patent Application No. 60/685,289, filed May 26, 2005. The entire disclosure of U.S. Provisional Patent Application No. 60/685,289 is incorporated herein by reference.

STATEMENT REGARDING FEDERALLY SPONSORED RESEARCH OR DEVELOPMENT

This invention was made with government support under National Institutes of Health Grant No. AI047469. The government has certain rights in the invention.

FIELD OF THE INVENTION

The present invention generally relates to methods of treating physiological damage resulting from traumatic brain injury, spinal cord injury, or related conditions, by selectively inhibiting the alternative complement pathway, and in a particular embodiment, by inhibiting factor B.

BACKGROUND OF THE INVENTION

Complement activation occurs primarily by three pathways: the so-called classical pathway, the lectin pathway and the alternative pathway. The key proteins involved in the activation of the alternative pathway are factor B (fB) and factor D (fD). These proteins work in concert to initiate and/or to amplify the activation of C3, which then leads to the initiation of a number of inflammatory events. A third protein, properdin, stabilizes the complex of C3 and factor B but is not absolutely required for the alternative pathway to function. Factor B also helps solubilize immune complexes, has been reported to act as a B cell growth factor and can activate monocytes (Takahashi, 1980; Hall, 1982; Peters, 1988). Factor B-deficient mice (fB−/− mice) have been generated and IgG1 antibody response to T-cell dependent antigens and sensitivity to endotoxic shock appear normal in these mice (Matsumoto, 1997).

The alternative complement pathway is usually initiated by bacteria, parasites, viruses or fungi, although IgA Abs and certain Ig L chains have also been reported to activate this pathway. Alternative pathway activation is initiated when circulating factor B binds to activated C3 (either C3b or C3H2O). This complex is then cleaved by circulating factor D to yield an enzymatically active fragment, C3bBb. C3bBb cleaves C3 generating C3b, which drives inflammation and also further amplifies the activation process, generating a positive feedback loop. Both components (factor B and factor D) are required to enable activation of the alternative pathway.

Recent studies have shown that the alternative pathway of complement plays an important role in the pathogenesis of several animal models of disease. For example, complement activation within the kidney after ischemia reperfusion injury (I/R) is mediated almost exclusively by the alternative pathway (Thurman et al., 2003, *J Immunol* 170:1517-1523), and the alternative pathway plays a critical role in the development of inflammatory arthritis. Perhaps most surprisingly, mice deficient in the alternative pathway have been demonstrated to be protected from nephritis in the MRL/lpr model of lupus nephritis (Watanabe et al., 2000, *J Immunol* 164:786-794) and from anti-phospholipid mediated fetal loss (Girardi et al., 2003, *J Clin Invest* 112:1644-1654), models that would traditionally have been assumed to be mediated by the classical complement pathway. In addition, Nataf et al. has shown that, in an experimental autoimmune encephalomyelitis (EAE) model, in both C3(−/−) and factor B(−/−) mice, there was little infiltration of the parenchyma by macrophages and T cells and, as compared with their wild-type littermates, the central nervous systems (CNS) of both C3(−/−) and factor B(−/−) mice induced for EAE are protected from demyelination (Nataf et al., 2000, *J. Immunol.* 165:5867-5873). Subsequent studies of autoimmune pathology in C4 (−/−) mice in the EAE model showed that deletion of the C4 gene does not significantly change either the time of onset or the severity and tempo of myelin oligodendrocyte-induced EAE compared with controls with a fully intact complement system, indicating that the contribution of murine complement to the pathogenesis of demyelinating disease is realized via the alternative pathway (Boos et al., 2005, *Glia* 49:158-160).

Traumatic brain injury (also referred to herein as TBI) is a condition with very deleterious effects on an individual's health that currently has no effective treatment. Complement activation has been shown to be involved in the development of brain damage following TBI (Bellander et al., 2001, *J. Neurotrauma* 18:1295-1311; Kaczorowski et al., 1995, *J. Cereb. Blood Flow Metab.* 15:860-864; Keeling et al., 2000, *J. Neuroimmunol.* 105:20-30; Schmidt et al., 2004, *Eur. J. Trauma* 30:135-149; Nataf et al., 1999, *Trends Neurosci* 22:397-402; Stahel et al., 1998, *Brain Res. Rev.* 27:243-256; Stahel et al., 2001, *J. Neurotrauma* 18:773-781; Van Beek et al., 2003, *Ann NY Acad Sci* 992:56-71; Rancan et al., 2003, *J. Cereb. Blood Flow & Metab.* 23:1070-1074). However, these studies have focused on the effects of the complement cascade at a point where all three pathways that activate complement converge, such as at C3 (see, for example, Rancan et al., 2003, ibid.). Therefore, prior to the present invention, there have been no reports showing whether one of the complement pathways is preferentially or exclusively activated as a result of TBI, or is required to develop TBI.

The immediate goal in the management of head-injured patients is the prevention of secondary brain damage by rapid correction of hypotension, hypoxemia, hypercarbia and hypoglycemia. The main priority in the early management of head trauma patients is the maintenance of an adequate cerebral perfusion pressure (CPP), which should be above 70-80 mmHg. Different therapeutic approaches are aimed at lowering the intracranial pressure (ICP) in order to keep an adequate CPP. Among the therapeutic modalities are: the reduction of mass lesions by surgical evacuation of intracranial hematomas, the reduction of brain swelling with osmotic drugs (e.g., mannitol), and the therapeutic drainage of cerebrospinal fluid (CSF) through intraventricular catheters. Patients with severe TBI are transferred to intensive care unit (ICU) at the earliest timepoint and treated according to standardized protocols. Goals of ICU therapy include: achievement and maintenance of adequate gas exchange and circulatory stability, prevention of hypoxemia and hypercarbia, repeated, scheduled computerized tomography (CT) scans for detection of delayed secondary intracranial pathology, profound sedation and analgesia to avoid stress and pain, achievement and maintenance of optimal CPP (>70 mmHg) and cerebral oxygen balance, avoidance of hyperthermia (<38° C.), prevention of hyperglycemia and hyponatremia, no routinely performed head elevation, prevention of stress ulcers and maintenance of gut mucosal integrity, and prophylaxis for complicating factors (e.g. pneumonia or meningitis). In the event of elevated ICP (>15 mmHg, >5 minutes), patients can be treated by (1) deepening of sedation, analgesia, muscle relaxation; (2) CSF drainage through ventricular catheters; (3) moderate hyperventilation (under certain circumstances); (4) osmotherapy; (5) moderate hypothermia (±34° C.); and (6) barbiturate coma.

Spinal Cord Injury (also referred to herein as SCI) is also a condition of the central nervous system with very deleterious effects on an individual's health that currently has no effective treatment. Complement activation has been shown to be involved in the development of damage following SCI (Anderson et al., 2004, *J Neurotrauma* 21 (12):1831-46; Reynolds et al., 2004, *Ann NY Acad Sci.* 1035:165-78; Rebhun et al., 1991, *Ann Allergy* 66 (4):335-8). However, as with TBI, these studies have focused on the effects of the complement cascade at a point where all three pathways that activate complement converge, or have suggested a role for all complement pathways subsequent to SCI. Therefore, prior to the present invention, there have been no reports showing whether one of the complement pathways is preferentially or exclusively activated as a result of SCI, or is required to develop SCI.

SCI is generally defined as damage to the spinal cord that results in a loss of function, such as mobility or feeling. Frequent causes of damage are trauma (e.g., by car accident, gunshot, falls, etc.) or disease (polio, spina bifida, Friedreich's Ataxia, etc.). The spinal cord does not have to be severed in order for a loss of functioning to occur. In fact, in most individuals with SCI, the spinal cord is intact, but the damage to it results in loss of function. Besides a loss of sensation or motor function, individuals with SCI may also experience dysfunction of the bowel and bladder, sexual and fertility dysfunction, inability to regulate blood pressure effectively, reduced control of body temperature, inability to sweat below the level of injury, and chronic pain. Very high injuries (C-1, C-2) can result in a loss of many involuntary functions including the ability to breathe, necessitating breathing aids such as mechanical ventilators or diaphragmatic pacemakers.

Currently there is no cure for SCI. The immediate goal in the management of SCI patients is focused on decreasing damage as soon as possible after the injury occurs. Steroid drugs such as methylprednisolone reduce swelling, which is a common cause of secondary damage at the time of injury. There are several types of treatment in the short term for a spinal cord injury. First, the spine in the area of the injured spinal cord is immobilized to prevent further injury to the cord (e.g., using halos, casts, braces and straps). To reduce swelling in the spinal cord caused by injury, steroid medication is usually given during the first 24 hours following injury, although the more typical approach is to give steroid medication to those patients with neurological deficits and a time window of initiation of therapy within less than 8 hours after trauma (Bracken, 2001, *Spine* 26 (24S):S47-S54). Other medical treatment is often necessary, depending on complications that may develop. Because traumatic injury to the spinal cord usually involves an injury to the bones and ligaments of the spine, surgery may be performed. The aim of some surgeries is to remove bone (decompression) that is pressing on or into the spinal cord, or to stabilize or realign the spine in the area of the spinal cord injury when the vertebrae or ligaments have been damaged. Metal rods or cages and screws may be attached to normal vertebrae to prevent movement of fractured vertebrae and the vertebrae may be "fused" together using bone graft or the same reason. Stretching of the spine using weights and pulleys (called traction) may also help with alignment of the spine.

Despite the protocols for treatment of patients with TBI, potential complications from TBI therapy can include: cerebral vasospasms or cardiovascular depression, hepatotoxicity, immunosuppression, and increased incidence of pulmonary infections. In addition, although treatments for SCI may provide modest reductions in physiological damage, many protocols are primarily useful to help reduce the likelihood of further damage and to stabilize the patient. No single protocol has been proven to be entirely satisfactory for inhibiting the development of the physiological damage resulting from TBI or SCI. Therefore, there is a continuing need in the art for therapeutic processes and reagents having less toxicity and more specificity for the underlying cause of damage resulting from TBI and SCI.

SUMMARY OF THE INVENTION

One embodiment of the present invention relates to a method to reduce or prevent at least one symptom of physiological damage resulting from traumatic brain injury (TBI) in an animal or enhance recovery from TBI in the animal. The method includes selectively inhibiting the alternative complement pathway in an animal that has experienced TBI. In one aspect, the symptom is selected from: cerebral vasospasms, cardiovascular depression, hepatotoxicity, immunosuppression, and/or pulmonary infection. In another aspect, the symptom is selected from the group consisting of: hypotension, hypoxemia, hypercarbia and/or hypoglycemia.

Another embodiment of the present invention relates to a method to reduce or prevent at least one symptom of physiological damage resulting from spinal cord injury (SCI) in an animal or enhance recovery from SCI in the animal. The method includes selectively inhibiting the alternative complement pathway in an animal that has experienced SCI. In one aspect, the symptom is spinal cord swelling.

In any of the above-described methods, the step of inhibiting can include administering to the animal an agent that selectively inhibits the expression or activity of a protein in the alternative complement pathway. The protein in the alternative complement pathway is preferably selected from: Factor B, Factor D and/or properdin. Such agents include, but are not limited to, an inhibitor of expression of the protein in the alternative complement pathway, an inhibitor of the biological activity of the protein in the alternative complement pathway, and/or an antagonist of the protein in the alternative complement pathway.

In one aspect, the agent used in any of the above-identified methods is an antibody, an antigen binding fragment thereof, or an antigen binding polypeptide, that selectively binds to and inhibits the protein in the alternative complement pathway. In one aspect, the antibody or antigen-binding fragment thereof selectively binds to factor B within the third short consensus repeat (SCR) domain, wherein the antibody prevents formation of a C3bBb complex. In one aspect, the antibody or antigen-binding fragment thereof binds to factor B and prevents or inhibits cleavage of factor B by factor D. In one aspect, the antibody or antigen binding fragment bind to the third short consensus repeat (SCR) domain of human factor B. In another aspect, the antibody or antigen binding fragment thereof selectively binds to an epitope in the third SCR domain of factor B selected from: (a) an epitope of factor B that includes at least a portion of human factor B (SEQ ID NO:2) comprising from about position Tyr139 to about position Ser185, or equivalent positions thereto in a non-human factor B sequence; (b) an epitope of factor B that includes at least a portion of human factor B (SEQ ID NO:2) comprising from about position Tyr139 to about position Ser141, or equivalent positions thereto in a non-human factor B sequence; (c) an epitope of factor B that includes at least a portion of human factor B (SEQ ID NO:2) comprising from about position Glu182 to about position Ser185, or equivalent positions thereto in a non-human factor B sequence; and/or (d) an epitope of factor B that includes at least a portion of human factor B (SEQ ID NO:2) comprising any one or more of the following positions or their equivalent positions in a non-human factor B sequence: Tyr139, Cys 140, Ser141, Glu182, Gly184, or Ser185. In one aspect, the antibody or antigen binding fragment thereof selectively binds to an epitope in the third SCR domain of factor B (SEQ ID NO:2) comprising one or more of the following amino acid positions or their equivalent positions in a non-human factor B sequence: Ala137, Tyr139, Ser141, Glu182, Ser185, Thr189, Glu190, and Ser192. In another aspect, the antibody or antigen binding fragment thereof selectively binds to an epitope in the third SCR domain of factor B (SEQ ID NO:2) comprising or consisting of the following amino acid positions or their equivalent positions in a non-human factor B sequence: Ala137, Tyr139, Ser141, Glu182, Ser185, Thr189, Glu190, and Ser192. In yet another aspect, the antibody or antigen binding fragment thereof selectively binds to a non-linear epitope within the three-dimensional structure of a portion of the third SCR domain of factor B, wherein the portion is defined by at least amino acid positions Ala137-Ser192 of SEQ ID NO:2 or equivalent positions in a non-human factor B sequence. In yet another aspect, the antibody or antigen binding fragment thereof selectively binds to factor B from multiple mammalian species and prevents formation of a C3bBb complex. In one aspect, the antibody or antigen binding fragment thereof selectively binds to factor B from human and an animal selected from the group consisting of non-human primate, mouse, rat, pig, horse and rabbit. For any of the antibodies described above, the antibody can include, but is not limited to, an antibody of a non-complement activating isotype or subclass, a monoclonal antibody, a humanized antibody, a bispecific antibody, and/or a monovalent antibody. In one aspect, the antigen binding fragment is an Fab fragment. In one preferred aspect of the invention, the antibody is the monoclonal antibody 1379 (produced by ATCC Deposit No. PTA-6230), or an antigen-binding fragment thereof.

In the methods and uses related to TBI, in a preferred embodiment, the agent is administered intravenously or to the brain of the animal. In the methods and uses related to SCI, in a preferred embodiment, the agent is administered intravenously or to the spinal cord or epidural space of the spinal cord of the animal. The agent is preferably administered to the animal in an amount effective to measurably reduce at least one symptom of physiological damage resulting from TBI or SCI in the animal as compared to in the absence of administration of the agent. With respect to TBI, in one aspect, the agent is administered in an amount effective to maintain a cerebral perfusion pressure (CPP) of above 70-80 mmHg, or in an amount effective to lower intracranial pressure (ICP). With respect to SCI, in one aspect, the agent is administered in an amount effective to reduce swelling in the spinal cord. In one aspect, the agent is administered in a pharmaceutically acceptable carrier, including, but not limited to, a compound or composition that is capable of crossing the blood-brain barrier and/or an injectable excipient.

In one aspect of any of the methods described above related to TBI, there is a further step of administering to the animal another compound for treating a symptom of TBI selected from the group consisting of: a physical impairment, a cognitive impairment, and a psychosocial-behavioral-emotional impairment. Such a compound can include, but is not limited to, an osmotic drug, a sedative, an analgesic, a muscle relaxant, and/or a barbituate.

In one aspect of any of the methods described above related to SCI, there is a further step of administering a steroid to the animal.

In one aspect of any of the methods described above related to TBI, the method can further include treating the animal for TBI by a protocol selected from: reduction of mass lesions by surgical evacuation of intracranial hematomas; reduction of brain swelling with osmotic drugs; therapeutic drainage of cerebrospinal fluid (CSF) through intraventricular catheters; computerized tomography (CT) scans; sedation; analgesia; muscle relaxation; moderate hyperventilation; moderate hypothermia; and/or barbiturate coma.

In one aspect of any of the methods described above related to SCI, the method can further include treating the animal for SCI by a protocol selected from: administration of steroids; immobilization of the spine; decompression surgery; surgery to stabilize the vertebrae; surgery to realign the vertebrae; and/or traction.

In any of the above-described methods and uses, the animal is preferably a mammal, including, but not limited to, a human.

Further embodiments of the present invention relate to (1) a method to reduce or prevent at least one symptom of physiological damage resulting from traumatic brain injury (TBI) in an animal that has experienced TBI, or (2) a method to reduce or prevent at least one symptom of physiological damage resulting from spinal cord injury (SCI) in an animal that has experienced SCI, each method comprising administering to the animal an agent that inhibits factor B by binding to or blocking the third short consensus repeat (SCR) domain of factor B. In a preferred aspect of these embodiments, the agent is an antibody or an antigen-binding fragment thereof that selectively binds to factor B.

Another embodiment of the present invention relates to a composition comprising: (a) a first agent selected from: an isolated antibody, an antigen-binding fragment thereof, and/or an antigen-binding polypeptide, wherein the first agent selectively inhibits the expression or biological activity of a protein in the alternative complement pathway; and (b) a second agent for the treatment of a symptom of traumatic brain injury (TBI). In one aspect, the second agent is compound for treating a symptom of TBI selected from: a physical impairment, a cognitive impairment, and/or a psychosocial-behavioral-emotional impairment. In another aspect, the second agent is selected from the group consisting of: an osmotic drug, a sedative, an analgesic, a muscle relaxant, and a barbituate.

Yet another embodiment of the present invention relates to a composition comprising: (a) a first agent selected from: an isolated antibody, an antigen-binding fragment thereof, and/or an antigen-binding polypeptide, wherein the first agent selectively inhibits the expression or biological activity of a protein in the alternative complement pathway; and (b) a second agent for the treatment of a symptom of spinal cord injury (SCI). In one aspect, the second agent is a steroid.

In either of the above-identified compositions, the first agent can include, but is not limited to, an agent that inhibits the expression or biological activity of a protein selected from: Factor B, Factor D and/or properdin. In one aspect, the first agent binds to factor B within the third short consensus repeat (SCR) domain and inhibits or prevents formation of a C3bBb complex. In another aspect, the first agent is an antibody or antigen binding fragment thereof. In a preferred aspect, the antibody is the monoclonal antibody 1379. Any of the agents described above for use in the methods or uses of the invention can be used in the composition of the invention.

BRIEF DESCRIPTION OF THE FIGURES

FIG. 13 is a digital image showing attenuated neuronal cell death in the injured hemisphere of factor B gene-deficient mice 24 hours after closed head injury.

FIG. 14 is a digital image showing attenuated neuronal cell death in the injured hemisphere of factor B gene-deficient mice 7 days after closed head injury.

DETAILED DESCRIPTION OF THE INVENTION

Figure 1:
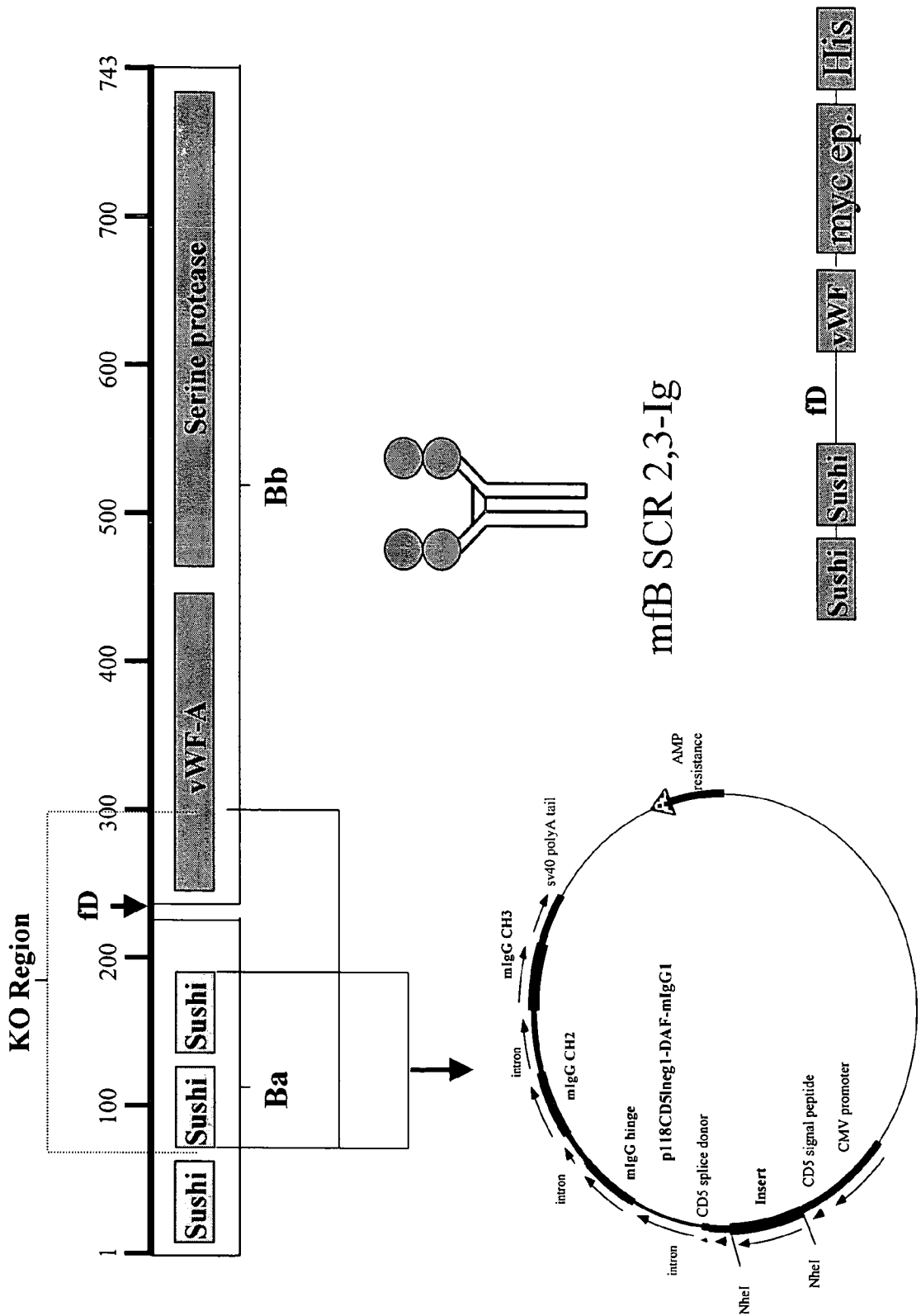
FIG. 1 is a schematic diagram showing the construction of a factor B-Ig fusion protein.

The present invention generally relates to the inventors' discovery that activation of the complement cascade through the alternative pathway is necessary for the induction of physiological damage due to traumatic brain injury (TBI), and that inhibition of the alternative complement pathway is sufficient to reduce damage (or enhance recovery) resulting from TBI or spinal cord injury (SCI). More particularly, the present inventors disclose herein the discovery that inhibition of the alternative pathway inhibits physiological damage (e.g., brain damage) in an experimental model of TBI, and also inhibits damage (measured by enhanced recovery) in an experimental model of SCI. Accordingly, the present invention relates to compounds, compositions and the use of such compounds or compositions in methods for the prevention and/or treatment of TBI, SCI or other neuronal or brain damage, through the selective inhibition of the alternative complement pathway.

First, the present inventors have shown for the first time a major role of the alternative pathway of complement activation in contributing to the overall extent of posttraumatic complement activation and to secondary neuronal cell death after brain injury. Furthermore, the inventors have demonstrated that specific inhibition of the alternative complement pathway by inhibition of factor B, in addition to general inhibition of the complement pathway through inhibition of C3 using a C3 complement convertase inhibitor, Crry-Ig, both inhibit damage associated with TBI. This is believed to be the first disclosure of the ability to inhibit physiological damage and effects associated with TBI by specifically and selectively inhibiting the alternative complement system.

Second, the present inventors have shown that inhibition of the alternative complement pathway through the inhibition of factor B inhibits damage associated with SCI. This is believed to be the first disclosure of the ability to inhibit physiological damage and effects associated with SCI by specifically and selectively inhibiting the alternative complement system.

The identification of factor B and the other proteins in the alternative complement pathway (e.g., factor D or properdin) as specific therapeutic targets provides a rational strategy as well as lead compounds that can be used to inhibit physiological damage or effects resulting from TBI or SCI via selective inhibition of the alternative complement pathway.

Several inhibitors have already been developed to inhibit the complement system at various stages of activation (Holers, V. M. 2003, *Clin Immunol* 107:140-151), although specific inhibitors of the alternative pathway have not been widely reported. Specific inhibition of the alternative pathway has several advantages compared with existing inhibitors of the complement cascade. First, because the present inventors have discovered that physiological damage due to TBI or SCI is primarily mediated by the alternative pathway of complement activation, a specific inhibitor of this pathway will be equally effective as a pan-complement inhibitor, yet should have fewer immunosuppressive side-effects. Furthermore, C4−/− mice (mice lacking the C4 complement component that is generic to the classical, alternative and lectin complement pathways), but not fB−/− (factor B deficient) mice, appear more susceptible to systemic experimental bacterial infection, which suggests that by leaving the classical pathway intact, an inhibitor of the alternative pathway poses less risk for serious infection. Although only one human patient with congenital deficiency of factor B has been reported (Densen et al., 1996, *Mol Immunol* 33:68 (Abstract 270)), studies of gene targeted factor B deficient mice (fB−/−) have not yet demonstrated an immune-modulating effect for this factor (Densen et al., supra; Matsumoto et al., 1997, *Proc Natl Acad Sci USA* 94:8720-8725). Patients with congenital deficiencies of classical pathway components, in contrast, appear to have an increased risk of infection (most commonly *Staphylococcus* and *Streptococcus*). Inhibition of classical pathway components or C3 (common to all of the complement pathways) might also be associated with autoimmunity (Figueroa and Densen, 1991, *Clin Microbiol Rev* 4:359-395), perhaps explaining why factor B deficiency protects MRL/lpr mice from developing glomerulonephritis, but C3 deficiency does not (Watanabe et al, supra). Selective inhibition of the alternative pathway prevents generation of C3-derived ligands for the C3a receptor as well as for complement receptors 1-4 and C5a. The effects of blocking of the alternative pathway may in fact be more direct, due to as yet poorly characterized receptors for the Ba or Bb activation products of factor B that are generated during the activation process. Thus, inhibition of the alternative pathway is expected to be better tolerated and more effective than classical pathway complement inhibition.

Given the great potential therapeutic benefit of an inhibitor specific for the alternative complement pathway for use in the methods of the present invention for treatment of TBI and SCI and related conditions, the present inventors have developed several inhibitory monoclonal antibodies directed against factor B and have tested one of them in an experimental model of TBI and also in an experimental model of SCI. These antibodies are described in detail in U.S. Patent Application Publication No. 2005-0260198-A1, published Nov. 24, 2005 and in PCT Publication No. WO 2005/077417, published Aug. 25, 2005, each of which is incorporated herein by reference in its entirety.

Figure 2A:
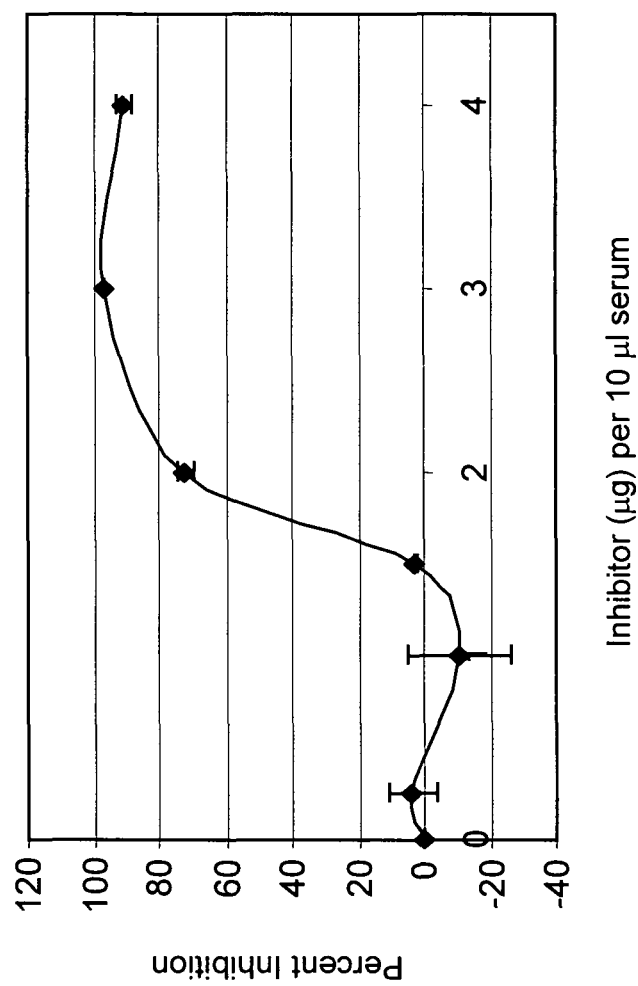
FIG. 2A is a line graph showing that anti-factor B completely inhibited the alternative complement pathway in a zymosan assay when 3 μg were added to a reaction containing 10 μl of serum.
Figure 2B:
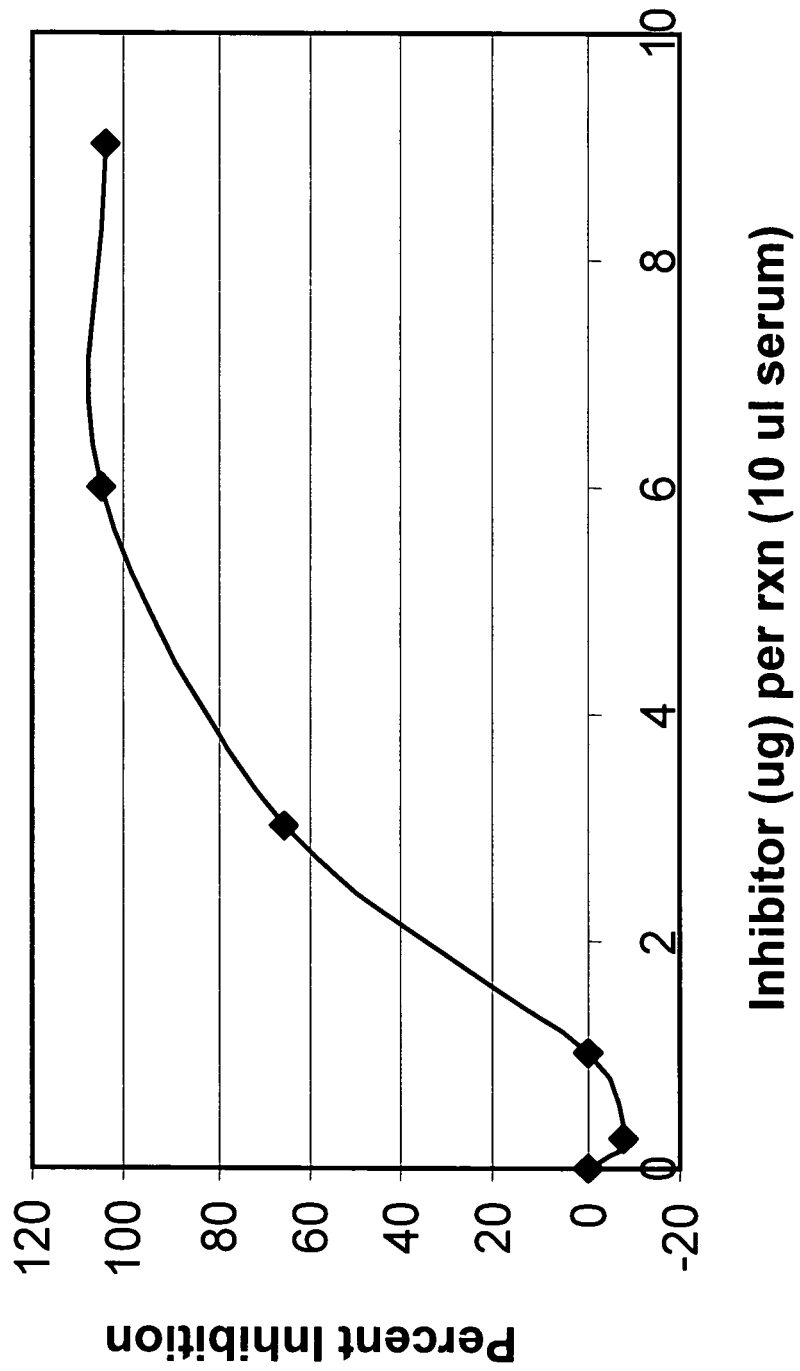
FIG. 2B is a line graph showing that anti-factor B completely inhibited the alternative complement pathway in a rabbit erythrocyte lysis assay when 6 μg of antibody were added to 10 μl of human serum.
Figure 3:
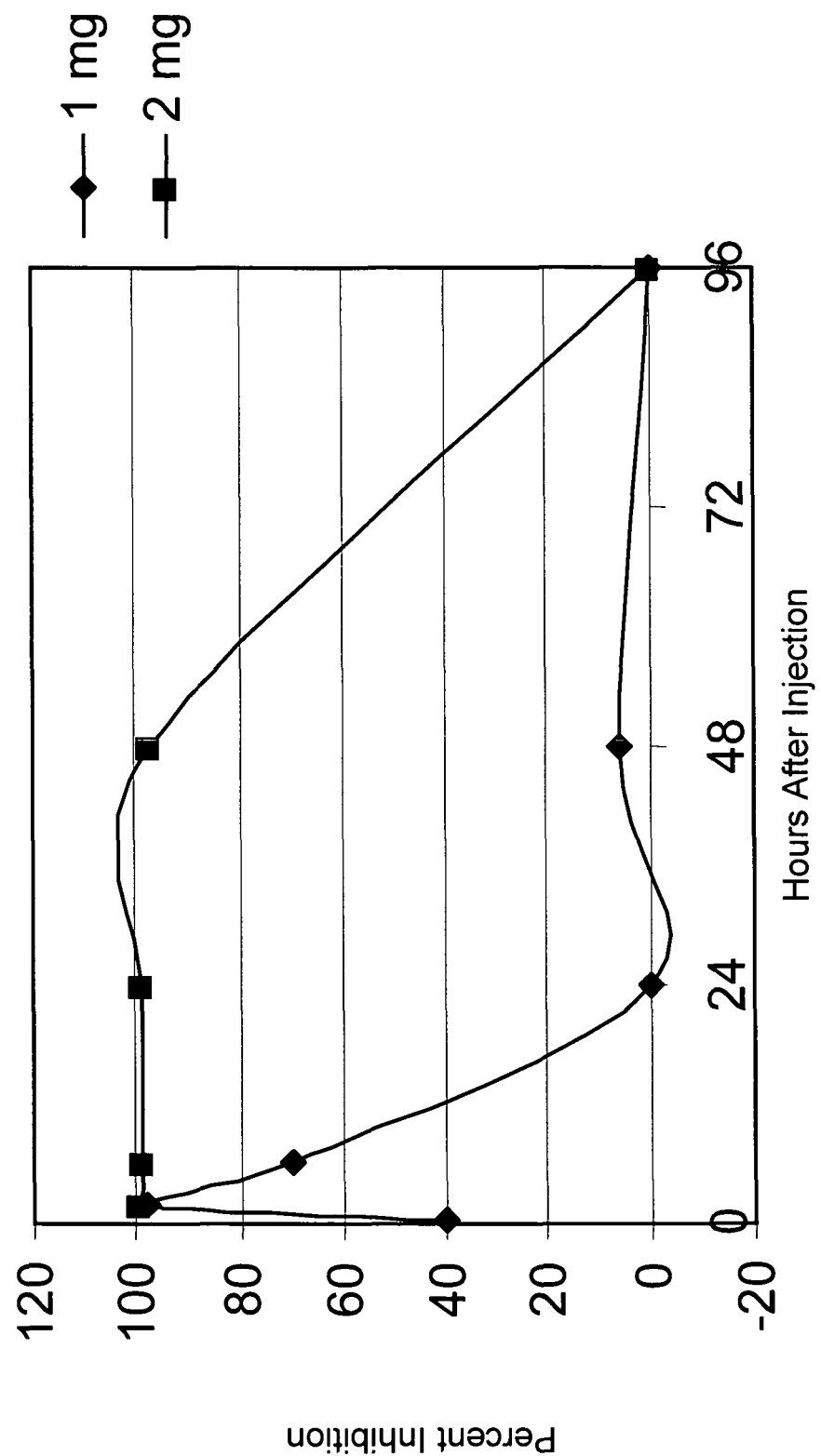
FIG. 3 is a line graph showing that administration of anti-factor B to mice inhibits the alternative complement pathway.

Briefly, to produce the antibodies, gene targeted factor B-deficient mice (fB−/−) were injected with a fusion protein comprised of the second and third short consensus repeat (SCR) domains of factor B linked to the hinge, CH2, and CH3 domains of a mouse IgG1 isotype (see FIG. 1). These SCR domains were chosen because they are part of the deleted segment of the factor B gene in the fB−/− mice. Mice were screened for an immune response to factor B (e.g., using ELISA), and spleen cells from one of the injected mice were fused to myeloma cells. One of the resulting hybridomas, named 1379, produces an IgG$_1$ antibody that inhibits alternative complement pathway activation in vitro (FIGS. 2A and 2B) and in vivo (FIG. 3). Specifically, this antibody was tested in two in vitro assays of alternative pathway activity (FIGS. 2A and 2B), and showed that the antibody can completely inhibit the lysis of erythrocytes by human serum, thus confirming the ability of this reagent to completely block alternative complement pathway activation. When mice were tested for inhibition of the alternative pathway at various times after a single injection of the inhibitory antibody, 1 mg of antibody led to full inhibition within one hour when injected IV and within two hours when injected IP (FIG. 3). Mice receiving a one mg injection IP retained full inhibition of the alternative pathway at 24 hours and those receiving a two mg injection retained full inhibition up to 48 hours after the injection. The inventors have also injected 2 mg of the 1379 antibody repetitively i.p. every other day for 14 days and have shown that the complete inhibition of the alternative complement pathway was maintained for at least 48 hours after the last injection. Moreover, Fab fragments made from this antibody also resulted in complete inhibition of the alternative pathway in approximately equimolar levels as with the intact 1379 antibody.

The 1379 antibody inhibits alternative pathway activation in serum from animals including, mice, rats, humans, baboons, rhesus monkeys, cyno monkeys, pigs, rabbits, and horses (Table 1).

TABLE 1

| Species in which the alternative pathway is fully inhibited by mAb 1379 |
|---|
| Mouse |
| Human |
| Rat |
| Baboon |
| Rhesus |
| Pig |
| Cyno Monkey |
| Horse |
| Species in which the alternative pathway is not inhibited by mAb 1379 |
| Dog |
| Guinea Pig |

A panel of anti-factor B antibodies produced by the inventors is shown in Table 2. As discussed above, the inventors have shown that the mAb 1379 both binds and inhibits mouse and human factor B. In contrast, the mAb designated 624 can bind both mouse and human factor B, but does not inhibit the human alternative pathway. As revealed in a competition assay, antibodies 624, 691, and 1231 do not block binding by 1379. These antibodies must therefore bind the protein at a different site, explaining why they bind factor B without inhibiting its function in vitro. However, antibodies 395, 1322 and 1060 are competitive inhibitors of 1379.

TABLE 2

| Clone | Isotype | Binds mouse fB | Binds human fB | Inhibits mouse alternative pathway (zymosan assay) | Inhibits human alternative pathway (rabbit erythrocyte lysis assay) | Competes with 1379 for human fB binding |
|---|---|---|---|---|---|---|
| 1379 | IgG1 κ | +++ | +++ | +++ | +++ | +++ |
| 395 | IgG1 κ | +++ | ++ | ++ | +++ | +++ |
| 1322 | IgG2b κ | +++ | +++ | + | ++ | +++ |
| 624 | IgG1 κ | +++ | +++ | + | − | − |
| 691 | IgG1 κ | +++ | +++ | + | − | − |
| 1060 | IgG2b κ | +++ | +++ | + | ++ | ++ |
| 1231 | IgG1 | +++ | +++ | + | − | − |
| E1128 | | − | +++ | − | 0 | NA |

Epitope mapping was used to demonstrate that this antibody binds to factor B within the third short consensus repeat (SCR) domain, and the antibody prevented formation of the C3bBb complex. In addition, experiments to map the epitope for the mAb1379 antibody indicated that the epitope or antibody binding site on factor B was not linear. Experiments demonstrated that the introduction of certain alanine substitutions into SCRs 2 and 3 of human factor B, but not SCR1, resulted in the loss or substantial loss of binding of the 1379 antibody to factor B, which included mutants that substituted: 139-Tyr-140-Cys-141-Ser with His-Cys-Pro (the positions being relevant to the mature human factor B represented by SEQ ID NO:2); and 182-Glu-183-Gly-184-Gly-185-Ser with Gly-Asn-Gly-Val.

Figure 4:
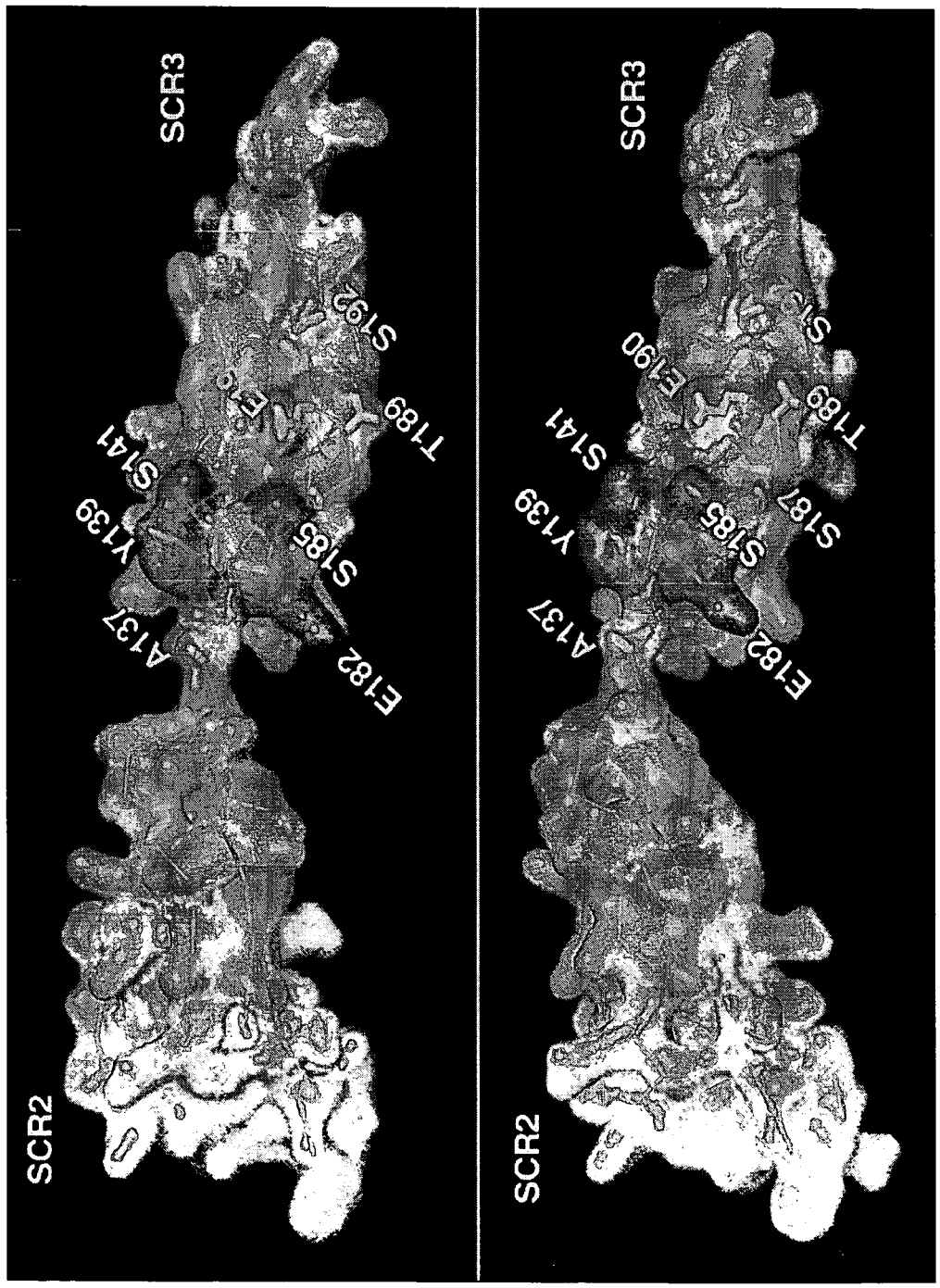
FIG. 4 is a schematic drawing showing a model of the epitope mapping for mAb1379 on the human factor B surface.
Figure 5:
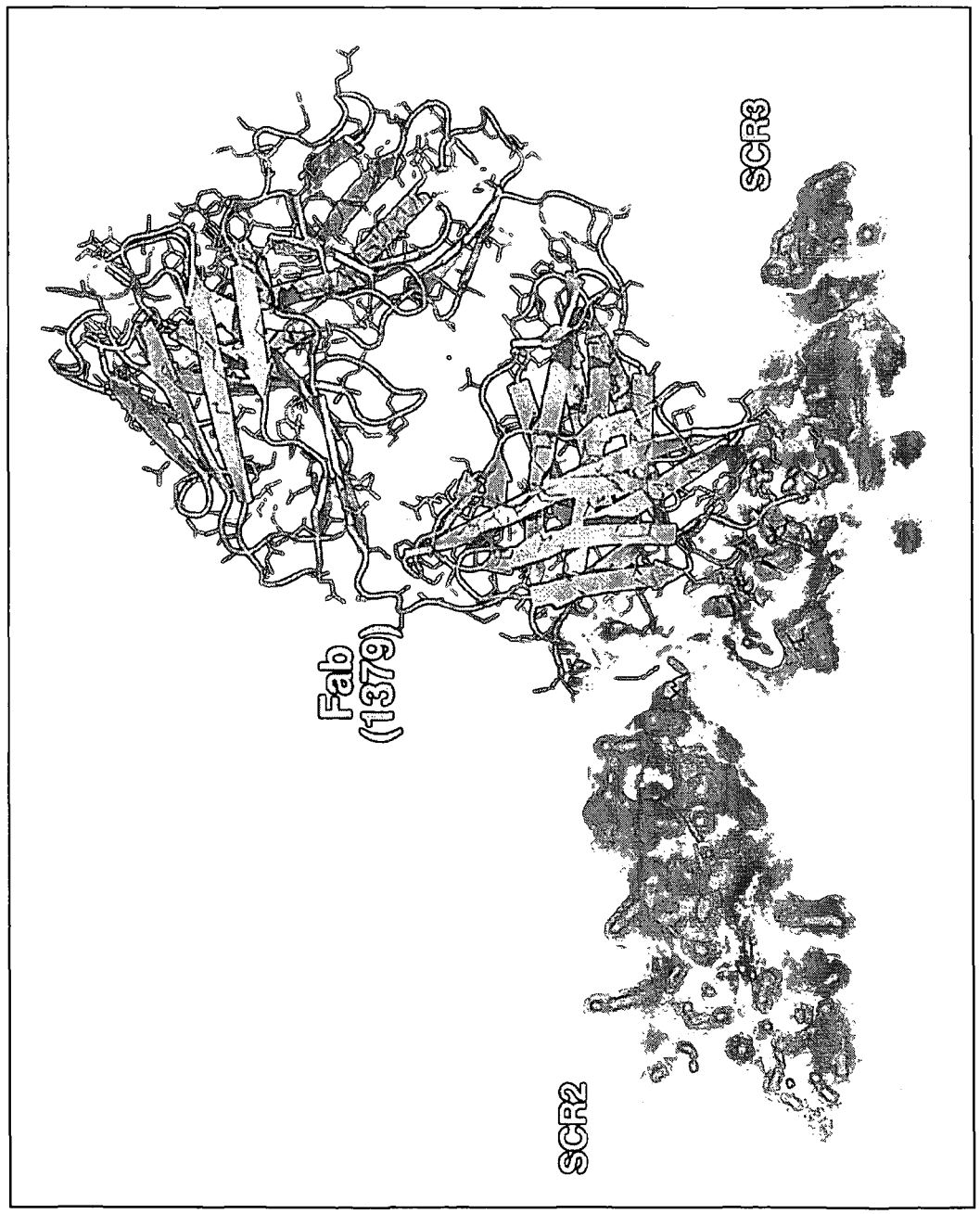
FIG. 5 is a schematic drawing showing a modeled complex of mAB1379 (one Fab fragment) binding to factor B, with the antigen binding sides of the Fab having been modeled to cover the entire mapped epitope region.

The predicted conserved binding surface or epitope of the human factor B that is recognized by mAb1379 was modeled. Briefly, the tertiary structure of human factor B was built based on the resolved three-dimensional structure of CR2-SCR1-2 (Protein Data Bank (PDB) id 1GHQ). FIG. 4 shows the model of the factor B structure with the amino acid positions corresponding to the mAb1379 epitope (relative to SEQ ID NO:2) indicated. The residues that are believed to form the conformational epitope for the mAb1379 antibody are: Ala137, Tyr139, Ser141, Glu182, Ser185, Thr189, Glu190, and Ser192, although the epitope may contain only a few, substantially all, or more residues than is depicted in FIG. 4. FIG. 5 is a schematic drawing showing a modeled complex of mAB1379 (one Fab fragment) binding to factor B, with the antigen binding sides of the Fab having been modeled to cover the entire mapped epitope region as defined above in FIG. 4.

The antibodies that have been produced by the present inventors, described in more detail in U.S. Patent Application Publication No. 2005-0260198-A1 and in PCT Publication No. WO 2005/077417, supra, recognize a site on factor B that is shared among humans and many other animal species in which pre-clinical proof-of-principle experiments are performed, thus allowing discoveries in models of human disease to be readily translated into human therapies. These antibodies are believed to be the first antibodies against factor B that exhibit the broad species inhibition of the protein. Therefore, a unique site has also been identified on factor B against which new inhibitory reagents can be developed.

In the present invention, the inventors have discovered and report for the first time herein that inhibition of the alternative pathway inhibits physiological damage in traumatic brain injury (TBI), and also inhibits physiological damage in spinal cord injuray (SCI) and this information can now be used to design, isolate and/or identify novel therapeutic reagents for the treatment of TBI and SCI. Moreover, the antibodies previously produced and described by the inventors are excellent agents for use in the methods of the present invention.

One embodiment of the present invention relates to a method to reduce or prevent at least one symptom or condition (disability, impairment, physiological damage) resulting from (associated with) traumatic brain injury (TBI) in an animal to or enhance (increase) the recovery from damage caused by TBI, comprising selectively inhibiting the alternative complement pathway in an animal that has experienced TBI. Another embodiment of the invention relates to a method to reduce or prevent at least one symptom or condition (disability, impairment, physiological damage) resulting from (associated with) spinal cord injury (SCI) in an animal or enhance (increase) the recovery from damage caused by SCI, comprising selectively inhibiting the alternative complement pathway in an animal that has experienced SCI. In one preferred embodiment, the method includes administering to the animal an agent that inhibits the alternate complement pathway, and particularly, an agent that inhibits factor B. In one particularly preferred embodiment, the agent is an anti-factor B antibody or an antigen binding fragment thereof.

Accordingly, the methods of the present invention include a step of selectively inhibiting the alternative complement pathway in an animal that has, or is at risk of developing, physiological damage due to TBI or SCI, respectively. According to the present invention, to inhibit the alternative complement pathway in an animal refers to inhibiting the expression and/or the biological activity of at least one protein or nucleic acid molecule encoding such protein that is part of the alternative complement pathway. Such proteins include, but are not limited to, factor B, factor D or properdin. To "selectively" inhibit the alternative complement pathway means that the method of the present invention preferentially or exclusively inhibits the alternative complement pathway, but does not inhibit or at least does not substantially inhibit other pathways for complement activation, including the classical complement pathway or the lectin pathway. For example, the novel factor B antibodies and antigen binding fragments thereof of the present invention are one example of a reagent that selectively inhibits the alternative complement pathway. To "selectively" inhibit a specific protein means that the method of the present invention preferentially or exclusively inhibits the expression and/or a biological activity of the specific protein, but does not inhibit or at least does not substantially inhibit the expression and/or a biological activity of other proteins (unless such biological activity is one that is shared, such as a downstream event, with the specific protein).

According to the present invention, traumatic brain injury (TBI) is defined as any injury, wound, or damage caused by any type of trauma to the head, such as impact to the head or shaking. More specifically, TBI is an acquired injury to the brain caused by an external physical force, resulting in total or partial functional disability or psychosocial impairment, or both. The term applies to open and closed head injuries resulting in impairments in one or more areas, such as cognition; language; memory; attention; reasoning; abstract thinking; judgment; problem-solving; sensory, perceptual, and motor abilities; psychosocial behavior; physical functions; information processing; and speech. The term typically does not apply to brain injuries that are congenital or degenerative, or brain injuries induced by birth trauma, although the latter type of trauma may also be treated using the method of the invention. TBI can result in a variety of physiological and psychological symptoms, conditions or impairments, including physical impairments (e.g., speech, vision, hearing and other sensory impairment; headaches; lack of fine motor coordination; spasticity of muscles; paresis or paralysis of one or both sides and seizure disorders; balance impairments; and other gait impairments), cognitive impairments (e.g., short- and long-term memory deficits, impaired concentration, slowness of thinking and limited attention span, as well as impairments of perception, communication, reading and writing skills, planning, sequencing, and judgment), and psychosocial-behavioral-emotional impairments (e.g., fatigue, mood swings, denial, self-centeredness, anxiety, depression, lowered self-esteem, sexual dysfunction, restlessness, lack of motivation, inability to self-monitor, difficulty with emotional control, inability to cope, agitation, excessive laughing or crying, and difficulty relating to others). A detailed discussion of the diagnosis of TBI has been presented above.

Methods for diagnosing TBI are well-established in the art. Typically, TBI is diagnosed by the history of trauma, the clinical status and imaging studies, such as x-rays and computerized tomography (CT) scan. Of particular importance is the use of the post-resuscitation Glasgow Coma Scale (GCS) score (Teasdale and Jennett, 1974, *Lancet* 2 (7872):81-84), since this parameter represents an important predictor of outcome. When assessing the GCS, the best response is used to calculate the score. Patients with mild head injury (GCS 14 or 15) represent about 80% of all head trauma patients admitted to the emergency department. Moderate head injury corresponds to a GCS score between 9 and 13 and is associated with an increased risk for intracranial pathology compared to patients with mild head injury. A GCS score of 8 points or less corresponds to a comatose patient, as defined by the inability to open the eyes, to obey commands and to respond verbally.

Thus, severe head injury is defined as a GCS score of 3 to 8. When evaluating the patient, in addition to the GCS and assessment of the level of consciousness, a neurologic exam typically includes the assessment of pupillary size and reactivity and a brief evaluation of peripheral motor function. The clinical exam furthermore includes the inspection of the scalp for lacerations, palpation of the skull for impression fractures and the search for indirect signs of basilar skull fractures, including periorbital ecchymosis ("racoon eyes"), retroauricular ecchymosis ("Battle's sign"), rhinorrhoea/otorrhoea due to CSF leakage, and VII$^{th}$ nerve palsy. Under certain circumstances, a CT scan is given. Other causes of coma or altered state of consciousness may be investigated in the analysis, such as by screening for: drugs, metabolic dysfunction, internal or external bleeding sources, preexisting non-traumatic brain damage (e.g., ischemic or hemorrhagic brain injury), epilepsy, basilar artery thrombosis, bacterial meningitis, brain abscess or tumor. Morphological classification of closed head injury is based on findings in the CT scan according to the guidelines of Marshall and colleagues (Marshall et al., *J. Neurosurg.* 1991, 75:S14-S20). Intracranial lesions may be either focal (subdural, epidural, intracerebral bleeding; "evacuated" vs. "nonevacuated") or diffuse (grade I-IV). Detailed discussions of parameters used to evaluate TBI are described, for example, in Vos et al., 2002, *Eur. J. Neurol.* 9:207-219 and Gaetz, 2004, *Clin. Neurophysiol.* 115:4-18.

According to the present invention, spinal cord injury (SCI) is defined as any injury, wound, or damage to the spinal cord that results in a loss of function, such as mobility or feeling. Frequent causes of damage are trauma (e.g., by car accident, gunshot, falls, etc.) or disease (polio, spina bifida, Friedreich's Ataxia, etc.). The spinal cord does not have to be severed in order for a loss of functioning to occur. In most individuals with SCI, the spinal cord is intact, but the damage results in loss of function. Besides a loss of sensation or motor function, individuals with SCI may also experience symptoms, conditions, or impairments including dysfunction of the bowel and bladder, sexual and fertility dysfunction, inability to regulate blood pressure effectively, reduced control of body temperature, inability to sweat below the level of injury, and chronic pain. A patient with SCI can have any level of SCI, as typically defined by the level of the damage (e.g., at or below any of the eight cervical vertebrae or the twelve thoracic vertebrae). Very high injuries (C-1, C-2) can result in a loss of many involuntary functions including the ability to breathe, necessitating breathing aids such as mechanical ventilators or diaphragmatic pacemakers.

Methods for diagnosing spinal cord injury are well-established in the art. In the emergency room, a doctor may be able to rule out spinal cord injury by carefully inspecting an injured person, testing for sensory function and movement, and asking questions about an accident. If the injured person complains of neck pain, isn't fully awake, or has obvious signs of weakness or neurologic injury, emergency diagnostic tests may be needed. Such tests may include, X-rays, computerized tomography (CT) scan, magnetic resonance imaging (MRI), or myelography. Various neurological examinations may also be performed. The effects of SCI depend on the type of injury and the level of the injury. SCI can be generally divided into two types of injury—complete and incomplete. A complete injury means that there is no function below the level of the injury (i.e., no sensation and no voluntary movement). Both sides of the body are equally affected. An incomplete injury means that there is some functioning below the primary level of the injury. A person with an incomplete injury may be able to move one limb more than another, may be able to feel parts of the body that cannot be moved, or may have more functioning on one side of the body than the other. With the advances in acute treatment of SCI, incomplete injuries are becoming more common.

The level of injury is very helpful in predicting what parts of the body might be affected by paralysis and loss of function in SCI. Cervical (neck) injuries usually result in quadriplegia. Injuries above the C-4 level may require a ventilator for the person to breathe. C-5 injuries often result in shoulder and biceps control, but no control at the wrist or hand. C-6 injuries generally yield wrist control, but no hand function. Individuals with C-7 and T-1 injuries can straighten their arms but still may have dexterity problems with the hand and fingers. Injuries at the thoracic level and below result in paraplegia, with the hands not affected. At T-1 to T-8 there is most often control of the hands, but poor trunk control as the result of lack of abdominal muscle control. Lower T-injuries (T-9 to T-12) allow good truck control and good abdominal muscle control. Sitting balance is very good. Lumbar and Sacral injuries yield decreasing control of the hip flexors and legs. Persons with tetraplegia have sustained injuries to one of the eight cervical segments of the spinal cord; those with paraplegia have lesions in the thoracic, lumbar, or sacral regions of the spinal cord.

The present invention is directed to inhibiting the physiological damage and the symptoms or conditions (disabilities, impairments) associated with such damage, that result from TBI or SCI as described in detail above. As such, it is not required that physiological damage or all effects of the condition be entirely prevented or reversed, although the effects of the present method likely extend to a significant therapeutic benefit for the patient. As such, a therapeutic benefit is not necessarily a complete prevention or cure for a particular condition or physiological damage resulting from TBI or SCI, but rather, can encompass a result which includes reducing or preventing the symptoms or physiological damage that result from TBI or SCI, reducing or preventing the occurrence of such symptoms or damage (either quantitatively or qualitatively), reducing the severity of such symptoms or physiological effects, and/or enhancing the recovery of the patient after experiencing TBI or SCI. Specifically, a composition of the present invention, when administered to a patient, preferably prevents damage associated with the brain injury or spinal cord injury and/or reduces or alleviates symptoms of or conditions associated with (resulting from) the damage, signs of the damage or even the causes of the damage, as well as enhances recovery from the damage. As such, to protect a patient from the physiological effects or symptoms resulting from TBI or SCI (or related conditions) includes both preventing or reducing the occurrence and/or severity of the effects of the damage and treating a patient in which the effects of the damage are already occurring or beginning to occur. A beneficial effect can easily be assessed by one of ordinary skill in the art and/or by a trained clinician who is treating the patient. For example, many of the methods described above for the diagnosis of TBI or SCI can be used to evaluate the patient before and after treatment using a method of the present invention to assess the success of the treatment. Preferably, there is a positive or beneficial difference in the severity or occurrence of at least one clinical or biological score, value, or measure used to evaluate such patients in those who have been treated according to the present invention as compared to those that have not.

Inhibition of the alternative complement pathway according to the present invention for the purposes of inhibiting the physiological damage, and the symptoms or conditions (disabilities, impairments) associated with such damage, that result from TBI or SCI, can be accomplished by directly affecting the expression (transcription or translation) or biological activity of a protein in the alternative complement pathway, or by directly affecting the ability of a protein to bind to a protein in the alternative complement pathway or to otherwise contribute to the activation of complement via the alternative pathway. More specifically, in one embodiment, expression of a protein refers to either the transcription of the protein or the translation of the protein. Therefore, the method of the present invention can inhibit the transcription and/or the translation of a protein in the animal that naturally expresses the protein (e.g., by administering an agent that inhibits the expression of the protein and genetically modifying an animal to have reduced protein expression). In another embodiment, inhibition of the alternative complement pathway is defined herein as any measurable (detectable) reduction (i.e., decrease, downregulation, inhibition) of the activity of the pathway, such as by any measurable reduction in the expression and/or biological activity of a protein within the alternative complement pathway, and can include blocking or inhibiting the ability of a protein or molecule to act in the alternative complement pathway.

Methods for inhibiting the expression of a protein include, but are not limited to, administering an agent that inhibits the expression of the protein (directly or indirectly), and genetically modifying an animal to have reduced protein expression (e.g., note the fB−/− mice used herein). Preferably, protein expression is inhibited by administration of an agent (reagent, compound, drug) to the animal that directly inhibits protein expression. Such agents include, but are not limited to: a ribozyme or RNAi that is specific for RNA encoding the protein; a DNA binding protein or a drug that binds to a gene or RNA encoding the protein and inhibits expression of the protein; an aptamer that binds to the protein; a protein or drug that binds to the protein intracellularly and prevents secretion of the protein by the cell which expresses it; and, an isolated nucleic acid molecule that reduces expression of the protein by hybridizing under high stringency conditions to a gene encoding the protein in a cell of the animal (e.g., an anti-sense nucleic acid molecule). Such compounds that selectively inhibit expression of a protein can be produced using techniques known to those of skill in the art.

Accordingly, the method of the present invention includes the use of a variety of agents (i.e., regulatory compounds) which, by acting directly on a protein in the alternative complement pathway, selectively inhibit the expression and/or biological activity of one or more proteins in the alternative complement pathway such that physiological damage associated with TBI or SCI is reduced in an animal. Agents useful in the present invention include, for example, proteins, nucleic acid molecules, antibodies, and compounds that are products of rational drug design (i.e., drugs). Such agents are generally referred to herein as inhibitors.

According to the present invention, an inhibitor is any agent which inhibits, either by direct inhibition or competitive inhibition, the expression and/or biological activity of a protein (e.g., a protein in the alternative complement pathway), and includes agents which act on factor B, factor D or properdin. In one embodiment of the present invention, inhibition of the alternative complement pathway or a protein of the alternative complement pathway is defined herein as any measurable (detectable) reduction (i.e., decrease, downregulation, inhibition) of the biological activity of a protein in the alternative complement pathway. The biological activity or biological action of a protein refers to any function(s) exhibited or performed by a naturally occurring form of the protein as measured or observed in vivo (i.e., in the natural physiological environment of the protein) or in vitro (i.e., under laboratory conditions). For example, a biological activity of factor B can include, but is not limited to, binding to activated C3, solubilization of immune complexes, B cell growth factor activity, and monocyte activation. A biological activity of factor D can include, but is not limited to, catalysis of the cleavage of factor B when in complex with C3, catalysis of the formation of Ba and Bb. A biological activity of properdin can include, but is not limited to, binding to and stabilizing cell- or immune complex-bound C3bBb and stabilizing the C3/C5 convertase.

According to the present invention, the biological activity of a protein can be inhibited by directly preventing or inhibiting (reducing, decreasing) the ability of the protein to bind to and/or activate another protein (e.g., C3), thereby inhibiting downstream events resulting from such binding. Preferably, the biological activity of the alternative complement pathway is inhibited by administering an agent that inhibits at least one protein in the pathway, such agent including, but not limited to, an agent that binds to a protein in the pathway or competes with the protein in the pathway in a manner that the ability of the protein to bind to and/or activate another protein is inhibited or prevented.

Agents that inhibit a protein in the alternative complement pathway can include, but are not limited to, compounds that are products of rational drug design, natural products, and compounds having partially defined regulatory properties. A regulatory agent, including an antagonist of a given protein, can be a protein-based compound, a carbohydrate-based compound, a lipid-based compound, a nucleic acid-based compound, a natural organic compound, a synthetically derived organic compound or drug, an antibody (including antigen-binding fragments thereof), or fragments thereof. One particular type of agent useful in the present invention is an antagonist of the alternative complement pathway, including an antagonist of a protein within this pathway. According to the present invention, an "antagonist" refers to any compound that inhibits (e.g., antagonizes, reduces, decreases, blocks, reverses, or alters) the effect of a given protein. More particularly, an antagonist is capable of acting in a manner relative to the given protein's activity, such that the biological activity of the given protein is decreased or blocked in a manner that is antagonistic (e.g., against, a reversal of, contrary to) to the natural action of the given protein. Antagonists can include, but are not limited to, an antibody or antigen binding fragment thereof, a protein, peptide, nucleic acid (including ribozymes and antisense), or a product of drug/compound/peptide design or selection that provides the antagonistic effect. For example, the present invention includes any antagonists of the natural proteins, factor B, factor D or properdin, including antibody antagonists, protein/peptide antagonists, nucleic acid antagonists, or small molecule antagonists (e.g., a small molecule inhibitor).

In one embodiment, regulatory agents of the present invention include drugs, including peptides, oligonucleotides, carbohydrates and/or synthetic organic molecules that regulate the production and/or function of one or more proteins in the alternative complement pathway. Such an agent can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, *Molecular Biotechnology: Therapeutic Applications and Strategies*, Wiley-Liss, Inc., which is incorporated herein by reference in its entirety.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., supra.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential regulatory agents by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

Various other methods of structure-based drug design are disclosed in Maulik et al., 1997, supra. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

An isolated nucleic acid molecule that is useful as an agent for inhibiting a protein (or its expression) in the alternative complement pathway is an anti-sense nucleic acid molecule, a ribozyme, siRNA, or an aptamer. As used herein, an anti-sense nucleic acid molecule is defined as an isolated nucleic acid molecule that reduces expression of a protein by hybridizing under high stringency conditions to a gene encoding the protein. Such a nucleic acid molecule is sufficiently similar to the gene encoding the protein that the molecule is capable of hybridizing under high stringency conditions to the coding or complementary strand of the gene or RNA encoding the natural protein. RNA interference (RNAi) is a process whereby double stranded RNA, and in mammalian systems, short interfering RNA (siRNA), is used to inhibit or silence expression of complementary genes. In the target cell, siRNA are unwound and associate with an RNA induced silencing complex (RISC), which is then guided to the mRNA sequences that are complementary to the siRNA, whereby the RISC cleaves the mRNA. A ribozyme is an RNA segment that functions by binding to the target RNA moiety and inactivate it by cleaving the phosphodiester backbone at a specific cutting site. Aptamers are short strands of synthetic nucleic acids (usually RNA but also DNA) selected from randomized combinatorial nucleic acid libraries by virtue of their ability to bind to a predetermined specific target molecule with high affinity and specificity. Aptamers assume a defined three-dimensional structure and are capable of discriminating between compounds with very small differences in structure.

A gene includes regulatory regions that control production of the protein encoded by that gene (such as, but not limited to, transcription, translation or post-translation control regions) as well as the coding region itself. The genes encoding various proteins of the alternative complement pathway, including factor B, factor D or properdin, have been identified and are known in the art. An isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated nucleic acid molecule of the present invention can be isolated from its natural source or produced using recombinant DNA technology (e.g., polymerase chain reaction (PCR) amplification, cloning) or chemical synthesis.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

In a preferred embodiment of the present invention, the agent used for inhibiting a protein of the alternative complement pathway for the purpose of inhibiting the physiological damage that results from TBI or SCI (and the symptoms or conditions (disabilities, impairments) associated with such damage), is an antibody or an antigen binding fragment thereof. Similarly, an antigen binding polypeptide is also particularly preferred for use in the present invention. In one aspect, the antibody selectively binds to the protein of the alternative complement pathway in a manner such that the protein is inhibited or prevented from binding to another protein with which it normally (under natural or physiological conditions) interacts. In another aspect, the antibody selectively binds to the protein in a manner such that the protein is inhibited or prevented from activating another protein with which it normally interacts, even though the protein may at least partially bind to the other protein. Particularly preferred antibodies and antigen binding fragments thereof for use in selective inhibition of the alternative complement pathway for the purpose of inhibiting the physiological damage that results from TBI or SCI are described in detail below (e.g., the factor B antibodies described herein, and particularly, the mAb1379 antibody described in detail herein).

Preferably, an antibody or antigen binding fragment thereof useful in the present invention binds to a protein selected from factor B, factor D or properdin. Most preferably, the invention includes an antibody or antigen binding fragment thereof that binds to factor B, and its use for the purpose of inhibiting the physiological damage that results from TBI or SCI. Antibodies (and antigen binding fragments thereof) that selectively bind to factor B and inhibit the alternative complement pathway according to the invention are described and exemplified in detail herein. In one embodiment, the antibody or antigen binding fragment thereof binds to a conserved binding surface or epitope of such a protein (e.g., factor B) that is conserved among animal species, and particularly mammalian, species (i.e., the antibody is cross-reactive with the protein from two or more different mammalian species). In particular, the present invention includes an antibody that binds to factor B from at least two, and preferably, several different mammalian species, including, but not limited to, human, non-human primate, mouse, rat, pig, horse and rabbit. Preferably, the present invention includes an antibody that binds to factor B from human and at least one additional animal species, and preferably, at least one additional mammalian species, including, but not limited to, non-human primate, mouse, rat, pig, horse and rabbit. In one embodiment, the antibody or antigen binding fragment thereof binds to the third short consensus repeat (SCR) of factor B. In one embodiment, the antibody or antigen binding fragment thereof binds to a region of factor B that prevents the cleavage of factor B by factor D. In one embodiment, the antibody is a monoclonal antibody. In one embodiment, the antibody is the antibody referred to herein as 1379 (i.e., the antibody produced by the hybridoma cell line of the same number, also having ATCC Deposit Designation PTA-6230), or an antigen binding fragment thereof.

The hybridoma described herein as 1379 (or mAb1379) was deposited on Sep. 21, 2004, with the American Type Culture Collection (ATCC, located at 10801 University Blvd, Manassas, Va. 20110-2209), under the terms of the Budapest Treaty on the International Recognition of The Deposit of Microorganisms For the Purposes of Patent Procedure, and has received ATCC Deposit Designation PTA-6230.

According to the present invention, the minimum size of a protein, portion of a protein (e.g. a fragment, portion, domain, etc.), or region or epitope of a protein, is a size sufficient to serve as an epitope or conserved binding surface for the generation of an antibody or as a target in an in vitro assay. In one embodiment, a protein of the present invention is at least about 4, 5, 6, 7 or 8 amino acids in length (e.g., suitable for an antibody epitope or as a detectable peptide in an assay), or at least about 25 amino acids in length, or at least about 50 amino acids in length, or at least about 100 amino acids in length, or at least about 150 amino acids in length, and so on, in any length between 4 amino acids and up to the full length of a protein or portion thereof or longer, in whole integers (e.g., 8, 9, 10, . . . 25, 26, . . . 500, 501, . . . ).

The nucleotide sequence for the gene and coding region encoding human factor B and other complement proteins, as well as the amino acid sequence of such proteins, are well known in the art. For example, the gene encoding human factor B and other complement proteins is found in NCBI Database Accession No. NG_000013. The coding sequence for factor B is found in NCBI Database Accession No. NM_001710 and the amino acid sequence for factor B preproprotein is found in NCBI Database Accession No. NP_001701 or P00751. The amino acid sequence for NCBI Database Accession No. P00751, which is a human preproprotein factor B sequence, is represented herein by SEQ ID NO:1. Sequences from other animal species are also known in the art. By way of comparison, in the mouse factor B sequence (e.g., see NCBI Database Accession No. P04186, represented herein by SEQ ID NO:6), the third SCR domain is located at positions 160-217 of this 761 amino acid preprotein, and the mature murine factor B protein spans positions 23-761 of SEQ ID NO:6. The coding sequence for human factor D is found in NCBI Database Accession No. NM_001928.2 and the amino acid sequence for human factor D preproprotein is found in NCBI Database Accession No. NP_001919 (represented herein as SEQ ID NO:7). The coding sequence for human properdin is found in NCBI Database Accession No. NM_002621.1 and the amino acid sequence for human properdin is found in NCBI Database Accession No. NP_002612 (represented herein by SEQ ID NO:8).

The human factor B preprotein represented by SEQ ID NO:1 is a 764 amino acid protein with a signal peptide spanning from amino acid positions 1-25. The mature chain of factor B corresponds to positions 26-764 of SEQ ID NO:1 and is represented herein by SEQ ID NO:2. The three SCR regions of human factor B are represented herein by SEQ ID NO:3 (SCR1, also known as Sushi 1, spanning from about position 35 to about position 100 of SEQ ID NO:1 or from about position 5 to about position 75 of SEQ ID NO:2), SEQ ID NO:4 (SCR2, also known as Sushi 2, spanning from about position 101 to about position 160 of SEQ ID NO:1 or from about position 76 to about position 135 of SEQ ID NO:2), and SEQ ID NO:5 (SCR3, also known as Sushi 3, spanning from about position 163 to about position 220 of SEQ ID NO:1 or from about position 138 to about position 195 of SEQ ID NO:2).

Based on the epitope mapping of factor B using the fragments described by Hourcade, 1995, *J. Biol. Chem.*, in one preferred embodiment, an anti-factor B antibody useful in the present invention preferably binds to an epitope or conserved binding surface within or containing a part of the third SCR domain, and more preferably, to an epitope of human factor B that includes at least a portion of the sequence comprising from about position Tyr139 to about position Ser185 with respect to the mature factor B protein (SEQ ID NO:2), to an epitope of human factor B that includes at least a portion of the sequence comprising from about position Tyr139 to about position Ser141 with respect to the mature factor B protein (SEQ ID NO:2), to an epitope of human factor B that includes at least a portion of the sequence comprising from about position Glu182 to about position Ser185 with respect to the mature factor B protein (SEQ ID NO:2), to an epitope of factor B that includes at least a portion of human factor B (SEQ ID NO:2) comprising any one or more of the following positions or their equivalent positions in a non-human factor B sequence: Tyr139, Cys 140, Ser141, Glu182, Gly184, or Ser185, or to an epitope of factor B that includes at least a portion of the equivalent positions with respect to non-human animal species. One of skill in the art can readily align the sequence of human factor B with the sequence of factor B from another animal species and determine the positions of the SCR regions and the specific portions of the third SCR regions corresponding to the amino acid positions above. For example, two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174:247-250, incorporated herein by reference in its entirety.

Based on additional epitope modeling and mapping of an exemplary antibody useful in the invention, in another preferred embodiment, an anti-factor B antibody useful in the present invention preferably binds to an epitope (conserved binding surface) within or containing a part or portion of the third SCR domain of factor B that includes at least one or more of the following amino acid positions, with respect to SEQ ID NO:2, or their equivalent positions in a non-human factor B sequence: A137, Y139, S141, E182, S185, T189, E190, and S192. In one aspect of the invention, the epitope is within or containing a part of portion of the third SCR domain of factor B that includes all or substantially all of (at least five, six, or seven of the following amino acid positions of SEQ ID NO:2, or their equivalent positions in a non-human factor B sequence: Ala137, Tyr139, Ser141, Glu182, Ser185, Thr189, Glu190, and Ser192. In yet another aspect, the epitope recognized by an anti-factor B antibody useful in the present invention is within or contains a part or portion of the third SCR domain of factor B consisting of the following amino acid positions of SEQ ID NO:2, or their equivalent positions in a non-human factor B sequence: Ala137, Tyr139, Ser141, Glu182, Ser185, Thr189, Glu190, and Ser192.

In one embodiment, the epitope recognized by a factor B antibody useful in the invention can also be defined more particularly as being non-linear epitope located within the three-dimensional structure of a portion of the third SCR domain of factor B. The portion that contains the epitope is the three-dimensional structure of factor B that is defined by at substantially all of (e.g., at least about 90% of) amino acid positions Ala137-Ser192 of SEQ ID NO:2, or equivalent positions in a non-human factor B sequence, when such sequence is conformationally arranged as it occurs in the natural full-length factor B sequence. A model of the three-dimensional structure of factor B, which illustrates an epitope for mAb1379 is illustrated in FIG. 4 and FIG. 5, for example. As used herein, the "three dimensional structure" or "tertiary structure" of a protein refers to the arrangement of the components of the protein in three dimensions. Such term is well known to those of skill in the art. As used herein, the term "model" refers to a representation in a tangible medium of the three dimensional structure of a protein, polypeptide or peptide. For example, a model can be a representation of the three dimensional structure in an electronic file, on a computer screen, on a piece of paper (i.e., on a two dimensional medium), and/or as a ball-and-stick figure.

According to the present invention, an "epitope" of a given protein or peptide or other molecule is generally defined, with regard to antibodies, as a part of or site on a larger molecule to which an antibody or antigen-binding fragment thereof will bind, and against which an antibody will be produced. The term epitope can be used interchangeably with the term "antigenic determinant", "antibody binding site", or "conserved binding surface" of a given protein or antigen. More specifically, an epitope can be defined by both the amino acid residues involved in antibody binding and also by their conformation in three dimensional space (e.g., a conformational epitope or the conserved binding surface). An epitope can be included in peptides as small as about 4-6 amino acid residues, or can be included in larger segments of a protein, and need not be comprised of contiguous amino acid residues when referring to a three dimensional structure of an epitope, particularly with regard to an antibody-binding epitope. Antibody-binding epitopes are frequently conformational epitopes rather than a sequential epitope (i.e., linear epitope), or in other words, an epitope defined by amino acid residues arrayed in three dimensions on the surface of a protein or polypeptide to which an antibody binds. As mentioned above, the conformational epitope is not comprised of a contiguous sequence of amino acid residues, but instead, the residues are perhaps widely separated in the primary protein sequence, and are brought together to form a binding surface by the way the protein folds in its native conformation in three dimensions. The epitope recognized by the mAb1379 is a conformational epitope that is not a linear epitope.

One of skill in the art can identify and/or assemble conformational epitopes and/or sequential epitopes using known techniques, including mutational analysis (e.g., site-directed mutagenesis); protection from proteolytic degradation (protein footprinting); mimotope analysis using, e.g., synthetic peptides and pepscan, BIACORE or ELISA; antibody competition mapping; combinatorial peptide library screening; matrix-assisted laser desorption/ionization time-of-flight (MALDI-TOF) mass spectrometry; or three-dimensional modeling (e.g., using any suitable software program, including, but not limited to, MOLSCRIPT 2.0 (Avatar Software AB, Heleneborgsgatan 21C, SE-11731 Stockholm, Sweden), the graphical display program O (Jones et. al., *Acta Crystallography*, vol. A47, p. 110, 1991), the graphical display program GRASP, or the graphical display program INSIGHT). For example, one can use molecular replacement or other techniques and the known three-dimensional structure of a related protein to model the three-dimensional structure of factor B and predict the conformational epitope of antibody binding to this structure. Indeed, one can use one or any combination of such techniques to define the antibody binding epitope. FIGS. 4 and 5 illustrate the use of three-dimensional modeling, combined with information from mimotope analysis and mutational analysis, to identify the epitope of a factor B antibody useful in the present invention.

As used herein, the term "selectively binds to" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art, including, but not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry.

One embodiment of the present invention includes the use of an antibody or antigen binding fragment thereof that is a competitive inhibitor of the binding of factor B to the anti-factor B antibody (e.g., monoclonal antibody 1379) to inhibit physiological damage and effects associated with TBI or SCI. According to the present invention, a competitive inhibitor of factor B binding to an anti-factor B antibody of the present invention is an inhibitor (e.g., another antibody or antigen binding fragment or polypeptide) that binds to factor B at the same or similar epitope as the known anti-factor B antibody of the present invention (e.g., mAb 1379) such that binding of the known anti-factor B antibody to factor B is inhibited. A competitive inhibitor may bind to the target (e.g., factor B) with a greater affinity for the target than the anti-factor B antibody. A competitive inhibitor can be used in a manner similar to that described herein for the anti-factor B antibody 1379 (e.g., to inhibit the alternative complement pathway, to inhibit physiological damage or effects caused by TBI or SCI). For example, one embodiment of the invention relates to the use of an isolated antibody or antigen binding fragment thereof that specifically binds to factor B, wherein the antibody or fragment thereof competitively inhibits mAb1379 for specific binding to factor B, and wherein, when the antibody or fragment thereof binds to factor B, the alternative complement pathway is inhibited or alternatively, the ability of mAb1379 to inhibit the alternative complement pathway is inhibited. Another embodiment relates to the use of an isolated antibody or fragment thereof that specifically binds to factor B, wherein the isolated antibody or fragment thereof competitively inhibits a second antibody or fragment thereof for specific binding to factor B, and wherein the second antibody or fragment thereof binds to the third SCR domain of factor B.

Competition assays can be performed using standard techniques in the art (e.g., competitive ELISA or other binding assays). For example, competitive inhibitors can be detected and quantitated by their ability to inhibit the binding of factor B to a known, labeled anti-factor B antibody (e.g., the mAb 1379). Antibody-antibody competition assays in the presence of human factor B are described in U.S. Patent Application Publication No. 2005-0260198-A1 and in PCT Publication No. WO 2005/077417, supra. Competitive inhibitors of the binding of factor B to anti-factor B 1379 are also described in U.S. Patent Application Publication No. 2005-0260198-A1 and in PCT Publication No. WO 2005/077417, supra.

According to the present invention, antibodies are characterized in that they comprise immunoglobulin domains and as such, they are members of the immunoglobulin superfamily of proteins. Generally speaking, an antibody molecule comprises two types of chains. One type of chain is referred to as the heavy or H chain and the other is referred to as the light or L chain. The two chains are present in an equimolar ratio, with each antibody molecule typically having two H chains and two L chains. The two H chains are linked together by disulfide bonds and each H chain is linked to a L chain by a disulfide bond. There are only two types of L chains referred to as lambda ($\lambda$) and kappa ($\kappa$) chains. In contrast, there are five major H chain classes referred to as isotypes. The five classes include immunoglobulin M (IgM or $\mu$), immunoglobulin D (IgD or $\delta$), immunoglobulin G (IgG or $\lambda$), immunoglobulin A (IgA or $\alpha$), and immunoglobulin E (IgE or $\epsilon$). The distinctive characteristics between such isotypes are defined by the constant domain of the immunoglobulin and are discussed in detail below. Human immunoglobulin molecules comprise nine isotypes, IgM, IgD, IgE, four subclasses of IgG including IgG1 ($\gamma$1), IgG2 ($\gamma$2), IgG3 ($\gamma$3) and IgG4 ($\gamma$4), and two subclasses of IgA including IgA1 ($\alpha$1) and IgA2 ($\alpha$2). In humans, IgG subclass 3 and IgM are the most potent complement activators (classical complement system), while IgG subclass 1 and to an even lesser extent, 2, are moderate to low activators of the classical complement system. IgG4 subclass does not activate the complement system (classical or alternative). The only human immunoglobulin isotype known to activate the alternative complement system is IgA. In mice, the IgG subclasses are IgG1, IgG2a, IgG2b and IgG3. Murine IgG1 does not activate complement, while IgG2a, IgG2b and IgG3 are complement activators.

Each H or L chain of an immunoglobulin molecule comprises two regions referred to as L chain variable domains ($V_L$ domains) and L chain constant domains ($C_L$ domains), and H chain variable domains ($V_H$ domains) and H chain constant domains ($C_H$ domains). A complete $C_H$ domain comprises three sub-domains (CH1, CH2, CH3) and a hinge region. Together, one H chain and one L chain can form an arm of an immunoglobulin molecule having an immunoglobulin variable region. A complete immunoglobulin molecule comprises two associated (e.g., di-sulfide linked) arms. Thus, each arm of a whole immunoglobulin comprises a $V_{H+L}$ region, and a $C_{H+L}$ region. As used herein, the term "variable region" or "V region" refers to a $V_{H+L}$ region (also known as an Fv fragment), a $V_L$ region or a $V_H$ region. Also as used herein, the term "constant region" or "C region" refers to a $C_{H+L}$ region, a $C_L$ region or a $C_H$ region.

Limited digestion of an immunoglobulin with a protease may produce two fragments. An antigen binding fragment is referred to as an Fab, an Fab', or an F(ab')$_2$ fragment. A fragment lacking the ability to bind to antigen is referred to as an Fc fragment. An Fab fragment comprises one arm of an immunoglobulin molecule containing a L chain ($V_L+C_L$ domains) paired with the $V_H$ region and a portion of the $C_H$ region (CH1 domain). An Fab' fragment corresponds to an Fab fragment with part of the hinge region attached to the CH1 domain. An F(ab')$_2$ fragment corresponds to two Fab' fragments that are normally covalently linked to each other through a di-sulfide bond, typically in the hinge regions.

The $C_H$ domain defines the isotype of an immunoglobulin and confers different functional characteristics depending upon the isotype. For example, $\mu$ constant regions enable the formation of pentameric aggregates of IgM molecules and $\alpha$ constant regions enable the formation of dimers.

The antigen specificity of an immunoglobulin molecule is conferred by the amino acid sequence of a variable, or V, region. As such, V regions of different immunoglobulin molecules can vary significantly depending upon their antigen specificity. Certain portions of a V region are more conserved than others and are referred to as framework regions (FW regions). In contrast, certain portions of a V region are highly variable and are designated hypervariable regions. When the $V_L$ and $V_H$ domains pair in an immunoglobulin molecule, the hypervariable regions from each domain associate and create hypervariable loops that form the antigen binding sites. Thus, the hypervariable loops determine the specificity of an immunoglobulin and are termed complementarity-determining regions (CDRs) because their surfaces are complementary to antigens.

Further variability of V regions is conferred by combinatorial variability of gene segments that encode an immunoglobulin V region. Immunoglobulin genes comprise multiple germline gene segments which somatically rearrange to form a rearranged immunoglobulin gene that encodes an immunoglobulin molecule. $V_L$ regions are encoded by a L chain V gene segment and J gene segment (joining segment). $V_H$ regions are encoded by a H chain V gene segment, D gene segment (diversity segment) and J gene segment (joining segment).

Both a L chain and H chain V gene segment contain three regions of substantial amino acid sequence variability. Such regions are referred to as L chain CDR1, CDR2 and CDR3, and H chain CDR1, CDR2 and CDR3, respectively. The length of an L chain CDR1 can vary substantially between different $V_L$ regions. For example, the length of CDR1 can vary from about 7 amino acids to about 17 amino acids. In contrast, the lengths of L chain CDR2 and CDR3 typically do not vary between different $V_L$ regions. The length of a H chain CDR3 can vary substantially between different $V_H$ regions. For example, the length of CDR3 can vary from about 1 amino acid to about 20 amino acids. Each H and L chain CDR region is flanked by FW regions.

Other functional aspects of an immunoglobulin molecule include the valency of an immunoglobulin molecule, the affinity of an immunoglobulin molecule, and the avidity of an immunoglobulin molecule. As used herein, affinity refers to the strength with which an immunoglobulin molecule binds to an antigen at a single site on an immunoglobulin molecule (i.e., a monovalent Fab fragment binding to a monovalent antigen). Affinity differs from avidity, which refers to the sum total of the strength with which an immunoglobulin binds to an antigen. Immunoglobulin binding affinity can be measured using techniques standard in the art, such as competitive binding techniques, equilibrium dialysis or BIAcore methods. As used herein, valency refers to the number of different antigen binding sites per immunoglobulin molecule (i.e., the number of antigen binding sites per antibody molecule of antigen binding fragment). For example, a monovalent immunoglobulin molecule can only bind to one antigen at one time, whereas a bivalent immunoglobulin molecule can bind to two or more antigens at one time, and so forth. Both monovalent and bivalent antibodies that selectively bind to proteins of the alternative complement pathway are encompassed herein.

In one embodiment, the antibody is a bi- or multi-specific antibody. A bi-specific (or multi-specific) antibody is capable of binding two (or more) antigens, as with a divalent (or multivalent) antibody, but in this case, the antigens are different antigens (i.e., the antibody exhibits dual or greater specificity). For example, an antibody that selectively binds to a protein in the alternative complement pathway according to the present invention (e.g., an anti-factor B antibody as described herein) can be constructed as a bi-specific antibody, wherein the second antigen binding specificity is for a desired target. Therefore, one bi-specific antibody encompassed by the present invention includes an antibody having: (a) a first portion (e.g., a first antigen binding portion) which binds to a protein in the alternative complement pathway (e.g., factor B); and (b) a second portion which binds to a cell surface molecule expressed by a cell. In this embodiment, the second portion can bind to any cell surface molecule. One preferred cell surface molecule is a receptor or ligand, so that the antibody is targeted to a particular cell or tissue type and/or to a particular site in an animal to which the antibody is delivered. In one embodiment, the second antigen binding specificity is for a complement receptor. A particularly preferred complement receptor includes, but is not limited to, complement receptor type 2 (CR2). Antibodies that selectively bind to CR2 and could therefore be used in this embodiment of the invention are described, for example, in U.S. Pat. No. 6,820,011.

In one embodiment, antibodies of the present invention include humanized antibodies. Humanized antibodies are molecules having an antigen binding site derived from an immunoglobulin from a non-human species, the remaining immunoglobulin-derived parts of the molecule being derived from a human immunoglobulin. The antigen binding site may comprise either complete variable regions fused onto human constant domains or only the complementarity determining regions (CDRs) grafted onto appropriate human framework regions in the variable domains. Humanized antibodies can be produced, for example, by modeling the antibody variable domains, and producing the antibodies using genetic engineering techniques, such as CDR grafting (described below). A description various techniques for the production of humanized antibodies is found, for example, in Morrison et al. (1984) *Proc. Natl. Acad. Sci. USA* 81:6851-55; Whittle et al. (1987) *Prot. Eng.* 1:499-505; Co et al. (1990) *J. Immunol.* 148:1149-1154; Co et al. (1992) *Proc. Natl. Acad. Sci. USA* 88:2869-2873; Carter et al. (1992) *Proc. Natl. Acad. Sci.* 89:4285-4289; Routledge et al. (1991) *Eur. J. Immunol.* 21:2717-2725 and PCT Patent Publication Nos. WO 91/09967; WO 91/09968 and WO 92/113831.

Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies, humanized antibodies (discussed above), antibodies that can bind to more than one epitope (e.g., bi-specific antibodies), or antibodies that can bind to one or more different antigens (e.g., bi- or multi-specific antibodies), may also be employed in the invention.

Genetically engineered antibodies of the invention include those produced by standard recombinant DNA techniques involving the manipulation and re-expression of DNA encoding antibody variable and/or constant regions. Particular examples include, chimeric antibodies, where the $V_H$ and/or $V_L$ domains of the antibody come from a different source as compared to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications: EP-A 0194276, EP-A 0239400, EP-A 0451216 and EP-A 0460617.

In one embodiment, chimeric antibodies are produced according to the present invention comprising antibody variable domains that bind to a protein in the alternative complement pathway (e.g., factor B) and fused to these domains, a protein that serves as a second targeting moiety. For example, the targeting moiety can include a protein that is associated with the cell or tissue to be targeted or with a particular system in the animal. For example, the targeting moiety can be a selectin or a portion of a complement receptor. One preferred complement receptor to use in this aspect of the invention includes complement receptor type 2 (CR2). The use of CR2 and portions thereof in a fusion or chimeric protein (e.g., as a delivery system) is described in detail in U.S. Pat. No. 6,820,011.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (*Nature* 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

A preferred method to produce antibodies of the present invention includes (a) administering to an animal an effective amount of a protein or peptide (e.g., a factor B protein or peptide including domains thereof) to produce the antibodies and (b) recovering the antibodies. In another method, antibodies of the present invention are produced recombinantly. For example, once a cell line, for example a hybridoma, expressing an antibody according to the invention has been obtained, it is possible to clone therefrom the cDNA and to identify the variable region genes encoding the desired antibody, including the sequences encoding the CDRs. From here, antibodies and antigen binding fragments according to the invention may be obtained by preparing one or more replicable expression vectors containing at least the DNA sequence encoding the variable domain of the antibody heavy or light chain and optionally other DNA sequences encoding remaining portions of the heavy and/or light chains as desired, and transforming/transfecting an appropriate host cell, in which production of the antibody will occur. Suitable expression hosts include bacteria, (for example, an *E. coli* strain), fungi, (in particular yeasts, e.g. members of the genera *Pichia, Saccharomyces*, or *Kluyveromyces*,) and mammalian cell lines, e.g. a non-producing myeloma cell line, such as a mouse NSO line, or CHO cells. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al. (Molecular Cloning, Cold Spring Harbor Laboratory, New York, 1989); DNA sequencing can be performed as described in Sanger et al. (PNAS 74, 5463, (1977)) and the Amersham International plc sequencing handbook; and site directed mutagenesis can be carried out according to the method of Kramer et al. (*Nucl. Acids Res.* 12, 9441, (1984)) and the Anglian Biotechnology Ltd. handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews (ed. Tombs, M P, 10, Chapter 1, 1992, Intercept, Andover, UK) and in the aforementioned European Patent Applications.

Alternative methods, employing, for example, phage display technology (see for example U.S. Pat. No. 5,969,108, U.S. Pat. No. 5,565,332, U.S. Pat. No. 5,871,907, U.S. Pat. No. 5,858,657) or the selected lymphocyte antibody method of U.S. Pat. No. 5,627,052 may also be used for the production of antibodies and/or antigen fragments of the invention, as will be readily apparent to the skilled individual.

The invention also extends to the use of non-antibody polypeptides, sometimes referred to as antigen binding partners or antigen binding polypeptides, that have been designed to bind selectively to and cause the neutralization or inhibition of a protein according to the present invention. Examples of the design of such polypeptides, which possess a prescribed ligand specificity are given in Beste et al. (*Proc. Natl. Acad. Sci.* 96:1898-1903, 1999), incorporated herein by reference in its entirety.

The present invention also includes a formulation or composition for reducing physiological damage associated with TBI or SCI. The formulation comprises: (a) any one or more inhibitors of the alternative complement pathway as described herein (e.g., an anti-factor B antibody described herein); and (b) at least one pharmaceutically acceptable carrier.

In one embodiment, the formulation or composition can include one or more additional agents, such as another agent that is suitable for treating at least one symptom of, or physiological damage associated with, TBI (e.g., osmotic drugs, sedatives, analgesics, muscle relaxants, barbiturates, etc.). In addition, the formulation can be administered to a patient in conjunction with another therapy or protocol that is used to treat or ameliorate damage associated with TBI. Such therapies or protocols include, but are not limited to: reduction of mass lesions by surgical evacuation of intracranial hematomas; the reduction of brain swelling with osmotic drugs (e.g., mannitol); the therapeutic drainage of cerebrospinal fluid (CSF) through intraventricular catheters; achievement and maintenance of adequate gas exchange and circulatory stability; prevention of hypoxemia and hypercarbia; repeated CT scans for detection of delayed secondary intracranial pathology; profound sedation and analgesia to avoid stress and pain; achievement and maintenance of optimal CPP (>70 mmHg) and cerebral oxygen balance; avoidance of hyperthermia (<38° C.); prevention of hyperglycemia and hyponatremia; prevention of routinely performed head elevation; prevention of stress ulcers and maintenance of gut mucosal integrity; prophylaxis for complicating factors (e.g. pneumonia or meningitis); intracranial pressure (ICP)-targeted therapy (e.g., deepening of sedation, analgesia, muscle relaxation; CSF drainage through ventricular catheters; moderate hyperventilation under certain circumstances; osmotherapy; moderate hypothermia (±34° C.); and/or barbiturate coma); and/or gas-enabled (CO) attenuation of neuroinflammation. Various treatments for TBI are well known in the art and are described, for example, in Royo et al., 2003, *Current Opin. Pharmacol.* 3:27-32; Dutton and McCunn, 2003, *Current Opin. Crit. Care* 9:503-509; Elf et al., 2003, *Eur. J. Trauma* 29:74-80; Ghajar et al., 2000, *Lancet* 356:923-929.

In another embodiment, the formulation or composition can include one or more additional agents, such as another agent that is suitable for treating at least one symptom of, or physiological damage associated with, SCI (e.g., steroids, such as methylprednisolone). In addition, the formulation can be administered to a patient in conjunction with another therapy or protocol that is used to treat or ameliorate damage associated with SCI. Such therapies or protocols include, but are not limited to: immobilization of the spine; decompression surgery; surgery to stabilize the vertebrae; surgery to realign the vertebrae; traction. Various treatments for SCI are well known in the art and are described, for example, in Ramer et al., 2005, *Spinal Cord* 43 (3):134-61.

According to the present invention, a "pharmaceutically acceptable carrier" includes pharmaceutically acceptable excipients and/or pharmaceutically acceptable delivery vehicles, which are suitable for use in the administration of a formulation or composition to a suitable in vivo site. A suitable in vivo site is preferably any site wherein the alternative complement pathway can be inhibited, but in one preferred embodiment, is in the brain tissue of a patient that has or is at risk of developing, physiological damage associated with TBI or SCI. Preferred pharmaceutically acceptable carriers are capable of maintaining an agent used in a formulation of the invention in a form that, upon arrival of the agent at the target site in a patient, the agent is capable of acting on its target (e.g., a protein that is a component of the alternative complement pathway), preferably resulting in a therapeutic benefit to the patient.

Suitable excipients of the present invention include excipients or formularies that transport or help transport, but do not specifically target a composition to a cell or tissue (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Formulations of the present invention can be sterilized by conventional methods and/or lyophilized.

One type of pharmaceutically acceptable carrier includes a controlled release formulation that is capable of slowly releasing a composition of the present invention into an animal. As used herein, a controlled release formulation comprises an agent of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposphers, and transdermal delivery systems. Other suitable carriers include any carrier that can be bound to or incorporated with the agent that extends that half-life of the agent to be delivered. Such a carrier can include any suitable protein carrier or even a fusion segment that extends the half-life of a protein when delivered in vivo. Suitable delivery vehicles have been previously described herein, and include, but are not limited to liposomes, viral vectors or other delivery vehicles, including ribozymes. Natural lipid-containing delivery vehicles include cells and cellular membranes. Artificial lipid-containing delivery vehicles include liposomes and micelles. A delivery vehicle of the present invention can be modified to target to a particular site in a patient, thereby targeting and making use of an inhibitory agent at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

A pharmaceutically acceptable carrier which is capable of targeting is referred to as a "targeting delivery vehicle." Targeting delivery vehicles of the present invention are capable of delivering a formulation, including an inhibitory agent, to a target site in a patient. A "target site" refers to a site in a patient to which one desires to deliver a therapeutic formulation. For example, a target site can be any cell or tissue that is targeted by direct injection or delivery using liposomes, viral vectors or other delivery vehicles, including ribozymes. A delivery vehicle of the present invention can be modified to target to a particular site in an animal, thereby targeting and making use of a nucleic acid molecule at that site. Suitable modifications include manipulating the chemical formula of the lipid portion of the delivery vehicle and/or introducing into the vehicle a compound capable of specifically targeting a delivery vehicle to a preferred site, for example, a preferred cell or tissue type (e.g., to the brain or to the central nervous system). Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Particularly useful examples include any ligands that are associated with the complement pathway (e.g., CR2, C3, C3d, C3dg, iC3b, C3b) or any ligands (e.g., selectins) that are associated with the cell type, tissue type, or site in the animal to be treated.

Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics. In one embodiment, a targeting delivery vehicle can be a formulation that allows a compound to cross the blood-brain barrier.

One delivery vehicle useful for a variety of administration routes and agents is a liposome. A liposome is capable of remaining stable in an animal for a sufficient amount of time to deliver a nucleic acid molecule described in the present invention to a preferred site in the animal. A liposome, according to the present invention, comprises a lipid composition that is capable of delivering a nucleic acid molecule or other compound to a particular, or selected, site in an animal. A liposome according to the present invention comprises a lipid composition that is capable of fusing with the plasma membrane of the targeted cell to deliver a nucleic acid molecule into a cell. Suitable liposomes for use with the present invention include any liposome. Preferred liposomes of the present invention include those liposomes typically used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule or inhibitory agent of the present invention can be achieved using methods standard in the art.

Another delivery vehicle comprises a viral vector. A viral vector includes an isolated nucleic acid molecule useful in the method of the present invention, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

Agents and formulations of the present invention can be administered to any animal or patient, and preferably to humans. According to the present invention, administration of an agent or formulation is useful to inhibit any symptom of physiological damage associated with TBI, SCI, or similar or related conditions. Patients whom are suitable candidates for the method of the present invention include, but are not limited to, patients that have, or are at risk of developing (e.g., are likely or predicted to develop), physiological damage to the brain or spinal cord and conditions related to this damage, as a result of injury (including traumatic injury) or disease.

In accordance with the present invention, determination of acceptable protocols to administer an agent or a composition including the agent, including the route of administration and the effective amount of an agent to be administered to an animal, can be accomplished by those skilled in the art. An agent or composition of the present invention can be administered in vivo or ex vivo. Suitable in vivo routes of administration can include, but are not limited to, oral, nasal, inhaled, topical, intratracheal, transdermal, rectal, brain (e.g., intracranial), spinal (e.g., intraspinal or to the epidural space of the spinal cord), and parenteral routes. Preferred parenteral routes can include, but are not limited to, subcutaneous, intradermal, intravenous, intramuscular, and intraperitoneal routes. Preferred topical routes include inhalation by aerosol (i.e., spraying) or topical surface administration to the skin of an animal. Preferably, an agent is administered by systemic routes (e.g., intraperitoneal, intravenous), with intravenous administration being particularly preferred, or by administration to the brain, spinal cord, or the epidural space of the spinal cord. For traumatic brain injury, administration by intravenous administration or to the brain is preferred. For spinal cord injury, administration by intravenous administration, spinal cord administration, or administration to the epidural space of the spinal cord is preferred. Ex vivo refers to performing part of the administration step outside of the patient.

Techniques for administration of agents and compositions to the brain and central nervous system include, but art not limited to, intravenous administration, intraperitoneal administration, intraarterial delivery with blood-brain barrier disruption, continuous infusion of drugs through the brain using convection-enhanced delivery methods, implantation, intrathecal infusion, intraventricular administration, interstitial administration, and intraspinal administration. Intravenous, intraperitoneal, intramuscular, and intraspinal administrations can be performed using methods standard in the art. Aerosol (inhalation) delivery can be performed using methods standard in the art (see, for example, Stribling et al., Proc. Natl. Acad. Sci. USA 189:11277-11281, 1992, which is incorporated herein by reference in its entirety). Carriers suitable for aerosol delivery are described above. Devices for delivery of aerosolized formulations include, but are not limited to, pressurized metered dose inhalers (MDI), dry powder inhalers (DPI), and metered solution devices (MSI), and include devices that are nebulizers and inhalers. Oral delivery can be performed by complexing a therapeutic composition of the present invention to a carrier capable of withstanding degradation by digestive enzymes in the gut of an animal. Examples of such carriers, include plastic capsules or tablets, such as those known in the art. Direct injection techniques are particularly useful for administering a recombinant nucleic acid molecule to a cell or tissue that is accessible by surgery, and particularly, on or near the surface of the body. Administration of a composition locally within the area of a target cell refers to injecting the composition centimeters and preferably, millimeters from the target cell or tissue.

Various methods of administration and delivery vehicles disclosed herein have been shown to be effective for delivery of a nucleic acid molecule to a target cell or tissue, whereby the nucleic acid molecule transfected the cell and was expressed. In many studies, successful delivery and expression of a heterologous gene was achieved in preferred cell types and/or using preferred delivery vehicles and routes of administration of the present invention. Delivery of numerous nucleic acid sequences to a variety of target tissues has been accomplished by administration of viral vectors encoding the nucleic acid sequences. (e.g., see, of many examples, retroviral vector; Blaese et al., 1995, Science 270:475-480; Bordignon et al., 1995, Science 270:470-475), nasal administration (CFTR-adenovirus-associated vector), intracoronary administration (adenoviral vector and Hemagglutinating virus of Japan, see above), intravenous administration (adeno-associated viral vector; Koeberl et al., 1997, Proc Natl Acad Sci USA 94:1426-1431). Millecamps et al. reported the targeting of adenoviral vectors to neurons using neuron restrictive enhancer elements placed upstream of the promoter for the transgene (phosphoglycerate promoter). Such vectors were administered to mice and rats intramuscularly and intracerebrally, respectively, resulting in successful neuronal-specific transfection and expression of the transgene in vivo (Millecamps et al., 1999, Nat. Biotechnol. 17:865-869). Bennett et al. reported the use of adeno-associated viral vector to deliver and express a gene by subretinal injection in the neural retina in vivo for greater than 1 year (Bennett, 1999, ibid.).

A suitable single dose of an inhibitory agent to administer to an animal is a dose that is capable of reducing or preventing at least one symptom of physiological damage due to TBI or SCI in an animal when administered one or more times over a suitable time period. A preferred single dose of an agent, including proteins, small molecules and antibodies, for use in the method described herein, comprises between about 0.01 microgram×kilograms$^{-1}$ and about 10 milligram×kilograms$^{-1}$ body weight of an animal. A more preferred single dose of an agent comprises between about 1 microgram×kilogram$^{-1}$ and about 10 milligram×kilogram$^{-1}$ body weight of an animal. An even more preferred single dose of an agent comprises between about 5 microgram×kilograms$^{-1}$ and about 7 milligram×kilogram$^{-1}$ body weight of an animal. An even more preferred single dose of an agent comprises between about 10 microgram×kilograms$^{-1}$ and about 5 milligram×kilograms$^{-1}$ body weight of an animal. A particularly preferred single dose of an agent comprises between about 0.1 milligram×kilograms$^{-1}$ and about 5 milligram×kilograms$^{-1}$ body weight of an animal, if the an agent is delivered by aerosol. Another particularly preferred single dose of an agent comprises between about 0.1 microgram×kilograms$^{-1}$ and about 10 microgram×kilogram$^{-1}$ body weight of an animal, if the agent is delivered parenterally.

In one embodiment, an appropriate single dose of a nucleic acid:liposome complex of the present invention is from about 0.1 µg to about 100 µg per kg body weight of the patient to which the complex is being administered. In another embodiment, an appropriate single dose is from about 1 µg to about 10 µg per kg body weight. In another embodiment, an appropriate single dose of nucleic acid:lipid complex is at least about 0.1 µg of nucleic acid, more preferably at least about 1 µg of nucleic acid, even more preferably at least about 10 µg of nucleic acid, even more preferably at least about 50 µg of nucleic acid, and even more preferably at least about 100 µg of nucleic acid.

A preferred single dose of an antibody comprises between about 1 ng×kilograms$^{-1}$ and about less than 1 mg×kilogram$^{-1}$ body weight of an animal. A more preferred single dose of an antibody comprises between about 20 ng×kilograms$^{-1}$ and about 600 µg×kilograms$^{-1}$ body weight of the animal. An even more preferred single dose of an antibody, particularly when the antibody formulation is delivered by nebulization, comprises between about 20 ng×kilograms$^{-1}$ and about 600 µg×kilograms$^{-1}$ body weight of the animal, and more preferably, between about 20 ng×kilograms$^{-1}$ and about 500 µg×kilogram$^{-1}$, and more preferably, between about 20 ng×kilograms$^{-1}$ and about 400 µg×kilogram$^{-1}$, and more preferably, between about 20 ng×kilograms$^{-1}$ and about 300 µg×kilogram$^{-1}$, and more preferably, between about 20 ng×kilogram$^{-1}$ and about 200 µg×kilogram$^{-1}$, and more preferably, between about 20 ng×kilograms$^{-1}$ and about 100 µg×kilogram$^{-1}$, and more preferably, between about 20 ng×kilograms$^{-1}$ and about 50 µg×kilogram$^{-1}$ body weight of the animal.

Another preferred single dose of an antibody, particularly when the antibody formulation is delivered by nebulization, comprises between about 200 ng×kilogram$^{-1}$ and about 600 µg×kilogram$^{-1}$ body weight of the animal, and more preferably, between about 200 ng×kilogram$^{-1}$ and about 500 µg×kilogram$^{-1}$, and more preferably, between about 200 ng×kilogram$^{-1}$ and about 400 µg×kilogram$^{-1}$, and more preferably, between about 200 ng×kilograms$^{-1}$ and about 300 µg×kilogram$^{-1}$, and more preferably, between about 200 ng×kilograms$^{-1}$ and about 200 µg×kilogram$^{-1}$, and more preferably, between about 200 ng×kilograms$^{-1}$ and about 100 µg×kilogram$^{-1}$, and more preferably, between about 200 ng×kilogram$^{-1}$ and about 50 µg×kilogram$^{-1}$ body weight of the animal.

Another preferred single dose of an antibody, particularly when the antibody formulation is delivered by direct inhalation from an inhaler, comprises between about 2 ng×kilogram$^{-1}$ and about 100 µg×kilogram$^{-1}$ body weight of the animal, and more preferably, between about 2 ng×kilogram$^{-1}$ and about 50 µg×kilogram$^{-1}$, and more preferably, between about 2 ng×kilogram$^{-1}$ and about 10 µg×kilogram$^{-1}$, and more preferably, between about 2 ng×kilogram$^{-1}$ and about 5 µg×kilogram$^{-1}$, and more preferably, between about 2 ng×kilograms$^{-1}$ and about 1 µg×kilogram$^{-1}$, and more preferably, between about 2 ng×kilogram$^{-1}$ and about 0.5 µg×kilogram$^{-1}$, and more preferably, between about 2 ng×kilogram$^{-1}$ and about 0.25 µg×kilogram$^{-1}$, and more preferably, between about 2 ng×kilogram$^{-1}$ and about 0.1 µg×kilogram$^{-1}$ body weight of the animal.

In another embodiment, the antibody is administered at a dose of less than about 500 µg antibody per milliliter of formulation, and preferably, less than about 250 µg antibody per milliliter of formulation, and more preferably, less than about 100 µg antibody per milliliter of formulation, and more preferably, less than about 50 µg antibody per milliliter of formulation, and more preferably, less than about 40 µg antibody per milliliter of formulation, and more preferably, less than about 30 µg antibody per milliliter of formulation, and more preferably, less than about 20 µg antibody per milliliter of formulation, and more preferably, less than about 10 µg antibody per milliliter of formulation, and even more preferably, between about 5 µg antibody and about 10 µg antibody per milliliter of formulation.

According to the method of the present invention, an effective amount of an agent that inhibits physiological damage due to TBI or SCI to administer to an animal comprises an amount that is capable of reducing at least one symptom or indicator of physiological damage due to TBI or SCI, or is capable of enhancing recovery from TBI or SCI, without being toxic to the animal. An amount that is toxic to an animal comprises any amount that causes damage to the structure or function of an animal (i.e., poisonous).

In one embodiment of the present invention, in an animal that has experienced TBI or SCI, an effective amount of an agent to administer to an animal is an amount that measurably reduces at least one symptom or indicator of physiological damage due to TBI or SCI in the animal as compared to prior to administration of the agent or as compared to in the absence of administration of the agent. In another embodiment, an effective amount of an agent to administer to an animal is an amount that measurably reduces at least one symptom or indicator of damage due to TBI or SCI in the animal as compared to a level of the symptom in a population of animals that have experienced substantially similar TBI or SCI wherein the agent was not administered. The agent is preferably capable of reducing at least one symptom or indicator of physiological damage due to TBI (e.g. brain damage) or SCI (e.g., spinal cord damage) in an animal, even when the agent is administered after the onset of the physical symptoms of the damage. Most preferably, an effective amount of the agent is an amount that reduces the symptom(s) or indicator(s) of damage due to TBI or SCI to the point where the symptom(s) or indicator(s) is no longer detected in the patient. In one embodiment, an effective amount of the agent is an amount that enhances the recovery of the patient from TBI or SCI, as measured by cessation or reversal of a symptom or indicator of physiological damage, or as measured by an improvement in a measurable or detectable biological score, value, or measure of neural and related functions in the patient.

In a preferred embodiment, a suitable dose of an agent of the present invention is a dose effective to inhibit the expression or biological activity of at least one protein in the alternative complement pathway as described herein (e.g., factor B, factor D or properdin), as compared to in the absence of the administration of the agent. Methods of measuring the expression or biological activity of a protein have been described above. In another embodiment, a suitable dose of an agent of the present invention is a dose that measurably inhibits the alternative complement pathway of the invention. Activation of complement and inhibition thereof can be measured using techniques/assays that are well-known in the art. For example, one can perform an in vitro analysis of C3 deposition on zymosan A particles as described in the examples. One can also test the ability of the agent to inhibit lysis of unsensitized erythrocytes by human serum. Extrapolation of in vitro results to in vivo dosages based on these assays is within the ability of those of skill in the art.

One of skill in the art will be able to determine that the number of doses of an agent to be administered to an animal is dependent upon the extent of the TBI or SCI and anticipated or observed physiological damage associated with the injury, as well as the response of an individual patient to the treatment. Methods to diagnose both TBI and SCI, including the severity of the conditions, are described above and are known in the art. In addition, the clinician will be able to determine the appropriate timing for delivery of the agent in a manner effective to reduce the symptom(s) associated with or resulting from TBI or SCI in the animal. Preferably, the agent is delivered within 48 hours, and more preferably 36 hours, and more preferably 24 hours, and more preferably within 12 hours, and more preferably within 6 hours, 5 hours, 4 hours, 3 hours, 2 hours, or 1 hour, or even minutes after the event that caused the TBI or SCI. In one embodiment, the agent is administered as soon as it is recognized (i.e., immediately) by the patient, clinician, or other person that the patient has suffered TBI or SCI. In another embodiment, the agent is administered upon the first sign of development of a symptom of brain or neural damage that may be associated with TBI or SCI, and preferably, within at least 2 hours of the development of the symptom(s), and more preferably, within at least 1 hour, and more preferably within at least 30 minutes, and more preferably within at least 10 minutes, and more preferably within at least 5 minutes of development of the symptom(s). Symptoms of physiological damage associated with TBI or SCI and methods for measuring or detecting such symptoms have been described in detail above. Preferably, such administrations are given until signs of reduction of physiological damage or reduction of the symptoms of the potential for physiological damage appear, and then as needed until the symptoms are gone or arrested.

The method of the present invention can be used in any animal, and particularly, in any animal of the Vertebrate class, Mammalia (i.e., mammals), including, without limitation, primates, rodents, livestock and domestic pets. Preferred mammals to treat using the method of the present invention are humans.

The following examples are provided for the purposes of illustration and are not intended to limit the scope of the present invention.

EXAMPLES

Example 1

The following example describes the therapeutic effect of administration of the complement inhibitor, Crry-Ig, on physiological functions after traumatic brain injury (TBI).

Crry-Ig is a fusion between complement receptor-related protein-y (Crry) and an immunoglobulin Fc molecule. Crry is a functional homologue of human decay-accelerating factor (CD55) and membrane-cofactor protein (CD46) and inhibits C3 complement convertase. Therefore, Crry is an inhibitor of both the classical and alternative complement pathways.

Figure 6:
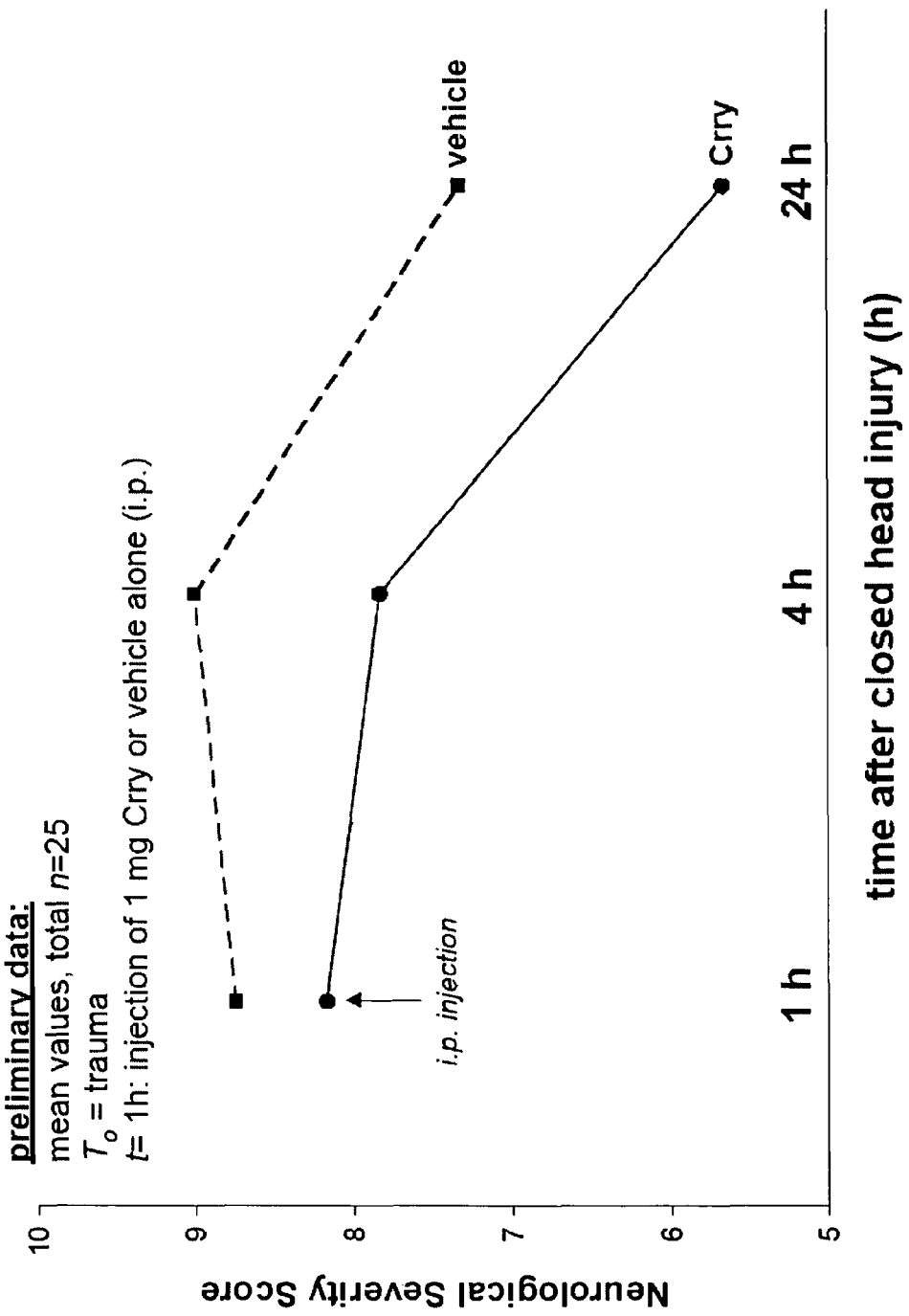
FIG. 6 is a line graph showing that Crry-Ig inhibits neurological impairment after TBI.
Figure 7:
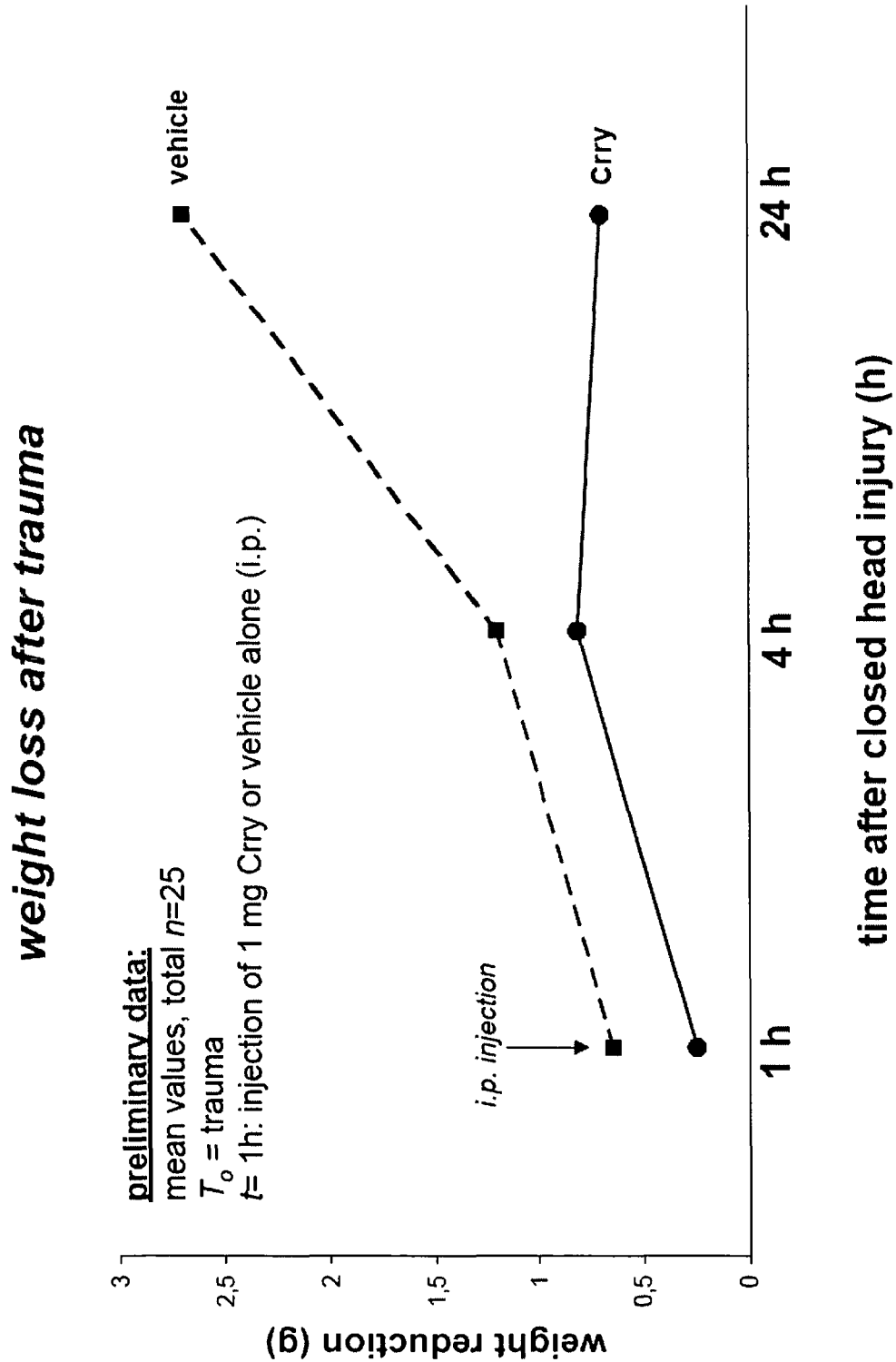
FIG. 7 is a line graph showing that Crry-Ig inhibits weight loss after TBI.

In a standardized model of closed head injury in mice (Chen et al., *J. Neurotrauma* 1996), the post-injury systemic administration of 1 mg Crry-Ig, which corresponds to the therapeutic "time window of opportunity" due to a breached blood-brain-barrier from 1-24 h after trauma in this model system, lead to a significantly improved neurological recovery after TBI within 24 h, as opposed to control mice injected with vehicle only (FIG. 6). In this experiment, the extent of posttraumatic neurological impairment was assessed by a standardized 10-point Neurological Severity Score (NSS) in a blinded fashion by two independent investigators. In addition, head-injured mice injected with 1 mg Crry-Ig i.p. one hour after trauma showed a significantly reduced weight loss compared to vehicle-injected controls (FIG. 7), indicating that the inflammation-induced posttraumatic catabolic state is protected in mice with complement inhibition by Crry-Ig.

These results demonstrate that inhibition of the complement pathway at the level of the C3 complement convertase inhibits physiological damage associated with TBI.

Example 2

The following example demonstrates that Factor B monoclonal antibody reduced brain damage associated with traumatic brain injury (TBI).

Figure 8:
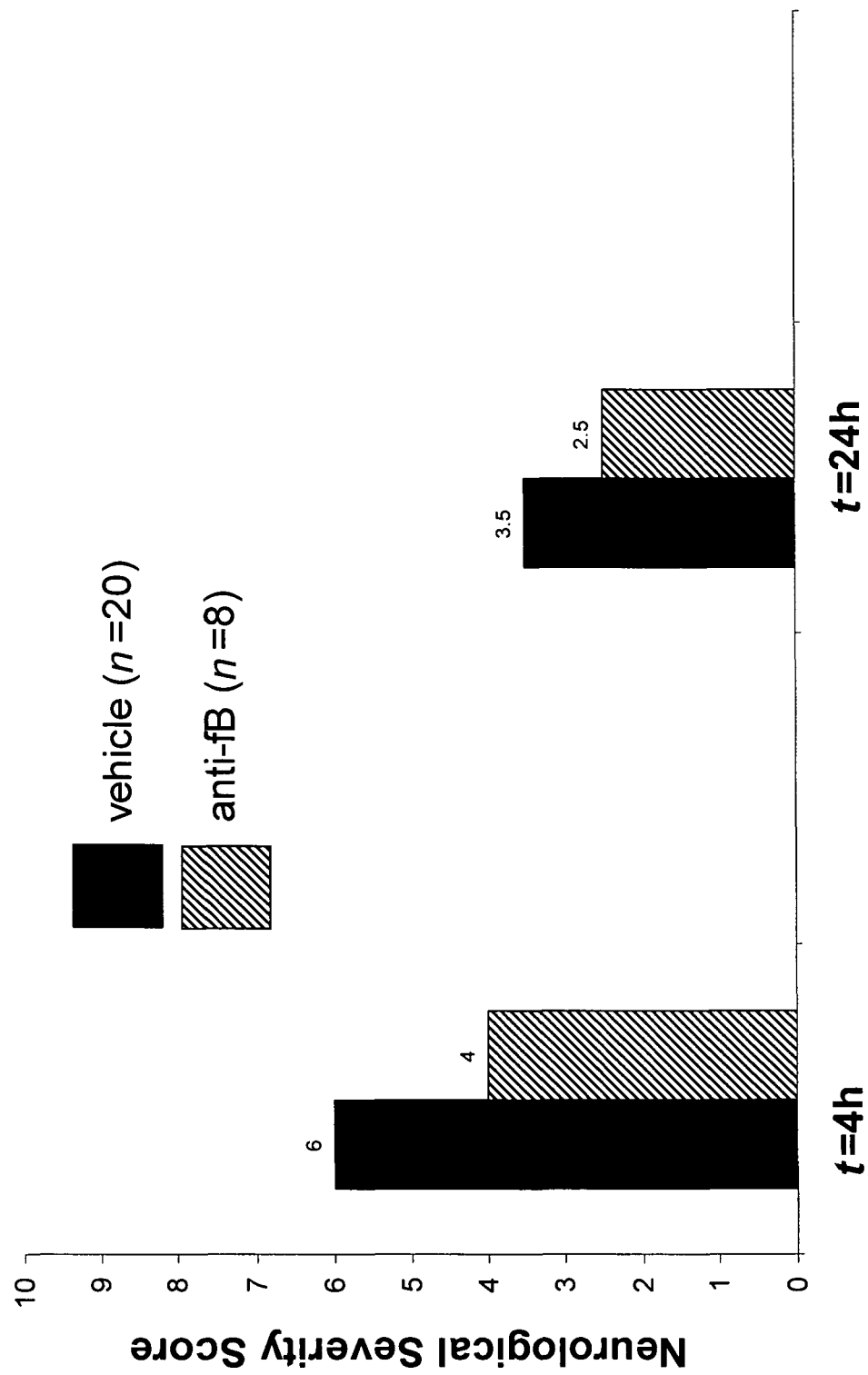
FIG. 8 is a bar graph showing that administration of anti-Factor B (mAb 1379) reduces brain damage associated with TBI.

Preliminary titration studies revealed that in vivo, the intraperitoneal (i.p.) injection of 2 mg mAb1379 (factor B monoclonal antibody, or anti-fB) in C57BL/6 mice weighing 25-35 g resulted in complete inhibition of alternative pathway complement activity, lasting for 48 hours. Anti-fB inhibition studies after experimental closed head injury in C57BL/6 mice (Chen et al., *J. Neurotrauma* 1996) were performed using two experimental groups: one receiving 2 mg mAb1379, injected i.p. at t=1 h, 24 h, or 72 h; and the second receiving vehicle medium alone, injected at identical timepoints. The results revealed a significant neuroprotective effect of alternative pathway complement inhibition in the anti-fB (mAb1379) group, as compared to vehicle-injected control animals, based on a significantly decreased 10-point Neurological Severity Score (NSS) within 24 h after trauma (Table 3; FIG. 8). This result demonstrates that selective inhibition of the alternative complement pathway reduces physiological damage resulting from TBI.

TABLE 3

| Neurological Severity Score (NSS) | | |
|---|---|---|
| | 0 (best)-10 (worst) | |
| | NSS 4 h | NSS 24 h |
| Trauma vehicle (n = 20)* | 6 | 4 |
| Trauma anti-factor B (n = 8)* | 3.5 | 2.5 |

*median values

Example 3

The following example shows that Factor B monoclonal antibody reduced brain damage associated with spinal cord injury (SCI).

Wild-type female C57BL/6 mice (Charles River, Md.) and female fB−/− mice, 6-8-weeks old and 16-20 g in weight (for all mice) were used in this study. Animals were provided water and food ad libitum and were housed in ventilated Plexiglas cages (four mouse/per cage) on a 12/12-h light-dark cycle with a pathogen-free barrier facility and maintained in accordance with the NIH Guide for the Care and Use of Laboratory Animals of the United States Department of Health and Human Services (National Institutes of Health, Bethesda, Md.). Mice were acclimated for at least 1 week prior to experimentation.

Animal surgical and postoperative procedures were approved by the Committee on Animal Research at the Medical University of South Carolina. Surgical procedures were carried out under sterile conditions. Spinal cord contusions were performed using a weight drop device for the induction of spinal cord injury (SCI) in mice (Pannu et al. (2005) *J. Neuroscience Research* 79:340-350). Briefly, mice were anesthetized with an intraperitoneal (i.p.) injection of ketamine (75 mg/kg) and xylazine (16 mg/kg). The dorsal aspect of the back was shaved and scrubbed with iodinated solution. The body temperature was maintained throughout the surgery by a 37° C. warming blanket placed under the animal. A midline incision was made in the skin from the T9 to T13 levels. Laminectomy was performed at the T12 level, leaving the dura intact. The spine was immobilized with a stereotactic device and injury was induced by dropping a weight of 5 g from a height of 3 cm (15 g-cm force) onto the exposed dura. Sham-operated animals underwent laminectomy only. After injury, the muscles were closed in layers and the incision was sutured. The mice were kept on a heating pad. No pre- or postoperative prophylactic antibiotics or analgesics were used in order to avoid their possible interactions with the experimental therapy of SCI. Bladders were manually expressed twice daily until adequate spontaneous voiding returned.

All animals were included in the study of functional recovery. Hindlimb function of experimental mice was assessed weekly by blinded observers using the hindlimb motor function score (Shuhei K J. of Neuropathology and Experimental Neurology (2004) 64-72). The scale ranged from 0 to 5, and scores were as follows: 0: No movement of the hindlimbs; 1: Barely perceptible movement of any hindlimb joints (hip, knee, or ankle); 2: Brisk movements at one or more hindlimb joints (hip, knee, or ankle) in one or both limbs but no co-ordination; 3: Alternate stepping and propulsive movements of hindlimbs but no weight bearing; 4: Weight bearing and can walk with some deficit; 5: Normal walking.

Figure 9:
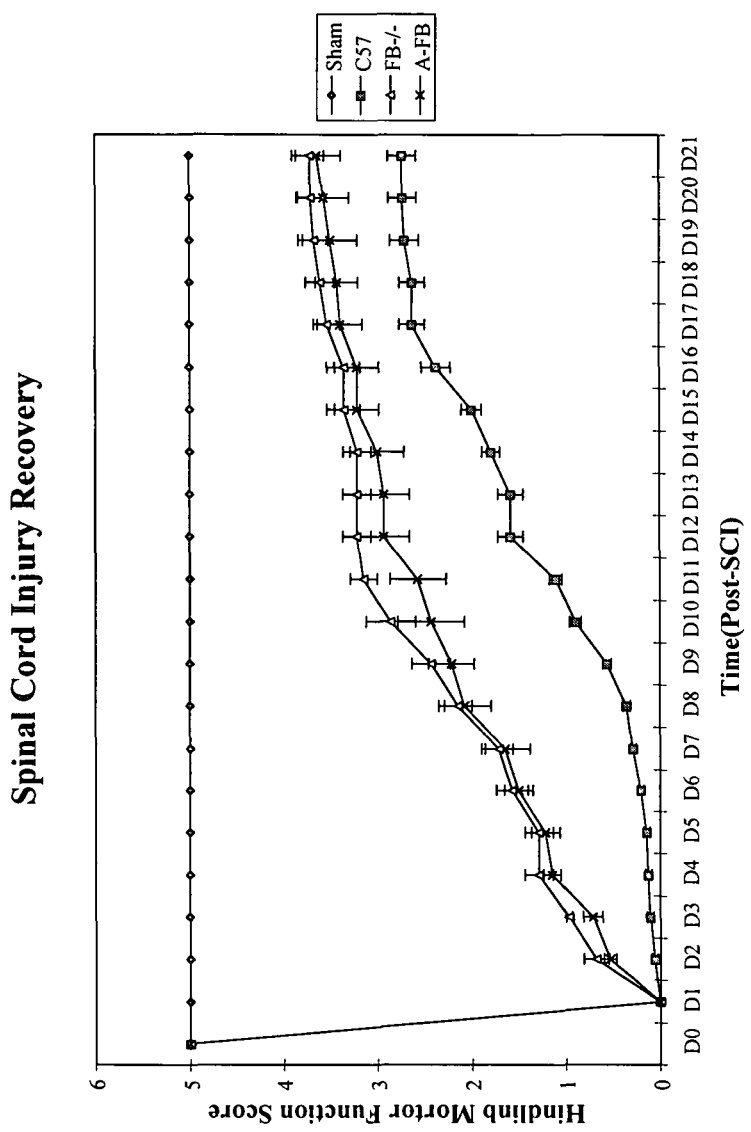
FIG. 9 is a line graph showing that administration of anti-Factor B (mAb 1379) improves recovery from spinal cord injury.

FIG. 9 shows the results of a study investigating the effect of the administration of factor B monoclonal antibody on functional recovery from spinal cord injury. In the murine model for SCI described above, C57BL/6 mice received two intravenous injections of 1 mg/10 g anti-factor B (mAb 1379) at 1 hour and 12 hours post injury (Group Number, n=8). Functional recovery was evaluated as described above once a day for 21 days post injury. Sham-treated mice, untreated mice with experimental SCI, and factor B (−/−) mice with experimental SCI were also evaluated over the time course. As shown in FIG. 9, factor B (−/−) mice and mice that received anti-factor B had a significantly (p<0.01) improved functional recovery score at each of the 21 day time points, as compared to untreated mice with experimental spinal cord injury. These results demonstrate that selective inhibition of the alternative complement pathway is sufficient to provide a significant therapeutic benefit in a model of SCI.

Example 4

The following example demonstrates that the alternative pathway of complement activation plays a crucial role in the pathophysiology of TBI.

Materials and Methods

Factor B−/− Mice.

The genetic knockout mice deficient in factor B (fB−/−) were previously characterized and shown to have a complete lack of a functional alternative complement pathway [58]. They were originally created with Sv129 embryonic stem cells and crossed with C57BL/6 mice prior to expansion of the colony at F1. They were then back-crossed for more than 10 generations against a pure C57BL/6 background and found to be grossly indistinguishable from C57BL/6 mice [34]. Knockout mice and wild-type littermates (fB+/+) were acclimatized several weeks before the experiments and kept isolated from external influences during the entire time course of the study. They were bred in a selective pathogen-free (SPF) environment and standardized conditions of temperature (21° C.), humidity (60%), light and dark cycles (12:12 h), with food and water provided ad libitum. Only male mice were used for this study in order to avoid a bias in gender with regard to levels of complement activity [59] and to susceptibility to brain injury which seems to be significantly influenced by female reproductive hormones [60, 61]. All experiments were performed in compliance with the standards of the Federation of European Laboratory Animal Science Association (FELASA) and were approved by the institutional animal care committee (Landesamt für Arbeitsschutz, Gesundheitsschutz und technische Sicherheit, Berlin, Germany, No. G0099/03 and No. G0308/04).

Brain injury model. Experimental closed head injury was performed in knockout (fB−/−) mice and wild-type littermates (fB+/+) of the C57BL/6 strain (n=6 per group and time-point) using a standardized weight-drop device, as previously described [13, 38, 62-64]. In brief, after induction of isoflurane anesthesia, the skull was exposed by a midline longitudinal scalp incision. A 333 g weight was dropped on the fixed skull from a height of 2 cm, resulting in a focal blunt injury to the left hemisphere. After trauma, the mice received supporting oxygenation with 100% O2 until fully awake and were then brought back to their cages. At defined time-points (t=4 h, 24 h, and 7 days), mice were euthanized and brain hemispheres were extracted for analysis by immunohistochemistry, TUNEL histochemistry, and SDS-PAGE/Western blot analysis. In addition, serum samples were collected for determination of complement anaphylatoxin C5a levels by ELISA and Western blot analysis of Bcl-2 (see below).

Sham-operated mice were kept under identical conditions as the trauma group and underwent the same procedures (anesthesia and scalp incision) except that no head injury was applied.

ELISA for Mouse C5a.

For determination of complement anaphylatoxin C5a levels in serum samples of head-injured and normal C57BL/6 control mice, an ELISA developed in the laboratory of Dr. P. A. Ward (Ann Arbor, Mich., USA) was used. In brief, ELISA plates (Immulon 4HBX, Thermo Labsystems, Milford, Mass., USA) were coated with purified monoclonal anti-mouse C5a IgG (5 μg/ml, BD Pharmingen, San Diego, Calif., USA). After blocking of non-specific binding sites with 1% milk (Roth, Karlsruhe, Germany) in PBS (Gibco-Invitrogen, Carlsbad, Calif., USA) containing 0.05% TWEEN 20 (Sigma-Aldrich, St. Louis, Mo., USA), the plate was coated with 100 ml serum diluted 1:20 (in 0.1% milk in PBS containing 0.05% TWEEN) and murine recombinant mouse C5a at defined concentrations for establishing the standard curve. After incubation and subsequent washing steps, biotinylated monoclonal anti-mouse C5a antibody was added at 500 ng/ml (BD Pharmingen) followed by washing steps and incubation with streptavidin-peroxidase at 400 ng/ml (Sigma). For colorimetric reaction, the substrate (0.4 mg/ml OPD with 0.4 mg/ml urea hydrogen peroxide in 0.05M phosphate citrate buffer; Sigma) was added and the color reaction was stopped with 3M sulfuric acid. The absorbance was read at 490 nm ("SpectraMax 190" reader, Molecular Devices, Sunnyvale, Calif., USA. All samples were analyzed in duplicate wells and results were calculated from the means of duplicate sample analysis. The standard curve was linear from 50 ng/ml to 0.1 ng/ml, which represents the lower limit of detection of this assay.

Western Blot.

All mice used in this study were screened by Western blot analysis for the presence of factor B in serum, as an internal quality control. The protein levels of the mitochondrial anti-apoptotic mediator Bcl-2 and of the pro-apoptotic Fas receptor were determined in homogenized mouse brains and matched serum samples at 4 h, 24 h and 7 d following head injury or sham operation in fB−/− and fB+/+ mice. The Western blot technique was previously described [32]. Briefly, mouse brains were extracted under anesthesia, separated into left and right hemispheres, and immediately homogenized in lysis buffer (Sigma) containing 100 mM TRIS-HCl (pH 7.5), 150 mM NaCl, 0.5% sodium dodecyl sulfate (SDS), 0.5% Nonidet P-40, 10 mg/ml aprotinin, 10 mg/ml leupeptin, 5 mg/ml pepstatin, 1 mM phenyl-methyl-sulfonyl fluoride in deionized water, using an Ultra Turrax Homogenizer® (IKA Werke, Staufen, Germany). After 15 min centrifugation at 13,000×g, the protein content of the supernatants was determined by commercially available colorimetric protein assay ("BCA Protein Assay", Pierce/Perbio Science, Bonn, Germany). A 60 μg sample of total protein was denatured in loading buffer and separated under reducing conditions on 12% SDS-polyacrylamide gels in parallel with a broad range prestained SDS-PAGE protein standard (Bio-Rad, Munich, Germany). Proteins were then transferred to Protran BA 83 nitrocellulose membranes (Schleicher & Schuell, Dassel, Germany) by electroblotting (Bio-Rad). The blots were blocked overnight and then incubated with either monoclonal anti-mouse Bcl-2 (Santa Cruz Biotechnology, Heidelberg, Germany), diluted 1:500, polyclonal rabbit anti-mouse Fas (clone A-20, Santa Cruz), diluted 1:200, polyclonal chicken anti-mouse anti-factor B, diluted 1:8,000 (kindly provided by Dr. Scott R. Barnum, University of Alabama at Birmingham, Ala., USA) as primary antibodies, and with a monoclonal anti-β-actin antibody (clone AC-15, Sigma) diluted 1:10,000, as internal control for ascertaining equal loading of the bands. After incubation with peroxidase-labelled secondary antibodies (Dako, Hamburg, Germany, and Santa Cruz Biotechnology, Heidelberg, Germany), diluted 1:5,000, antibody binding was visualized by a non-radioactive chemiluminescence technique using a commercially available ECL® Western blotting kit (Amersham Pharmacia Biotech, Freiburg, Germany). Equal transfer of proteins to the blotting membrane was confirmed by ponceau red staining (Sigma).

Immunohistochemistry.

For assessment of neuronal morphology, integrity, and apoptosis, extracted mouse brains were snap-frozen in liquid nitrogen, embedded in OCT compound (Sakura Finetek, Torrance, Calif.) and stored at −80° C. until used for analysis. Six to eight-micrometer thick coronal tissue sections were cut with a cryostat at −20° C. For immunohistochemistry, slides were fixed in acetone and then analyzed by a standard biotin/avidin/peroxidase technique with DAB-tetrahydrochloride as chromogen (Vector, Burlingame, Calif.), as previously described [13, 32]. The following primary antibodies were used as cell-markers: monoclonal anti-NeuN, at a titrated dilution of 1:2,000 (Chemicon, Hampshire, UK) for neurons; polyclonal rabbit anti-GFAP, 1:100 (Shandon Immunon, Pittsburgh, Pa., USA) for astrocytes; monoclonal rat anti-CD11b, 1:100, (Accurate Chemical, Westbury, N.Y., USA) for microglia; polyclonal goat-anti CD144, 1:200 (Santa Cruz) for endothelial cells. Non-immunized IgG (Vector) was used as negative control at equal dilutions as the omitted specific antibody.

To determine the extent of intracerebral neuronal cell death, TUNEL histochemistry was performed using a "Fluorescein In Situ Cell Death Detection Kit" (Roche Diagnostics GmbH, Mannheim, Germany), according to the manufacturer's instructions, as previously described [38]. Briefly, slides were dried for 30 min followed by fixation in 10% formalin solution at RT. After washing in PBS (three times for 3 min), sections were incubated in ice-cold ethanol-acetic acid solution (2:1) for 5 min at −20° C. Thereafter, they were washed in PBS and incubated in a permeabilization solution with 3% Triton X-100 in PBS for 60 min at RT, then incubated with the TdT enzyme in a reaction buffer containing fluorescein-dUTP for 90 min at 37° C. Negative control was performed using only the reaction buffer without TdT enzyme. Positive controls were performed by digesting equal brain sections with DNase grade I solution (500 U/ml; Roche) for 20 min at RT and always kept separate from the other samples thereafter. After labelling, the sections were washed again in PBS and to visualize the unstained (TUNEL-negative) cells, the sections were covered with VectashieldÒ mounting medium for fluorescence with DAPI (Vector). All samples were evaluated immediately after staining using an Axioskop 40 fluorescence microscope (Zeiss, Germany) at 460 nm for DAPI and 520 nm for TUNEL fluorescence and analyzed by Alpha digi doc 1201 software (Alpha Innotech, San Leandro, Calif., USA).

Statistical Analysis.

Statistical analysis was performed using commercially available software (SPSS 9.0 for Windows®). Differences in complement C5a levels in serum of fB−/− and fB+/+ mice were determined by the unpaired Student's t-test. A P-value<0.05 was considered statistically significant.

Results

Complement Activation is Attenuated in Brain-Injured fB−/− Mice.

Screening of serum samples from all fB−/− mice and wild-type littermates (fB+/+) used in the present study revealed that factor B was only detectable in serum of fB+/+ animals, but not in the fB−/− mice. These control experiments were performed to ascertain that the knockout mice are completely devoid of factor B in serum (data not shown).

Figure 10:
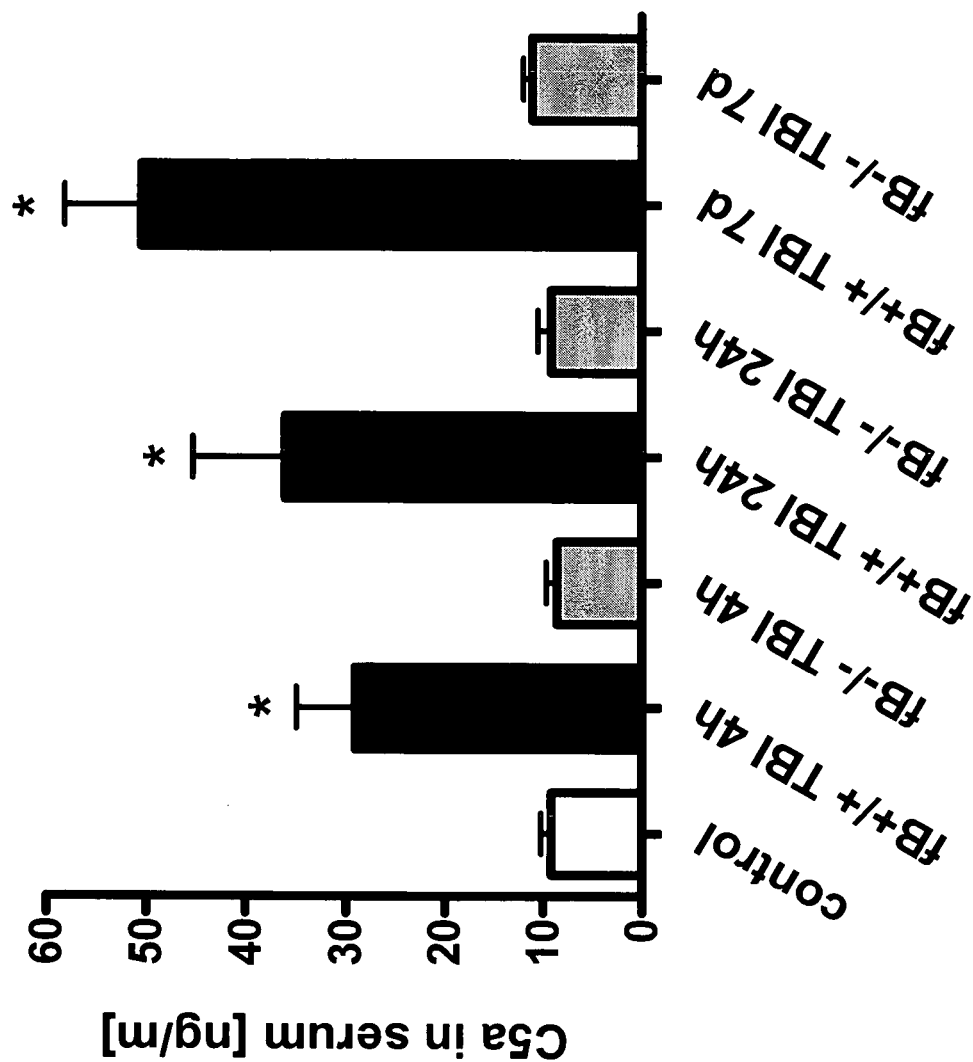
FIG. 10 is a graph showing that elevated C5a levels in serum of brain-injured C57BL/6 (fB+/+) mice are significantly attenuated in factor B gene-deficient (fB−/−) mice lacking a functional alternative complement pathway.

Referring to FIG. 10, serum samples from brain-injured fB+/+ and fB−/− mice of the C57BL/6 strain (n=6 per group and time-point) and from normal C57BL/6 mice (control; n=4) were analyzed by ELISA specific for mouse C5a (data in FIG. 10 are shown as mean levels±SD; *P<0.05, fB+/+ vs. control and fB+/+ vs. fB−/− mice. TBI, traumatic brain injury). Experimental closed head injury in wild-type C57BL/6 mice resulted in a systemic activation of the complement cascade, as determined by significantly elevated serum levels of the complement activation product C5a at all time-points assessed from 4 hours to 7 days (P<0.05 vs. normal mouse serum, unpaired Student's t-test; FIG. 10). In contrast, anaphylatoxin C5a serum levels were dramatically reduced in fB−/− mice at all corresponding time-points after head trauma, down to baseline levels in normal mice (P<0.05 vs. brain-injured fB+/+ mice, unpaired Student's t-test; FIG. 10). These data imply that the alternative pathway is the source for complement activation after brain injury, a notion which has only previously been substantiated for diseases outside the CNS, such as rheumatoid arthritis, autoimmune nephritis, and ischemia/reperfusion injuries [33, 37].

The Lack of Factor B Leads to Reduced Neuronal Cell Death after Head Injury.

Figure 12:
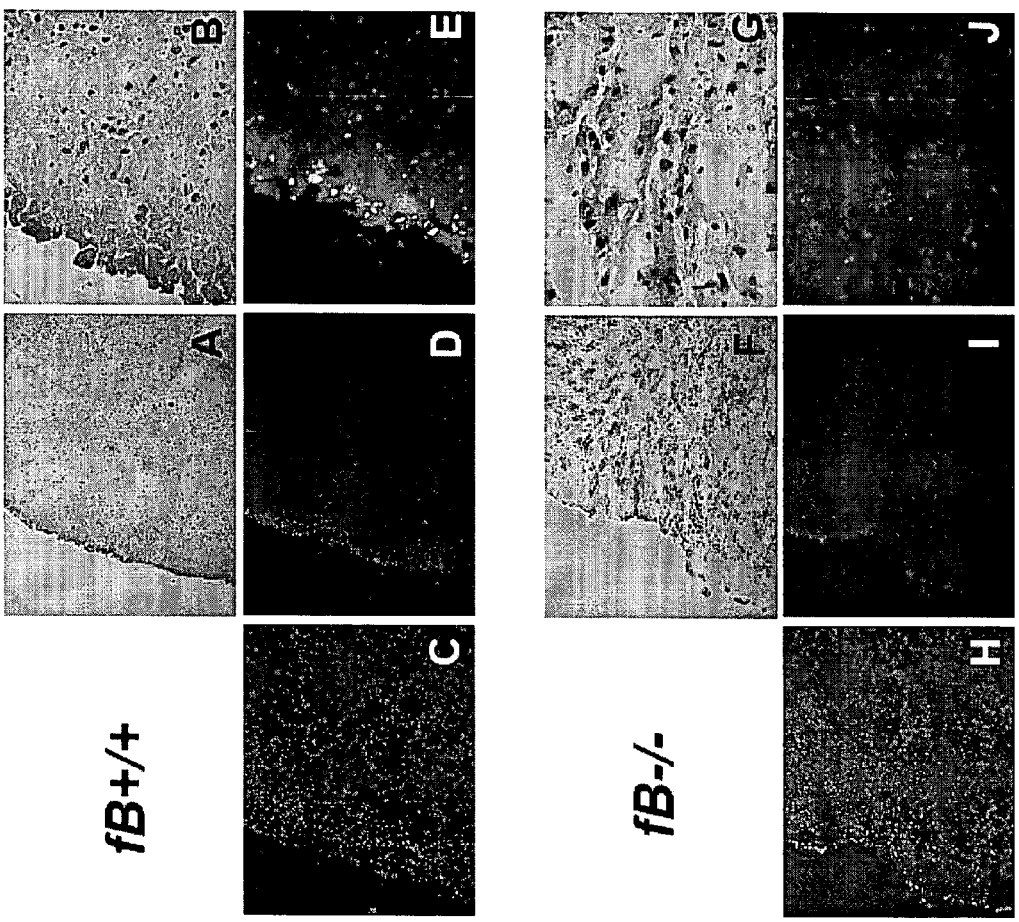
FIG. 12 is a digital image showing attenuated neuronal cell death in the injured hemisphere of factor B gene-deficient mice 4 hours after closed head injury.

As previously described, neuronal cell death was observed in injured brains of wild-type C57BL/6 mice for up to 7 days after closed head injury [38]. Referring to FIGS. 12-14, coronal cryosections of the left (injured) hemisphere of wild-type (fB+/+, panels A-E in each figure) and factor B knockout mice (fB−/−, panels F-J in each figure) were analyzed by immunohistochemistry with a specific antibody to the neuronal marker NeuN (A, B, F, G in each figure) or by TUNEL-histochemistry of adjacent sections (D, E, I, J in each figure). The overall cellular morphology of the TUNEL sections is revealed by DAPI nuclear stain (C, H in each figure). The panels B, E, G, J in each figure represent a 4-fold magnification of the respective panels A, D, F, I in each figure (Original magnifications: 100× (A, C, D, F, H, I), 400× (B, E, G, J)). An increase in TUNEL-positive cells was detected in the injured hemispheres of fB+/+ mice within 4 to 24 hours after trauma (FIGS. 12 and 13, respectively), persisting for up to 7 days (FIG. 14). The nuclear staining with 4',6'-diamino-2-phenylindole (DAPI; panels C and H of FIGS. 12-14) showed the cellular morphology in adjacent sections to those assessed by TUNEL histochemistry. Neurons were determined as the main TUNEL-positive cell-type by immunohistochemical staining of adjacent sections with the specific cell-marker NeuN (panels A, B, F and G of FIGS. 12-14). In contrast, the staining of astrocytes (anti-GFAP), microglia (anti-CD11b), and endothelial cells (anti-CD144) revealed that these resident cells in the brain do not exhibit a relevant TUNEL-staining in the present model of head injury (data not shown). Furthermore, neurons were confirmed as the predominant TUNEL-positive cell-type by their typical cellular size and morphology (as opposed to glial cells) and to the typical neuronal layers of TUNEL-positive cells in the injured cortex. These findings corroborate previously published data on neuronal apoptosis in the current and other experimental TBI models as well as in head-injured patients [38-42]. In contrast to the extent of neuronal cell death in brain-injured fB+/+ mice, the fB−/− animals showed a clear reduction in TUNEL-positive neurons in injured brains from 4 hours to 7 days after trauma (Panels D, E, I and J of FIGS. 12-14). These findings support the recently established concept of complement-dependent regulation of neuronal apoptosis [7, 10, 15, 43] and promote the in vivo significance of the alternative (factor B-dependent) pathway of complement activation in regulating the extent of secondary neurodegeneration after TBI.

This is the first study, to the best of the present inventors knowledge, which investigated exclusively the role of the alternative pathway in contributing to neuropathology after brain injury. The fB−/− mice have previously been shown to be protected from experimental demyelination in an animal model of multiple sclerosis [44]. The studies by Nataf and colleagues support the present inventors' present findings in that the genetic deficiency of factor B, which provokes the complete lack of a functional alternative complement activation pathway, plays an essential role for neuroprotection in models of autoimmune and traumatic CNS injury.

Upregulation of Bcl-2 and Downregulation of Fas in Injured fB−/− Brains

Figure 11:
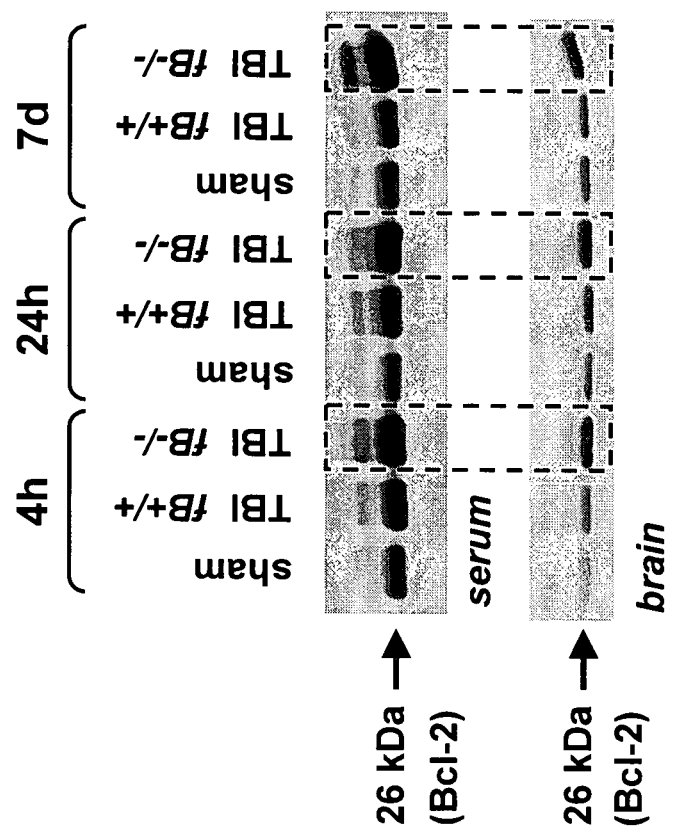
FIG. 11 is a digital image of a Western blot showing the upregulation of the anti-apoptotic mediator Bcl-2 in serum and brains of fB−/− mice after traumatic brain injury (TBI), as determined by Western blot analysis.

Posttraumatic neuronal apoptosis has been shown to be promoted by the Fas-mediated extrinsic pathway and by a suppression of the mitochondrial anti-apoptotic mediator Bcl-2 of the intrinsic pathway of apoptosis [45-51]. Referring to FIG. 11, homogenized brain tissue specimens from the injured hemispheres of sham-operated and head-injured fB+/+ and fB−/− mice were run out on SDS-PAGE, transferred to nitrocellulose membranes, and analyzed with specific monoclonal antibodies to Bcl-2 and detection by chemiluminescence assay (ECL® system, Amersham). The visualized 26 kDa band corresponding to mouse Bcl-2 is enhanced in the knockout mice at 24 hours, compared to head-injured wild-type littermates. Furthermore, a down-regulation in Fas receptor staining intensity was obvious in brain-injured knockout mice at all time-points assessed, compared to fB+/+ mice (data not shown). The exemplary blot is representative of three independent experiments.

More particularly, by Western blot analysis, the inventors found a marked upregulation of protective Bcl-2 protein levels in brain homogenates of head-injured fB−/− mice at 24 hours after trauma, compared to fB+/+littermates (FIG. 11). No apparent differences in Bcl-2 expression between knockout and wild-type mice were seen at other time-points after TBI (FIG. 11). With regard to the extrinsic pathway of apoptosis, a marked downregulation in Fas receptor expression was seen within 4 hours to 7 days after TBI in fB−/− mice, compared to fB+/+ animals (FIG. 11). Although these data are not quantitative, the differences in staining intensity of the 26 kDa (Bcl-2; FIG. 11) and 48 kDa bands (Fas; data not shown) appear more intense in the brain-injured knockout mice than in the corresponding wild-type littermates at the above-mentioned time-points. These findings indicate an involvement of the alternative pathway of complement activation in regulating neuronal apoptosis after TBI by suppression of Bcl-2 and induction of Fas receptor expression in the injured brain. Both aspects are critical in the regulation of post-injury neuronal apoptosis, as previously determined by other investigators in different model systems [45-47]. An experimental study on a controlled cortical impact brain injury model demonstrated that the cortical lesion volume was significantly reduced in transgenic mice with over-expression of the Bcl-2 gene by 7 days after trauma, compared to wild-type littermates [52]. Thus, Bcl-2 was attributed an important role in the regulation of the mitochondrial (intrinsic) pathway of apoptosis after TBI [4, 50, 52, 53].

The present inventors have previously shown that the pharmacological "pan"-inhibition of complement activation at the level of the C3 convertases by Crry-Ig, a murine recombinant chimeric fusion molecule, leads to enhanced intracerebral Bcl-2 gene and protein expression and to increased neuronal survival in the hippocampus of brain-injured mice [32]. In a model of murine autoimmune cerebritis, the blocking of complement activation by Crry-Ig resulted in a significant attenuation of neuronal apoptosis [15].

The data from the present study support the biological significance of the alternative pathway of complement activation in contributing to the neuropathological sequelae of TBI and provide the basis for future pharmacological studies with selective alternative pathway inhibitors, e.g. such as factor B antagonists [33, 54].

In summary, the present data provide first evidence of a major role of the alternative pathway of complement activation in contributing to the overall extent of posttraumatic complement activation (C5a generation) and to secondary neuronal cell death after brain injury (TUNEL, Bcl-2, and Fas data). This is a new and provocative discovery, since all previously published studies on experimental complement inhibition in TBI models have focused on interfering with the complement cascade at the "common junction" level of C3 convertases [26, 28-32] or further downstream in the cascade, e.g. by specific blocking of anaphylatoxin C5a or its receptor [30]. The hitherto underestimation of the pathophysiological role of the alternative complement pathway in the neuropathology of brain injury may be in part due to the historically established predominant role of the classical pathway in various neurological diseases [55, 56]. However, the results from the present study indicate that these insights may not necessarily reflect the "true" in vivo significance of the alternative complement pathway in a complex multifactorial neuroinflammatory disease, such as in the setting of TBI [57]. The fact that elevated factor B levels are present in the intrathecal compartment of severely head-injured patients [36] further supports the claim herein that the pharmacological targeting of factor B is reasonable and predictable.

REFERENCES FOR EXAMPLE 4

1. McArthur et al., Brain Pathol 2004, 14:185-94.
2. Gaetz, Clin Neurophysiol 2004, 115:4-18.
3. Eldadah et al., J Neurotrauma 2000, 17:811-829.
4. Raghupathi R, Brain Pathol 2004, 14:215-222.
5. Wong et al., Neurocrit Care 2005, 3:177-182.
6. Zhang et al., Crit Care 2005, 9:66-75.
7. Stahel et al., Brain Res Rev 1998, 27:243-56.
8. Cole et al., Clin Sci (Lond) 2003, 104:455-66.
9. Schmidt et al., Eur J Trauma 2004, 30:135-149.
10. Cole et al., Mol Immunol 2006, Jan. 5 [Epub ahead of print].
11. Farkas et al., J Physiol 1998, 507:679-87.
12. Nataf et al., Trends Neurosci 1999, 22:397-402.
13. Stahel et al., J Neuroimmunol 2000, 109:164-72.
14. O'Barr et al., J Immunol 2001, 166:4154-4162.
15. Alexander et al., J Immunol 2005, 175:8312-8319.
16. Morgan, Crit Rev Immunol 1999, 19:173-98.
17. Singhrao et al., Am J Pathol 2000, 157:905-18.
18. Bellander et al., J Neurotrauma 2001, 18:1295-311.
19. Ohlsson et al., J Neurotrauma 2003, 20:895-904.
20. Ohlsson and Havton, Neurosci Lett 2005, Nov. 10 [Epub ahead of print].
21. Casarsa et al., Eur J Immunol 2003, 33:1260-1270.
22. Xiong et al., J Neurosci 2003, 23:955-60.
23. Bellander et al., J Neurosurg 1996, 85:468-75.
24. Keeling et al., J Neuroimmunol 2000, 105:20-30.
5. Kyrkanides et al., J Neuroimmunol 2001, 119:268-277.
26. Rancan et al., J Cereb Blood Flow Metab 2003, 23:1070-4.
27. Stahel et al., J Neurotrauma 2001, 18:773-81.
28. Kaczorowski et al., J Cereb Blood Flow Metab 1995, 15:860-4.
29. Hicks et al., J Neurotrauma 2002, 19:705-14.
30. Sewell et al., J Neuroimmunol 2004, 155:55-63.
31. Pillay et al., Ann N Y Acad Sci 2005, 1056:450-461.
32. Leinhase et al., Exp Neurol 2006 (in press).
33. Holers and Thurman, Mol Immunol 2004, 41:147-152.
34. Thurman et al., J Immunol 2003, 170:1517-1523.
35. Thurman et al., Kidney Int 2005, 67:524-30.
36. Kossmann et al., J Neuroimmunol 1997, 73:63-9.

37. Thurman and Holers, J Immunol 2006, 176:1305-1310.
38. Stahel et al., J Cereb Blood Flow Metab 2000, 20:369-80.
39. Rink et al., Am J Pathol 1995, 147:1575-1583.
40. Yakovlev et al., J Neurosci 1997, 17:7415-7424.
41. Williams et al., Acta Neuropathol 2001, 102:581-590.
42. Marciano et al., J Neurosci 2004, 24:2866-2876.
43. Elward et al., J Biol Chem 2005, 280:36342-54.
44. Nataf et al., J Immunol 2000, 165:5867-5873.
45. Felderhoff-Mueser et al., Neurobiol Dis 2002, 11:231-245.
46. Qiu et al., J Neurosci 2002, 22:3504-3511.
47. Raghupathi et al., Neuroscience 2002, 110:605-616.
48. Raghupathi et al., J Neurotrauma 2003, 20:421-435.
49. Strauss et al., Neurotox Res 2004, 6:333-342.
50. Mohamad et al., Biocell 2005, 29:149-161.
51. Friedlander, N Engl J Med 2003, 348:1365-1375.
52. Raghupathi et al., J Cereb Blood Flow Metab 1998, 18:1259-69.
53. Shacka et al., Curr Drug Targets CNS Neurol Disord 2005, 4:25-39.
54. Thurman et al., Mol Immunol 2005, 42:87-97.
55. Morgan and Gasque, Immunol Today 1996, 17:461-6.
56. Barnum, Mol Med 1999, 5:569-82.
57. Schmidt et al., Brain Res Rev 2005, 48:388-399.
58. Matsumoto et al., Proc. Natl. Acad. Sci. USA 1997, 94:8720-8725.
59. Holers, Immunopharmacology 2000, 49:125-31.
60. Roof and Hall, J Neurotrauma 2000, 17:367-388.
61. Yao et al., J Neurotrauma 2005, 22:656-658.
62. Chen et al., J Neurotrauma 1996, 13:557-68.
63. Yatsiv et al., J Cereb Blood Flow Metab 2002, 22:971-8.
64. Yatsiv et al., FASEB J 2005, 19:1701-1703.

Each of the references cited in this application is incorporated by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to reduce or prevent at least one symptom of physiological damage resulting from traumatic brain injury (TBI) or spinal cord injury (SCI) in an animal, or enhance recovery from TBI or SCI in the animal, comprising selectively inhibiting the alternative complement pathway in an animal that has experienced TBI or SCI, respectively, wherein the step of inhibiting comprises administering to the animal an antibody or antigen-binding fragment thereof which specifically binds to factor B, wherein the antibody or antigen-binding fragment thereof prevents or inhibits factor B from binding to activated C3.

2. The method of claim 1, wherein the symptom of TBI or SCI is selected from the group consisting of: posttraumatic neurological impairment, weight loss, neuronal cell death, lower limb motor function, and walking ability.

3. The method of claim 1, wherein the antibody or antigen-binding fragment thereof selectively binds to factor B within the third short consensus repeat (SCR) domain and prevents formation of a C3bBb complex.

4. The method of claim 1, wherein the antibody or antigen-binding fragment thereof prevents or inhibits cleavage of factor B by factor D.

5. The method of claim 1, wherein the antibody or antigen binding fragment thereof binds to the third short consensus repeat (SCR) domain of human factor B.

6. The method of claim 1, wherein the antibody or antigen binding fragment thereof selectively binds to an epitope in the third SCR domain of factor B, wherein the epitope is the same epitope recognized by the monoclonal antibody 1379 (produced by ATCC Deposit No. PTA-6230).

7. The method of claim 1, wherein the antibody or antigen binding fragment thereof selectively binds to factor B from multiple mammalian species.

8. The method of claim 7, wherein the antibody or antigen binding fragment thereof selectively binds to factor B from human and an animal selected from the group consisting of non-human primate, mouse, rat, pig, horse and rabbit.

9. The method of claim 1, wherein the antibody or antigen-binding fragment thereof is of a non-complement activating isotype or subclass.

10. The method of claim 1, wherein the antibody or antigen-binding fragment thereof is selected from the group consisting of: a monoclonal antibody or antigen-binding fragment thereof, a humanized antibody or antigen-binding fragment thereof, a bispecific antibody or antigen-binding fragment thereof, a CDR-grafted antibody or antigen-binding fragment thereof, a chimeric antibody or antigen-binding fragment thereof, and a monovalent antibody or antigen-binding fragment thereof.

11. The method of claim 1, wherein the antibody or antigen-binding fragment thereof is an antigen-binding fragment selected from the group consisting of an Fab, an Fv, an Fab', and an $F(ab')_2$.

12. The method of claim 1, wherein the antibody is the monoclonal antibody 1379 (produced by ATCC Deposit No. PTA-6230) or a genetically engineered antibody originated from the monoclonal antibody 1379.

13. The method of claim 1, wherein the animal has experienced TBI, and wherein the antibody or antigen-binding fragment thereof is administered intravenously or to the brain of the animal.

14. The method of claim 1, wherein the animal has experienced SCI, and wherein the antibody or antigen-binding fragment thereof is administered to the spinal cord or epidural space of the spinal cord of the animal.

15. The method of claim 1, wherein the antibody or antigen-binding fragment thereof agent is administered to the animal in an amount effective to measurably reduce at least one symptom of physiological damage resulting from TBI or SCI in the animal as compared to in the absence of administration of the antibody or antigen-binding fragment thereof.

16. The method of claim 1, wherein the animal has experienced TBI, and wherein the antibody or antigen-binding fragment thereof is administered in an amount effective to maintain a cerebral perfusion pressure (CPP) of above 70-80 mm Hg, or in an amount effective to lower intracranial pressure (ICP).

17. The method of claim 1, wherein the animal has experienced SCI, and wherein the antibody or antigen-binding fragment thereof is administered in an amount effective to reduce swelling in the spinal cord.

18. The method of claim 1, wherein the antibody or antigen-binding fragment thereof is administered in a pharmaceutically acceptable carrier that is capable of crossing the blood-brain barrier or that is an injectable excipient.

19. The method of claim 1, wherein the animal has experienced TBI, and wherein the method further comprises administering to the animal another compound for treating a symptom of TBI selected from the group consisting of: a physical impairment, a cognitive impairment, and a psycho-social-behavioral-emotional impairment.

20. The method of claim 19, wherein the compound is selected from the group consisting of: an osmotic drug, a sedative, an analgesic, a muscle relaxant, and a barbiturate.

21. The method of claim 1, wherein the animal has experienced SCI, and wherein the method further comprises administering a steroid to the animal.

22. The method of claim 1, further comprising treating the animal for TBI by a protocol selected from the group consisting of: reduction of mass lesions by surgical evacuation of intracranial hematomas; reduction of brain swelling with osmotic drugs; therapeutic drainage of cerebrospinal fluid (CSF) through intraventricular catheters; computerized tomography (CT) scans; sedation; analgesia; muscle relaxation; moderate hyperventilation; moderate hypothermia; and barbiturate coma.

23. The method of claim 1, further comprising treating the animal for SCI by a protocol selected from the group consisting of: administration of steroids; immobilization of the spine; decompression surgery; surgery to stabilize the vertebrae; surgery to realign the vertebrae; and traction.

24. The method of claim 1, wherein the symptom of TBI is selected from the group consisting of: posttraumatic neurological impairment, weight loss, and neuronal cell death.

25. The method of claim 1, wherein the animal is a human.

* * * * *

UNITED STATES PATENT AND TRADEMARK OFFICE
CERTIFICATE OF CORRECTION

Page 1 of 1

PATENT NO. : 8,911,733 B2
APPLICATION NO. : 11/441828
DATED : December 16, 2014
INVENTOR(S) : V. Michael Holers et al.

It is certified that error appears in the above-identified patent and that said Letters Patent is hereby corrected as shown below:

On the title page, under abstract "25 Claims, 15 Drawing Sheets" should read --26 Claims, 15 Drawing Sheets--.

In the claims

Column 61, Line 40, Claim 15, replace "fragment thereof agent is" with --fragment thereof is--.

Column 62, Line 44, insert the following claim:

--Claim 26. The method of claim 1, wherein the symptom of SCI is lower limb motor function or walking ability.--.

Signed and Sealed this
Twenty-second Day of March, 2016

Michelle K. Lee
*Director of the United States Patent and Trademark Office*

SEQUENCE LISTING

<160> NUMBER OF SEQ ID NOS: 8

<210> SEQ ID NO 1
<211> LENGTH: 764
<212> TYPE: PRT
<213> ORGANISM: Homo sapiens

<400> SEQUENCE: 1

```
Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
```

-continued

```
                225                 230                 235                 240
Thr Ile Glu Gly Val Asp Ala Glu Asp Gly His Gly Pro Gly Glu Gln
                    245                 250                 255
Gln Lys Arg Lys Ile Val Leu Asp Pro Ser Gly Ser Met Asn Ile Tyr
                    260                 265                 270
Leu Val Leu Asp Gly Ser Asp Ser Ile Gly Ala Ser Asn Phe Thr Gly
                    275                 280                 285
Ala Lys Lys Cys Leu Val Asn Leu Ile Glu Lys Val Ala Ser Tyr Gly
                    290                 295                 300
Val Lys Pro Arg Tyr Gly Leu Val Thr Tyr Ala Thr Tyr Pro Lys Ile
305                 310                 315                 320
Trp Val Lys Val Ser Glu Ala Asp Ser Ser Asn Ala Asp Trp Val Thr
                    325                 330                 335
Lys Gln Leu Asn Glu Ile Asn Tyr Glu Asp His Lys Leu Lys Ser Gly
                    340                 345                 350
Thr Asn Thr Lys Lys Ala Leu Gln Ala Val Tyr Ser Met Met Ser Trp
                    355                 360                 365
Pro Asp Asp Val Pro Pro Glu Gly Trp Asn Arg Thr Arg His Val Ile
370                 375                 380
Ile Leu Met Thr Asp Gly Leu His Asn Met Gly Gly Asp Pro Ile Thr
385                 390                 395                 400
Val Ile Asp Glu Ile Arg Asp Leu Leu Tyr Ile Gly Lys Asp Arg Lys
                    405                 410                 415
Asn Pro Arg Glu Asp Tyr Leu Asp Val Tyr Val Phe Gly Val Gly Pro
                    420                 425                 430
Leu Val Asn Gln Val Asn Ile Asn Ala Leu Ala Ser Lys Lys Asp Asn
                    435                 440                 445
Glu Gln His Val Phe Lys Val Lys Asp Met Glu Asn Leu Glu Asp Val
                    450                 455                 460
Phe Tyr Gln Met Ile Asp Glu Ser Gln Ser Leu Ser Leu Cys Gly Met
465                 470                 475                 480
Val Trp Glu His Arg Lys Gly Thr Asp Tyr His Lys Gln Pro Trp Gln
                    485                 490                 495
Ala Lys Ile Ser Val Ile Arg Pro Ser Lys Gly His Glu Ser Cys Met
                    500                 505                 510
Gly Ala Val Val Ser Glu Tyr Phe Val Leu Thr Ala Ala His Cys Phe
                    515                 520                 525
Thr Val Asp Asp Lys Glu His Ser Ile Lys Val Ser Val Gly Gly Glu
                    530                 535                 540
Lys Arg Asp Leu Glu Ile Glu Val Val Leu Phe His Pro Asn Tyr Asn
545                 550                 555                 560
Ile Asn Gly Lys Lys Glu Ala Gly Ile Pro Glu Phe Tyr Asp Tyr Asp
                    565                 570                 575
Val Ala Leu Ile Lys Leu Lys Asn Lys Leu Lys Tyr Gly Gln Thr Ile
                    580                 585                 590
Arg Pro Ile Cys Leu Pro Cys Thr Glu Gly Thr Thr Arg Ala Leu Arg
                    595                 600                 605
Leu Pro Pro Thr Thr Thr Cys Gln Gln Gln Lys Glu Glu Leu Leu Pro
                    610                 615                 620
Ala Gln Asp Ile Lys Ala Leu Phe Val Ser Glu Glu Lys Lys Leu Leu
625                 630                 635                 640
Thr Arg Lys Glu Val Tyr Ile Lys Asn Gly Asp Lys Lys Gly Ser Cys
                    645                 650                 655
```

-continued

```
Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Val Ser Pro
        675                 680                 685

Tyr Ala Asp Pro Asn Thr Cys Arg Gly Asp Ser Gly Gly Pro Leu Ile
        690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
            740                 745                 750

Lys Glu Lys Leu Gln Asp Glu Asp Leu Gly Phe Leu
        755                 760

<210> SEQ ID NO 2
<211> LENGTH: 739
<212> TYPE: PRT
<213> ORGANISM: Homo sapiens

<400> SEQUENCE: 2

Thr Pro Trp Ser Leu Ala Arg Pro Gln Gly Ser Cys Ser Leu Glu Gly
1               5                   10                  15

Val Glu Ile Lys Gly Gly Ser Phe Arg Leu Leu Gln Glu Gly Gln Ala
                20                  25                  30

Leu Glu Tyr Val Cys Pro Ser Gly Phe Tyr Pro Tyr Pro Val Gln Thr
            35                  40                  45

Arg Thr Cys Arg Ser Thr Gly Ser Trp Ser Thr Leu Lys Thr Gln Asp
        50                  55                  60

Gln Lys Thr Val Arg Lys Ala Glu Cys Arg Ala Ile His Cys Pro Arg
65                  70                  75                  80

Pro His Asp Phe Glu Asn Gly Glu Tyr Trp Pro Arg Ser Pro Tyr Tyr
                85                  90                  95

Asn Val Ser Asp Glu Ile Ser Phe His Cys Tyr Asp Gly Tyr Thr Leu
            100                 105                 110

Arg Gly Ser Ala Asn Arg Thr Cys Gln Val Asn Gly Arg Trp Ser Gly
        115                 120                 125

Gln Thr Ala Ile Cys Asp Asn Gly Ala Gly Tyr Cys Ser Asn Pro Gly
130                 135                 140

Ile Pro Ile Gly Thr Arg Lys Val Gly Ser Gln Tyr Arg Leu Glu Asp
145                 150                 155                 160

Ser Val Thr Tyr His Cys Ser Arg Gly Leu Thr Leu Arg Gly Ser Gln
                165                 170                 175

Arg Arg Thr Cys Gln Glu Gly Gly Ser Trp Ser Gly Thr Glu Pro Ser
            180                 185                 190

Cys Gln Asp Ser Phe Met Tyr Asp Thr Pro Gln Glu Val Ala Glu Ala
        195                 200                 205

Phe Leu Ser Ser Leu Thr Glu Thr Ile Glu Gly Val Asp Ala Glu Asp
    210                 215                 220

Gly His Gly Pro Gly Glu Gln Gln Lys Arg Lys Ile Val Leu Asp Pro
225                 230                 235                 240

Ser Gly Ser Met Asn Ile Tyr Leu Val Leu Asp Gly Ser Asp Ser Ile
                245                 250                 255

Gly Ala Ser Asn Phe Thr Gly Ala Lys Lys Cys Leu Val Asn Leu Ile
```

-continued

```
                260                 265                 270
Glu Lys Val Ala Ser Tyr Gly Val Lys Pro Arg Tyr Gly Leu Val Thr
                275                 280                 285

Tyr Ala Thr Tyr Pro Lys Ile Trp Val Lys Val Ser Glu Ala Asp Ser
        290                 295                 300

Ser Asn Ala Asp Trp Val Thr Lys Gln Leu Asn Glu Ile Asn Tyr Glu
305                 310                 315                 320

Asp His Lys Leu Lys Ser Gly Thr Asn Thr Lys Lys Ala Leu Gln Ala
                325                 330                 335

Val Tyr Ser Met Met Ser Trp Pro Asp Asp Val Pro Pro Glu Gly Trp
                340                 345                 350

Asn Arg Thr Arg His Val Ile Ile Leu Met Thr Asp Gly Leu His Asn
                355                 360                 365

Met Gly Gly Asp Pro Ile Thr Val Ile Asp Glu Ile Arg Asp Leu Leu
        370                 375                 380

Tyr Ile Gly Lys Asp Arg Lys Asn Pro Arg Glu Asp Tyr Leu Asp Val
385                 390                 395                 400

Tyr Val Phe Gly Val Gly Pro Leu Val Asn Gln Val Asn Ile Asn Ala
                405                 410                 415

Leu Ala Ser Lys Lys Asp Asn Glu Gln His Val Phe Lys Val Lys Asp
                420                 425                 430

Met Glu Asn Leu Glu Asp Val Phe Tyr Gln Met Ile Asp Glu Ser Gln
                435                 440                 445

Ser Leu Ser Leu Cys Gly Met Val Trp Glu His Arg Lys Gly Thr Asp
        450                 455                 460

Tyr His Lys Gln Pro Trp Gln Ala Lys Ile Ser Val Ile Arg Pro Ser
465                 470                 475                 480

Lys Gly His Glu Ser Cys Met Gly Ala Val Val Ser Glu Tyr Phe Val
                485                 490                 495

Leu Thr Ala Ala His Cys Phe Thr Val Asp Asp Lys Glu His Ser Ile
                500                 505                 510

Lys Val Ser Val Gly Gly Glu Lys Arg Asp Leu Glu Ile Glu Val Val
                515                 520                 525

Leu Phe His Pro Asn Tyr Asn Ile Asn Gly Lys Lys Glu Ala Gly Ile
        530                 535                 540

Pro Glu Phe Tyr Asp Tyr Asp Val Ala Leu Ile Lys Leu Lys Asn Lys
545                 550                 555                 560

Leu Lys Tyr Gly Gln Thr Ile Arg Pro Ile Cys Leu Pro Cys Thr Glu
                565                 570                 575

Gly Thr Thr Arg Ala Leu Arg Leu Pro Pro Thr Thr Thr Cys Gln Gln
                580                 585                 590

Gln Lys Glu Glu Leu Leu Pro Ala Gln Asp Ile Lys Ala Leu Phe Val
                595                 600                 605

Ser Glu Glu Glu Lys Lys Leu Thr Arg Lys Glu Val Tyr Ile Lys Asn
                610                 615                 620

Gly Asp Lys Lys Gly Ser Cys Glu Arg Asp Ala Gln Tyr Ala Pro Gly
625                 630                 635                 640

Tyr Asp Lys Val Lys Asp Ile Ser Glu Val Val Thr Pro Arg Phe Leu
                645                 650                 655

Cys Thr Gly Gly Val Ser Pro Tyr Ala Asp Pro Asn Thr Cys Arg Gly
                660                 665                 670

Asp Ser Gly Gly Pro Leu Ile Val His Lys Arg Ser Arg Phe Ile Gln
                675                 680                 685
```

```
Val Gly Val Ile Ser Trp Gly Val Asp Val Cys Lys Asn Gln Lys
    690             695             700
Arg Gln Lys Gln Val Pro Ala His Ala Arg Asp Phe His Ile Asn Leu
705             710             715             720
Phe Gln Val Leu Pro Trp Leu Lys Glu Lys Leu Gln Asp Glu Asp Leu
            725             730             735
Gly Phe Leu

<210> SEQ ID NO 3
<211> LENGTH: 70
<212> TYPE: PRT
<213> ORGANISM: Homo sapiens

<400> SEQUENCE: 3

Ala Arg Pro Gln Gly Ser Cys Ser Leu Glu Gly Val Glu Ile Lys Gly
1               5                   10                  15
Gly Ser Phe Arg Leu Leu Gln Glu Gly Gln Ala Leu Glu Tyr Val Cys
            20                  25                  30
Pro Ser Gly Phe Tyr Pro Tyr Pro Val Gln Thr Arg Thr Cys Arg Ser
        35                  40                  45
Thr Gly Ser Trp Ser Thr Leu Lys Thr Gln Asp Gln Lys Thr Val Arg
    50                  55                  60
Lys Ala Glu Cys Arg Ala
65                  70

<210> SEQ ID NO 4
<211> LENGTH: 60
<212> TYPE: PRT
<213> ORGANISM: Homo sapiens

<400> SEQUENCE: 4

Ile His Cys Pro Arg Pro His Asp Phe Glu Asn Gly Glu Tyr Trp Pro
1               5                   10                  15
Arg Ser Pro Tyr Tyr Asn Val Ser Asp Glu Ile Ser Phe His Cys Tyr
            20                  25                  30
Asp Gly Tyr Thr Leu Arg Gly Ser Ala Asn Arg Thr Cys Gln Val Asn
        35                  40                  45
Gly Arg Trp Ser Gly Gln Thr Ala Ile Cys Asp Asn
    50                  55                  60

<210> SEQ ID NO 5
<211> LENGTH: 48
<212> TYPE: PRT
<213> ORGANISM: Homo sapiens

<400> SEQUENCE: 5

Gly Tyr Cys Ser Asn Pro Gly Ile Pro Ile Gly Thr Arg Lys Val Gly
1               5                   10                  15
Ser Gln Tyr Arg Leu Glu Asp Ser Val Thr Tyr His Cys Ser Arg Gly
            20                  25                  30
Leu Thr Leu Arg Gly Ser Gln Arg Arg Thr Cys Gln Glu Gly Gly Ser
        35                  40                  45

<210> SEQ ID NO 6
<211> LENGTH: 761
<212> TYPE: PRT
<213> ORGANISM: Mus musculus

<400> SEQUENCE: 6
```

-continued

```
Met Glu Ser Pro Gln Leu Cys Leu Val Leu Leu Val Leu Gly Phe Ser
1               5                   10                  15

Ser Gly Gly Val Ser Ala Thr Pro Val Leu Glu Ala Arg Pro Gln Val
            20                  25                  30

Ser Cys Ser Leu Glu Gly Val Glu Ile Lys Gly Gly Ser Phe Gln Leu
        35                  40                  45

Leu Gln Gly Gly Gln Ala Leu Glu Tyr Leu Cys Pro Ser Gly Phe Tyr
    50                  55                  60

Pro Tyr Pro Val Gln Thr Arg Thr Cys Arg Ser Thr Gly Ser Trp Ser
65                  70                  75                  80

Asp Leu Gln Thr Arg Asp Gln Lys Ile Val Gln Lys Ala Glu Cys Arg
                85                  90                  95

Ala Ile Arg Cys Pro Arg Pro Gln Asp Phe Glu Asn Gly Glu Phe Trp
                100                 105                 110

Pro Arg Ser Pro Phe Tyr Asn Leu Ser Asp Gln Ile Ser Phe Gln Cys
            115                 120                 125

Tyr Asp Gly Tyr Val Leu Arg Gly Ser Ala Asn Arg Thr Cys Gln Glu
        130                 135                 140

Asn Gly Arg Trp Asp Gly Gln Thr Ala Ile Cys Asp Asp Gly Ala Gly
145                 150                 155                 160

Tyr Cys Pro Asn Pro Gly Ile Pro Ile Gly Thr Arg Lys Val Gly Ser
                165                 170                 175

Gln Tyr Arg Leu Glu Asp Ile Val Thr Tyr His Cys Ser Arg Gly Leu
            180                 185                 190

Val Leu Arg Gly Ser Gln Lys Arg Lys Cys Gln Glu Gly Gly Ser Trp
        195                 200                 205

Ser Gly Thr Glu Pro Ser Cys Gln Asp Ser Phe Met Tyr Asp Ser Pro
210                 215                 220

Gln Glu Val Ala Glu Ala Phe Leu Ser Ser Leu Thr Glu Thr Ile Glu
225                 230                 235                 240

Gly Ala Asp Ala Glu Asp Gly His Ser Pro Gly Glu Gln Gln Lys Arg
                245                 250                 255

Lys Ile Val Leu Asp Pro Ser Gly Ser Met Asn Ile Tyr Leu Val Leu
            260                 265                 270

Asp Gly Ser Asp Ser Ile Gly Ser Ser Asn Phe Thr Gly Ala Lys Arg
        275                 280                 285

Cys Leu Thr Asn Leu Ile Glu Lys Val Ala Ser Tyr Gly Val Arg Pro
290                 295                 300

Arg Tyr Gly Leu Leu Thr Tyr Ala Thr Val Pro Lys Val Leu Val Arg
305                 310                 315                 320

Val Ser Asp Glu Arg Ser Ser Asp Ala Asp Trp Val Thr Glu Lys Leu
                325                 330                 335

Asn Gln Ile Ser Tyr Glu Asp His Lys Leu Lys Ser Gly Thr Asn Thr
            340                 345                 350

Lys Arg Ala Leu Gln Ala Val Tyr Ser Met Met Ser Trp Ala Gly Asp
        355                 360                 365

Ala Pro Pro Glu Gly Trp Asn Arg Thr Arg His Val Ile Ile Ile Met
370                 375                 380

Thr Asp Gly Leu His Asn Met Gly Gly Asn Pro Val Thr Val Ile Gln
385                 390                 395                 400

Asp Ile Arg Ala Leu Leu Asp Ile Gly Arg Asp Pro Lys Asn Pro Arg
                405                 410                 415
```

Glu Asp Tyr Leu Asp Val Tyr Val Phe Gly Val Gly Pro Leu Val Asp
              420                 425                 430

Ser Val Asn Ile Asn Ala Leu Ala Ser Lys Lys Asp Asn Glu His His
              435                 440                 445

Val Phe Lys Val Lys Asp Met Glu Asp Leu Glu Asn Val Phe Tyr Gln
450                 455                 460

Met Ile Asp Glu Thr Lys Ser Leu Ser Leu Cys Gly Met Val Trp Glu
465                 470                 475                 480

His Lys Lys Gly Asn Asp Tyr His Lys Gln Pro Trp Gln Ala Lys Ile
              485                 490                 495

Ser Val Thr Arg Pro Leu Lys Gly His Glu Thr Cys Met Gly Ala Val
              500                 505                 510

Val Ser Glu Tyr Phe Val Leu Thr Ala Ala His Cys Phe Met Val Asp
              515                 520                 525

Asp Gln Lys His Ser Ile Lys Val Ser Val Gly Gly Gln Arg Arg Asp
              530                 535                 540

Leu Glu Ile Glu Val Leu Phe His Pro Lys Tyr Asn Ile Asn Gly
545                 550                 555                 560

Lys Lys Ala Glu Gly Ile Pro Glu Phe Tyr Asp Tyr Asp Val Ala Leu
              565                 570                 575

Val Lys Leu Lys Asn Lys Leu Lys Tyr Gly Gln Thr Leu Arg Pro Ile
              580                 585                 590

Cys Leu Pro Cys Thr Glu Gly Thr Thr Arg Ala Leu Arg Leu Pro Gln
              595                 600                 605

Thr Ala Thr Cys Lys Gln His Lys Glu Gln Leu Leu Pro Val Lys Asp
              610                 615                 620

Val Lys Ala Leu Phe Val Ser Glu Gln Gly Lys Ser Leu Thr Arg Lys
625                 630                 635                 640

Glu Val Tyr Ile Lys Asn Gly Asp Lys Lys Ala Ser Cys Glu Arg Asp
              645                 650                 655

Ala Thr Lys Ala Gln Gly Tyr Glu Lys Val Lys Asp Ala Ser Glu Val
              660                 665                 670

Val Thr Pro Arg Phe Leu Cys Thr Gly Gly Val Asp Pro Tyr Ala Asp
              675                 680                 685

Pro Asn Thr Cys Lys Gly Asp Ser Gly Gly Pro Leu Ile Val His Lys
              690                 695                 700

Arg Ser Arg Phe Ile Gln Val Gly Val Ile Ser Trp Gly Val Val Asp
705                 710                 715                 720

Val Cys Arg Asp Gln Arg Gln Gln Leu Val Pro Ser Tyr Ala Arg
              725                 730                 735

Asp Phe His Ile Asn Leu Phe Gln Val Leu Pro Trp Leu Lys Asp Lys
              740                 745                 750

Leu Lys Asp Glu Asp Leu Gly Phe Leu
              755                 760

<210> SEQ ID NO 7
<211> LENGTH: 253
<212> TYPE: PRT
<213> ORGANISM: Homo sapiens

<400> SEQUENCE: 7

Met His Ser Trp Glu Arg Leu Ala Val Leu Val Leu Leu Gly Ala Ala
1               5                   10                  15

Ala Cys Ala Ala Pro Pro Arg Gly Arg Ile Leu Gly Gly Arg Glu Ala
              20                  25                  30

```
Glu Ala His Ala Arg Pro Tyr Met Ala Ser Val Gln Leu Asn Gly Ala
            35                  40                  45

His Leu Cys Gly Gly Val Leu Val Ala Glu Gln Trp Val Leu Ser Ala
 50                  55                  60

Ala His Cys Leu Glu Asp Ala Asp Gly Lys Val Gln Val Leu Leu
 65                  70                  75                  80

Gly Ala His Ser Leu Ser Gln Pro Glu Pro Ser Lys Arg Leu Tyr Asp
                 85                  90                  95

Val Leu Arg Ala Val Pro His Pro Asp Ser Gln Pro Asp Thr Ile Asp
            100                 105                 110

His Asp Leu Leu Leu Gln Leu Ser Glu Lys Ala Thr Leu Gly Pro
            115                 120                 125

Ala Val Arg Pro Leu Pro Trp Gln Arg Val Asp Arg Asp Val Ala Pro
130                 135                 140

Gly Thr Leu Cys Asp Val Ala Gly Trp Gly Ile Val Asn His Ala Gly
145                 150                 155                 160

Arg Arg Pro Asp Ser Leu Gln His Val Leu Leu Pro Val Leu Asp Arg
                165                 170                 175

Ala Thr Cys Asn Arg Arg Thr His His Asp Gly Ala Ile Thr Glu Arg
            180                 185                 190

Leu Met Cys Ala Glu Ser Asn Arg Arg Asp Ser Cys Lys Gly Asp Ser
            195                 200                 205

Gly Gly Pro Leu Val Cys Gly Gly Val Leu Glu Gly Val Val Thr Ser
            210                 215                 220

Gly Ser Arg Val Cys Gly Asn Arg Lys Lys Pro Gly Ile Tyr Thr Arg
225                 230                 235                 240

Val Ala Ser Tyr Ala Ala Trp Ile Asp Ser Val Leu Ala
                245                 250

<210> SEQ ID NO 8
<211> LENGTH: 469
<212> TYPE: PRT
<213> ORGANISM: Homo sapiens

<400> SEQUENCE: 8

Met Ile Thr Glu Gly Ala Gln Ala Pro Arg Leu Leu Pro Pro Leu
1               5                   10                  15

Leu Leu Leu Leu Thr Leu Pro Ala Thr Gly Ser Asp Pro Val Leu Cys
                20                  25                  30

Phe Thr Gln Tyr Glu Glu Ser Ser Gly Lys Cys Lys Gly Leu Leu Gly
            35                  40                  45

Gly Gly Val Ser Val Glu Asp Cys Cys Leu Asn Thr Ala Phe Ala Tyr
 50                  55                  60

Gln Lys Arg Ser Gly Gly Leu Cys Gln Pro Cys Arg Ser Pro Arg Trp
 65                  70                  75                  80

Ser Leu Trp Ser Thr Trp Ala Pro Cys Ser Val Thr Cys Ser Glu Gly
                 85                  90                  95

Ser Gln Leu Arg Tyr Arg Arg Cys Val Gly Trp Asn Gly Gln Cys Ser
            100                 105                 110

Gly Lys Val Ala Pro Gly Thr Leu Glu Trp Gln Leu Gln Ala Cys Glu
            115                 120                 125

Asp Gln Gln Cys Cys Pro Glu Met Gly Gly Trp Ser Gly Trp Gly Pro
130                 135                 140

Trp Glu Pro Cys Ser Val Thr Cys Ser Lys Gly Thr Arg Thr Arg Arg
```

-continued

```
145                 150                 155                 160
Arg Ala Cys Asn His Pro Ala Pro Lys Cys Gly Gly His Cys Pro Gly
                165                 170                 175

Gln Ala Gln Glu Ser Glu Ala Cys Asp Thr Gln Gln Val Cys Pro Thr
                180                 185                 190

His Gly Ala Trp Ala Thr Trp Gly Pro Trp Thr Pro Cys Ser Ala Ser
            195                 200                 205

Cys His Gly Gly Pro His Glu Pro Lys Glu Thr Arg Ser Arg Lys Cys
        210                 215                 220

Ser Ala Pro Glu Pro Ser Gln Lys Pro Pro Gly Lys Pro Cys Pro Gly
225                 230                 235                 240

Leu Ala Tyr Glu Gln Arg Arg Cys Thr Gly Leu Pro Pro Cys Pro Val
                245                 250                 255

Ala Gly Gly Trp Gly Pro Trp Gly Pro Val Ser Pro Cys Pro Val Thr
                260                 265                 270

Cys Gly Leu Gly Gln Thr Met Glu Gln Arg Thr Cys Asn His Pro Val
            275                 280                 285

Pro Gln His Gly Gly Pro Phe Cys Ala Gly Asp Ala Thr Arg Thr His
    290                 295                 300

Ile Cys Asn Thr Ala Val Pro Cys Pro Val Asp Gly Glu Trp Asp Ser
305                 310                 315                 320

Trp Gly Glu Trp Ser Pro Cys Ile Arg Arg Asn Met Lys Ser Ile Ser
                325                 330                 335

Cys Gln Glu Ile Pro Gly Gln Gln Ser Arg Gly Arg Thr Cys Arg Gly
            340                 345                 350

Arg Lys Phe Asp Gly His Arg Cys Ala Gly Gln Gln Gln Asp Ile Arg
            355                 360                 365

His Cys Tyr Ser Ile Gln His Cys Pro Leu Lys Gly Ser Trp Ser Glu
        370                 375                 380

Trp Ser Thr Trp Gly Leu Cys Met Pro Pro Cys Gly Pro Asn Pro Thr
385                 390                 395                 400

Arg Ala Arg Gln Arg Leu Cys Thr Pro Leu Leu Pro Lys Tyr Pro Pro
                405                 410                 415

Thr Val Ser Met Val Glu Gly Gln Gly Glu Lys Asn Val Thr Phe Trp
                420                 425                 430

Gly Arg Pro Leu Pro Arg Cys Glu Glu Leu Gln Gly Gln Lys Leu Val
            435                 440                 445

Val Glu Glu Lys Arg Pro Cys Leu His Val Pro Ala Cys Lys Asp Pro
450                 455                 460

Glu Glu Glu Glu Leu
465
```